US012667348B2

(12) United States Patent
Thissen et al.

(10) Patent No.: US 12,667,348 B2
(45) Date of Patent: Jun. 30, 2026

(54) STEERABLE INSTRUMENT COMPRISING A TUBE ELEMENT

(71) Applicant: Fortimedix Assets II B.V., Geleen (NL)

(72) Inventors: Mattheus Hendrik Louis Thissen, Swalmen (NL); Marcel Antonius Elisabeth Verbeek, Voerendaal (NL); Roy Christiaan Louisa Velter, Nuth (NL)

(73) Assignee: Fortimedix Assets II B.V., Geleen (NL)

( * ) Notice: Subject to any disclaimer, the term of this patent is extended or adjusted under 35 U.S.C. 154(b) by 1004 days.

(21) Appl. No.: 17/285,513

(22) PCT Filed: Oct. 16, 2019

(86) PCT No.: PCT/NL2019/050680
§ 371 (c)(1),
(2) Date: Apr. 15, 2021

(87) PCT Pub. No.: WO2020/080938
PCT Pub. Date: Apr. 23, 2020

(65) Prior Publication Data
US 2021/0378648 A1 Dec. 9, 2021

(30) Foreign Application Priority Data
Oct. 16, 2018 (NL) ...................................... 2021823

(51) Int. Cl.
A61B 17/00 (2006.01)
A61B 1/005 (2006.01)
(Continued)

(52) U.S. Cl.
CPC ...... *A61B 17/00234* (2013.01); *A61B 1/0055* (2013.01); *A61B 1/0057* (2013.01);
(Continued)

(58) Field of Classification Search
CPC ............ A61B 17/00234; A61B 1/0055; A61B 1/0057; A61B 1/31; A61B 2017/00309;
(Continued)

(56) References Cited

U.S. PATENT DOCUMENTS

| 2,515,366 A | 7/1950 | Zublin |
| 2,717,146 A | 9/1955 | Zublin |

(Continued)

FOREIGN PATENT DOCUMENTS

| CH | 81017 A | 5/1919 |
| CN | 101522121 B | 9/2011 |

(Continued)

OTHER PUBLICATIONS

International Search Report and Written Opinion mailed Jun. 23, 2020, International Application No. PCT/NL2019/050680, 20 pages.

*Primary Examiner* — Sarah A Long
*Assistant Examiner* — Lauren Dubose
(74) *Attorney, Agent, or Firm* — Fortem IP LLP

(57) ABSTRACT

A steerable instrument has a proximal end and a distal end, a steering device (168), and a tubular body (18) extending in a longitudinal direction from said proximal end to said distal end. The tubular body (18) has an intermediate flexible zone (12a) and a distal deflectable zone (17) and a tube element made from a metal. The tube element has a first slotted structure (74) in the flexible zone (12a) and a second slotted structure (72; 106; 136; 156) in the deflectable zone (17). The tubular body (18) has tangential rotation blocking elements which form cable channels (96; 97; 146; 152), each cable channel (96; 97) accommodating one of a plurality of cables (90). The cables (90) are connected at the proximal end to the steering device (168) and at the distal end to the deflectable zone (17) to allow deflection of the deflectable zone (17) by the steering device (168).

11 Claims, 30 Drawing Sheets

(51) Int. Cl.
*A61B 1/31* (2006.01)
*A61M 25/01* (2006.01)

(52) U.S. Cl.
CPC ........... *A61B 1/31* (2013.01); *A61B 2017/003*
(2013.01); *A61B 2017/00309* (2013.01); *A61B*
*2017/00327* (2013.01); *A61M 25/0138*
(2013.01); *A61M 25/0147* (2013.01)

(58) Field of Classification Search
CPC ...... A61B 2017/00327; A61B 17/3421; A61B
90/50; A61B 2017/00305; A61B
2017/00323; A61B 2017/00526; A61B
2017/2905; A61B 2017/2906; A61B
2017/291; A61B 2017/2927; A61B
2017/3447; A61B 2017/347; A61B
1/0011; A61B 17/29; A61B 34/71; A61B
2017/2937; A61B 1/008; A61B 1/005;
A61B 1/0051; A61B 2017/00314; A61B
2017/00292; A61B 2017/003; A61B
2034/306; A61B 2034/301; A61B
2034/302; A61B 2034/303; A61B
2034/305; A61B 18/1492; A61M
25/0138; A61M 25/0147; A61M 25/0133;
A61M 25/0105; A61M 25/0141; B25J
18/06; B25J 9/104; B25J 9/10; B25J
9/08; B25J 9/0015; B25J 9/0024; B25J
9/106
See application file for complete search history.

(56) References Cited

U.S. PATENT DOCUMENTS

| | | | |
|---|---|---|---|
| 3,788,304 A | 1/1974 | Takahashi | |
| 4,362,520 A | 12/1982 | Perry | |
| 4,706,659 A | 11/1987 | Matthews et al. | |
| 4,745,908 A | 5/1988 | Wardle | |
| 5,271,381 A | 12/1993 | Ailinger et al. | |
| 5,749,828 A | 5/1998 | Solomon et al. | |
| 5,807,241 A | 9/1998 | Heimberger | |
| 5,928,136 A | 7/1999 | Barry | |
| 6,107,004 A | 8/2000 | Donadio, III | |
| 6,450,948 B1 | 9/2002 | Matsuura et al. | |
| 6,890,329 B2 | 5/2005 | Carroll et al. | |
| 7,189,228 B2 | 3/2007 | Eum et al. | |
| 7,320,700 B2 | 1/2008 | Cooper et al. | |
| 7,553,275 B2 | 6/2009 | Padget et al. | |
| 7,615,067 B2 | 11/2009 | Lee et al. | |
| 7,708,758 B2 | 5/2010 | Lee et al. | |
| 8,257,267 B2 | 9/2012 | Thornton | |
| 8,323,241 B2 | 12/2012 | Salahieh et al. | |
| 8,327,518 B2 | 12/2012 | Eberhard | |
| 8,382,742 B2 | 2/2013 | Hermann et al. | |
| 8,398,587 B2 | 3/2013 | Dewaele et al. | |
| 8,409,175 B2 | 4/2013 | Lee et al. | |
| 8,708,954 B2 | 4/2014 | Webler | |
| 8,740,884 B2 | 6/2014 | Verbeek | |
| 8,845,522 B2 | 9/2014 | McIntyre et al. | |
| 8,882,680 B2 | 11/2014 | Furlong et al. | |
| 8,968,355 B2 | 3/2015 | Malkowski et al. | |
| 8,986,317 B2 | 3/2015 | Verbeek | |
| 9,072,505 B2 | 7/2015 | Furlong et al. | |
| 9,138,566 B2 | 9/2015 | Cabiri | |
| 9,198,561 B2 | 12/2015 | Smith et al. | |
| 9,220,398 B2 | 12/2015 | Woodley et al. | |
| 9,339,271 B2 | 5/2016 | Ranucci et al. | |
| 9,421,343 B2 | 8/2016 | Berthiaume et al. | |
| 9,462,932 B2 | 10/2016 | Ostrovsky et al. | |
| 9,468,359 B2 | 10/2016 | Weisshaupt et al. | |
| 9,655,637 B2 | 5/2017 | Mueller | |
| 9,848,858 B2 | 12/2017 | Verbeek | |
| 9,877,720 B2 | 1/2018 | Worrell et al. | |
| 10,010,246 B2 | 7/2018 | Quaye | |
| 10,265,087 B2 | 4/2019 | Furlong et al. | |
| 10,405,876 B2 | 9/2019 | Boudreaux | |
| 10,420,537 B2 | 9/2019 | Salahieh et al. | |
| 10,441,746 B2 | 10/2019 | Besselink | |
| 10,449,010 B2 | 10/2019 | Dewaele et al. | |
| 10,456,556 B2 | 10/2019 | Cabiri | |
| 10,485,579 B2 | 11/2019 | Lenker | |
| 10,492,771 B2 | 12/2019 | Nunan | |
| 10,500,373 B2 | 12/2019 | Barrish et al. | |
| 10,524,868 B2 | 1/2020 | Cooper et al. | |
| 10,542,878 B2 | 1/2020 | Dewaele et al. | |
| 10,561,467 B2 | 2/2020 | Van Der Linde et al. | |
| 10,603,047 B2 | 3/2020 | Ding et al. | |
| 10,646,104 B1 | 5/2020 | Sinay et al. | |
| 10,729,457 B2 | 8/2020 | Lenker et al. | |
| 10,792,061 B2 | 10/2020 | Dewaele et al. | |
| 10,799,223 B2 | 10/2020 | Furlong et al. | |
| 10,874,290 B2 | 12/2020 | Walen et al. | |
| 10,962,093 B2 | 3/2021 | Dewaele et al. | |
| 11,007,026 B2 | 5/2021 | Kowshik | |
| 11,033,255 B2 | 6/2021 | Furlong et al. | |
| 11,051,794 B2 | 7/2021 | Cooper et al. | |
| 11,052,226 B2 | 7/2021 | Salahieh et al. | |
| 11,103,234 B2 | 8/2021 | Felix et al. | |
| 11,130,244 B2 | 9/2021 | Jogasaki | |
| 11,134,928 B2 | 10/2021 | Felix et al. | |
| 11,141,566 B2 | 10/2021 | Cabiri | |
| 11,241,557 B2 | 2/2022 | Besselink | |
| 11,278,704 B2 | 3/2022 | Pleijers | |
| 11,330,964 B2 | 5/2022 | Thissen | |
| 11,350,914 B2 | 6/2022 | Furlong et al. | |
| 11,382,654 B2 | 7/2022 | Lenker | |
| 11,419,691 B2 | 8/2022 | Kim et al. | |
| 11,457,904 B2 | 10/2022 | Dewaele et al. | |
| 11,523,807 B2 | 12/2022 | Furlong et al. | |
| 11,564,670 B2 | 1/2023 | Furlong et al. | |
| 11,576,735 B2 | 2/2023 | Blanckaert et al. | |
| 11,589,733 B2 | 2/2023 | Sinay et al. | |
| 11,607,242 B2 | 3/2023 | Tada et al. | |
| 11,642,114 B2 | 5/2023 | Thissen | |
| 11,660,101 B2 | 5/2023 | Walen et al. | |
| 11,696,677 B2 | 7/2023 | Thissen | |
| 11,730,921 B2 | 8/2023 | Besselink | |
| 11,730,927 B2 | 8/2023 | Laby et al. | |
| 11,839,401 B2 | 12/2023 | Lenker | |
| 12,048,819 B2 | 7/2024 | Yang et al. | |
| 12,295,550 B2 | 5/2025 | Tilson et al. | |
| 2002/0177750 A1 | 11/2002 | Pilvisto | |
| 2004/0138700 A1 | 7/2004 | Cooper et al. | |
| 2004/0199052 A1 | 10/2004 | Banik et al. | |
| 2004/0236316 A1 | 11/2004 | Danitz et al. | |
| 2005/0027245 A1 | 2/2005 | Sachdeva et al. | |
| 2005/0096694 A1 | 5/2005 | Lee | |
| 2005/0182298 A1* | 8/2005 | Ikeda ..................... A61B 34/70 600/104 |
| 2005/0272978 A1 | 12/2005 | Brunnen et al. | |
| 2005/0273084 A1 | 12/2005 | Hinman et al. | |
| 2005/0273085 A1 | 12/2005 | Hinman et al. | |
| 2006/0111210 A1 | 5/2006 | Hinman | |
| 2006/0199999 A1 | 9/2006 | Ikeda et al. | |
| 2006/0281566 A1 | 12/2006 | Lee | |
| 2007/0049800 A1 | 3/2007 | Boulais | |
| 2007/0250113 A1 | 10/2007 | Hegeman et al. | |
| 2007/0282371 A1 | 12/2007 | Lee et al. | |
| 2007/0287993 A1 | 12/2007 | Hinman et al. | |
| 2008/0249364 A1 | 10/2008 | Korner | |
| 2008/0300462 A1 | 12/2008 | Intoccia et al. | |
| 2009/0069632 A1 | 3/2009 | McIntyre et al. | |
| 2009/0124857 A1 | 5/2009 | Viola | |
| 2010/0151161 A1 | 6/2010 | Da Rolo | |
| 2010/0228191 A1 | 9/2010 | Alvarez et al. | |
| 2010/0234831 A1 | 9/2010 | Hinman et al. | |
| 2010/0286480 A1 | 11/2010 | Peine et al. | |
| 2010/0287755 A1 | 11/2010 | Eberhard | |
| 2011/0004157 A1 | 1/2011 | Dewaele et al. | |
| 2011/0251599 A1 | 10/2011 | Shellenberger et al. | |
| 2011/0295065 A1 | 12/2011 | Gurusamy et al. | |
| 2012/0116163 A1 | 5/2012 | Lutze et al. | |
| 2012/0143175 A1 | 6/2012 | Hermann et al. | |

(56) References Cited

U.S. PATENT DOCUMENTS

| | | |
|---|---|---|
| 2012/0245414 A1 | 9/2012 | Verbeek |
| 2012/0277730 A1 | 11/2012 | Salahieh et al. |
| 2012/0323077 A1 | 12/2012 | Verbeek |
| 2013/0184528 A1 | 7/2013 | Onuki et al. |
| 2013/0197490 A1 | 8/2013 | Stanton et al. |
| 2013/0253469 A1 | 9/2013 | Freed |
| 2014/0018620 A1 | 1/2014 | Verbeek |
| 2014/0066706 A1* | 3/2014 | McWeeney ............ A61B 1/008 |
| | | 600/104 |
| 2014/0249474 A1 | 9/2014 | Suon et al. |
| 2015/0099997 A1 | 4/2015 | Cabiri |
| 2015/0107396 A1 | 4/2015 | Suehara |
| 2015/0112134 A1 | 4/2015 | Suehara et al. |
| 2015/0157353 A1 | 6/2015 | Lenker et al. |
| 2015/0352728 A1 | 12/2015 | Wang |
| 2015/0366445 A1 | 12/2015 | Rutgers |
| 2016/0015249 A1 | 1/2016 | Suehara |
| 2016/0096004 A1 | 4/2016 | Gerrans et al. |
| 2016/0136393 A1 | 5/2016 | Tsai et al. |
| 2016/0278616 A1 | 9/2016 | Viebach et al. |
| 2017/0027597 A1 | 2/2017 | Walen |
| 2017/0027607 A1 | 2/2017 | Verbeek et al. |
| 2017/0105746 A1 | 4/2017 | O'Keefe et al. |
| 2017/0273546 A1* | 9/2017 | Ishizaki ............... A61B 1/0055 |
| 2018/0049873 A1 | 2/2018 | Manash et al. |
| 2018/0055589 A1 | 3/2018 | Joseph et al. |
| 2018/0078247 A1* | 3/2018 | Nakadate ............... A61B 17/28 |
| 2018/0289241 A1 | 10/2018 | Zhou et al. |
| 2019/0111237 A1 | 4/2019 | Cabiri |
| 2019/0111238 A1 | 4/2019 | Schultz et al. |
| 2019/0175869 A1 | 6/2019 | Kirt et al. |
| 2020/0275983 A1 | 9/2020 | Dewaele et al. |
| 2020/0330729 A1 | 10/2020 | Petitpierre et al. |
| 2021/0267702 A1 | 9/2021 | Kim et al. |
| 2021/0275266 A1 | 9/2021 | Kim et al. |
| 2021/0378648 A1 | 12/2021 | Thissen et al. |
| 2022/0061634 A1 | 3/2022 | Thissen et al. |
| 2022/0087666 A1 | 3/2022 | Sharma et al. |
| 2022/0117576 A1 | 4/2022 | Mixter et al. |
| 2022/0167836 A1 | 6/2022 | Thissen et al. |
| 2022/0168008 A1 | 6/2022 | Thissen et al. |
| 2022/0331003 A1 | 10/2022 | Cohen et al. |
| 2023/0031313 A1 | 2/2023 | Lynn et al. |
| 2023/0131647 A1 | 4/2023 | Magno et al. |
| 2023/0165573 A1 | 6/2023 | Furlong et al. |
| 2023/0190329 A1 | 6/2023 | Tada et al. |
| 2023/0255644 A1 | 8/2023 | Walen et al. |
| 2024/0138946 A1 | 5/2024 | Swoyer et al. |
| 2024/0173130 A1 | 5/2024 | McNiven et al. |
| 2024/0216008 A1 | 7/2024 | Lenker |
| 2024/0245284 A1 | 7/2024 | Thissen |
| 2024/0306900 A1 | 9/2024 | Thissen et al. |
| 2024/0389835 A1 | 11/2024 | Thissen et al. |
| 2025/0049305 A1 | 2/2025 | Thissen |
| 2025/0049307 A1 | 2/2025 | Thissen |

FOREIGN PATENT DOCUMENTS

| | | |
|---|---|---|
| DE | 3219629 A1 | 12/1983 |
| DE | 4222121 C1 | 9/1993 |
| DE | 102009037030 A1 | 2/2011 |
| DE | 102010000787 A1 | 7/2011 |
| DE | 102010005243 A1 | 7/2011 |
| DE | 102010000787 B4 | 9/2014 |
| EP | 0626604 A2 | 11/1994 |
| EP | 0764423 A1 | 3/1997 |
| EP | 0782836 A1 | 7/1997 |
| EP | 1708609 A1 | 10/2006 |
| EP | 1977677 B1 | 8/2009 |
| EP | 2259710 B1 | 5/2013 |
| EP | 2 249 691 B1 | 7/2013 |
| EP | 1842501 B1 | 11/2017 |
| EP | 2858577 B1 | 4/2018 |
| GB | 2469388 A | 10/2010 |
| JP | 2008188095 A | 8/2008 |
| JP | 2012075659 A | 4/2012 |
| JP | 2015213758 A | 12/2015 |
| JP | 2017-537664 A | 12/2017 |
| KR | 101312071 B1 | 9/2013 |
| NL | 2030160 B1 | 6/2023 |
| WO | 97/42910 A1 | 11/1997 |
| WO | 1997042910 A1 | 11/1997 |
| WO | 0213682 A1 | 2/2002 |
| WO | 02065933 A2 | 8/2002 |
| WO | 03/037416 A1 | 5/2003 |
| WO | 2004052171 A1 | 6/2004 |
| WO | 2004103430 A2 | 12/2004 |
| WO | 2006/116457 A2 | 11/2006 |
| WO | 2007/039875 A2 | 4/2007 |
| WO | 2008139768 A1 | 11/2008 |
| WO | 2009/098244 A2 | 8/2009 |
| WO | 2009/112060 A1 | 9/2009 |
| WO | 2010105649 A1 | 9/2010 |
| WO | 2010/136272 A1 | 12/2010 |
| WO | 2010/136274 A1 | 12/2010 |
| WO | 2010/151698 A2 | 12/2010 |
| WO | 2011018147 A1 | 2/2011 |
| WO | 2011018179 A2 | 2/2011 |
| WO | 2011079897 A1 | 7/2011 |
| WO | 2012035531 A1 | 3/2012 |
| WO | 2012139869 A2 | 10/2012 |
| WO | 2013084985 A1 | 6/2013 |
| WO | 2013173197 A1 | 11/2013 |
| WO | 2014186736 A1 | 11/2014 |
| WO | 2015/061692 A1 | 4/2015 |
| WO | 2015051070 A1 | 4/2015 |
| WO | 2015085307 A1 | 6/2015 |
| WO | 2016/041792 A1 | 3/2016 |
| WO | 2016054063 A1 | 4/2016 |
| WO | 2016/089202 A1 | 6/2016 |
| WO | 2016114981 A1 | 7/2016 |
| WO | 2016/172706 A1 | 10/2016 |
| WO | 2017010883 A2 | 1/2017 |
| WO | 2017014624 A1 | 1/2017 |
| WO | 2017082720 A1 | 5/2017 |
| WO | 2017/204869 A1 | 11/2017 |
| WO | 2017/213491 A1 | 12/2017 |
| WO | 2018/067004 A1 | 4/2018 |
| WO | 2018083674 A2 | 5/2018 |
| WO | 2019/009710 A1 | 1/2019 |
| WO | 2019077461 A1 | 4/2019 |
| WO | 2019/118524 A1 | 6/2019 |
| WO | 2019159142 A1 | 8/2019 |
| WO | 2020/080938 A2 | 4/2020 |
| WO | 2020/214027 A2 | 10/2020 |
| WO | 2021/044386 A1 | 3/2021 |
| WO | 2024033706 A1 | 2/2024 |
| WO | 2025026670 A1 | 2/2025 |
| WO | 2025026702 A1 | 2/2025 |

* cited by examiner

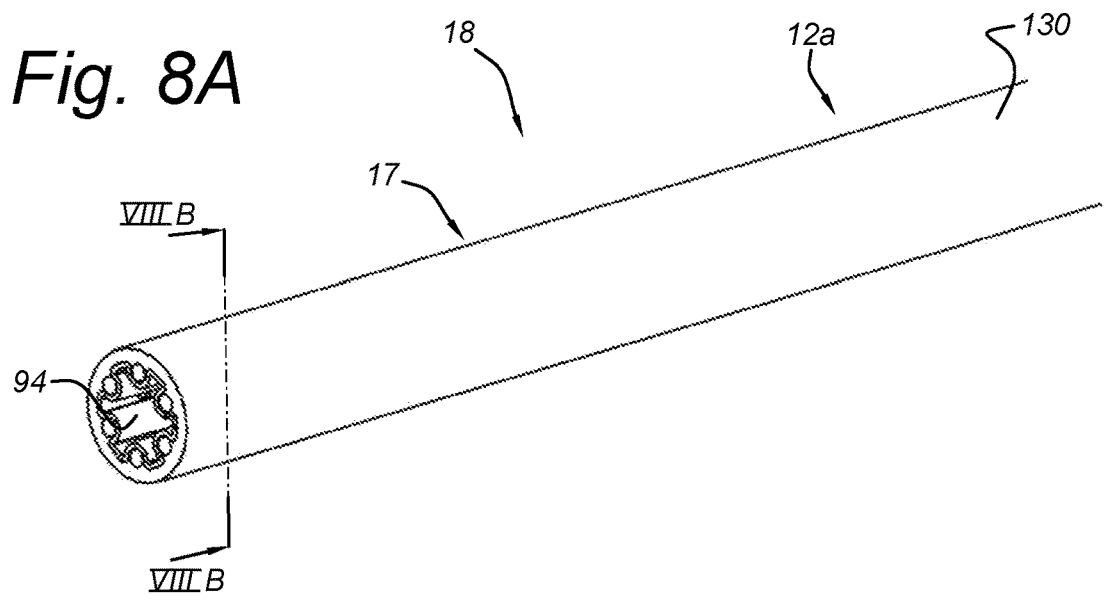
*Fig. 8A*
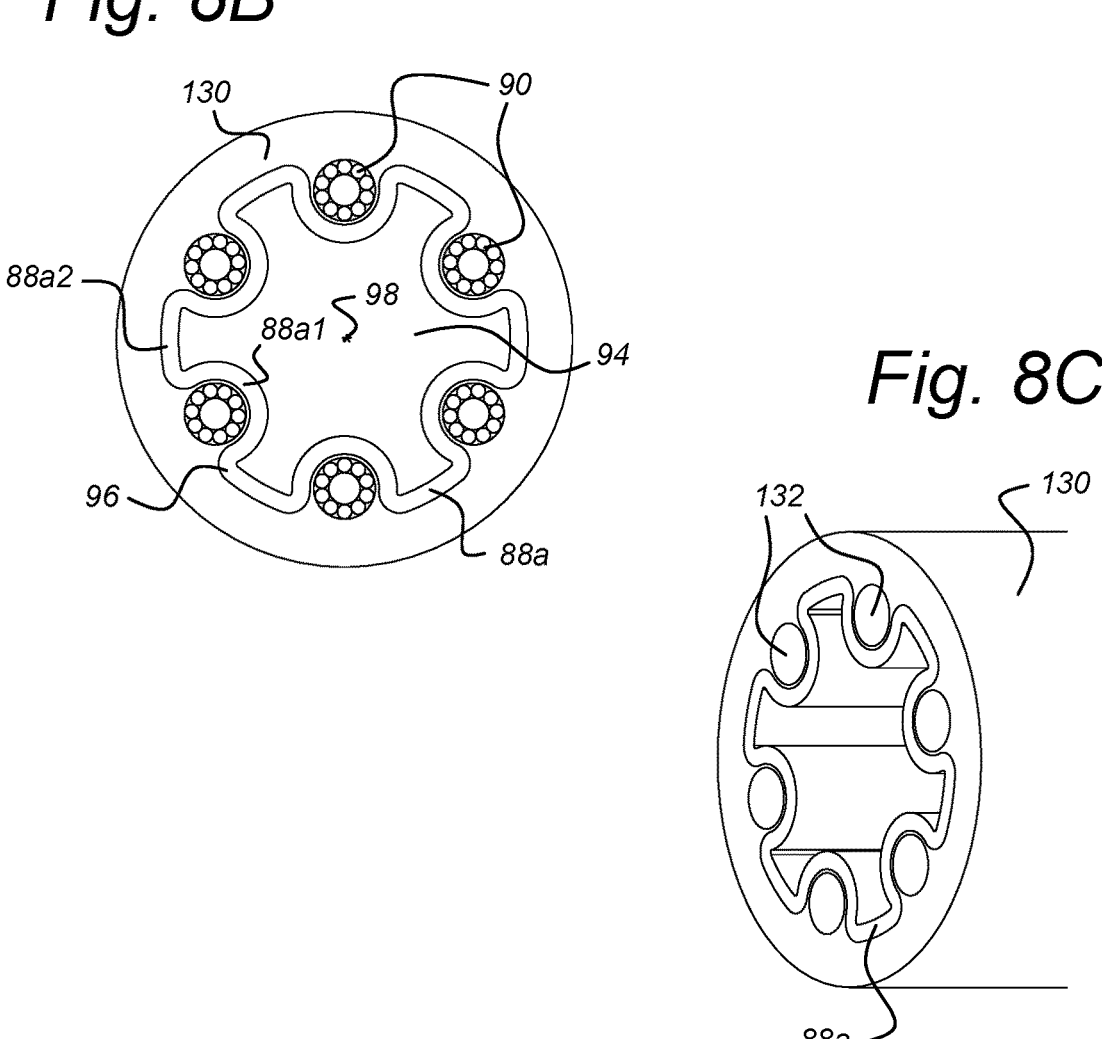
*Fig. 8B*
*Fig. 8C*

STEERABLE INSTRUMENT COMPRISING A TUBE ELEMENT

FIELD OF THE INVENTION

The present invention relates to a steerable instrument for invasive and non-invasive type of applications, such as in surgery. Such instruments can be used in, for instance, the field of gastroscopy, colonoscopy, endoscopy, laparoscopy, and other medical applications. However, the steerable instrument according to the invention can also be used in non-medical applications. Examples of the latter include inspection and/or repair of mechanical and/or electronic hardware at locations that are difficult to reach.

BACKGROUND ART

Transformation of surgical interventions that require large incisions for exposing a target area into minimal invasive surgical interventions, i.e. requiring only natural orifices or small incisions for establishing access to the target area, is a well-known and ongoing process. In performing minimal invasive surgical interventions, an operator such as a physician, requires an access device that is arranged for introducing and guiding invasive instruments into the human or animal body via an access port of that body. In order to reduce scar tissue formation and pain to a human or animal patient, the access port is preferably provided by a single small incision in the skin and underlying tissue. In that respect the possibility to use a natural orifice of the body would even be better. Furthermore, the access device preferably enables the operator to control one or more degrees of freedom that the invasive instruments offer. In this way, the operator can perform required actions at the target area in the human or animal body in an ergonomic and accurate manner.

Steerable surgical invasive instruments in the field of gastroscopy, colonoscopy, endoscopy, laparoscopy, etc. are well-known in the art. The invasive instruments can comprise a steerable tube shaped device that enhances its navigation and steering capabilities. Such a steerable tube shaped device may comprise a proximal end part, a distal end part including at least one deflectable zone, and a rigid or flexible intermediate part, wherein the steerable tube shaped device, at its proximal end, further comprises a steering arrangement that is adapted to deflect the distal deflectable zone relative to a central axis of the tube shaped device. Such a steering arrangement may e.g. comprise a proximal deflectable zone, a ball shaped element, or a robot.

Most of the known instruments are complex to manufacture resulting in expensive instruments. Often, the distal end of the instruments comprise a flexible zone that is composed of separate links with hinging pins, coils or flexible plastic extrusions. Steering cables should be guided through holes through these links and/or through guiding eyes or hooks. In most prior art devices, the steering arrangement comprises conventional steering cables with, for instance, sub 1 mm diameters as control members, wherein the steering cables are arranged between related deflectable zones at the distal end part and the steering arrangements at the proximal end part of the tube shaped device. Alternatively, control members may be implemented by one or more sets of longitudinal elements that are, e.g., formed by laser cutting in tube elements. Further details regarding the design and fabrication of the abovementioned steerable tube and the steering arrangement thereof have been described for example in WO 2009/112060 A1, WO 2009/127236 A1, WO 2017/213491 A1, and WO 2018/067004. Such instruments can advantageously be used in endoscopic operations where the length need not be more than say 1 meter.

Sometimes a plastic extruded tube can be used with integrated channels for accommodating the cables. This renders an instrument with a simple construction. However, most plastics are rather weak. In case of very long instruments, e.g. longer than 1 meter, therefore, problems may arise due to the high forces exerted on the cables, both the steering cables and the actuation cable arranged to operate the tool at the distal end of the instrument. Problems may be undesired cuts, slip stick effects in the plastic tube and often a too high friction on the cables causing steering by the steering cables to be difficult and hard to manage. Moreover, mechanical properties of many plastics may be too poor to guarantee a high enough torsion stiffness which is required because the instruments should be capable of being rotated in use where they may have been guided through several curves impeding rotation of the whole instrument. Another disadvantage of a plastic tube may be that in case it is provided with an actuation cable to operate a tool at the distal end of the instrument the force in the actuation cable can increase to an extent that it exceeds the maximum longitudinal force allowed in the extruded plastic tube. If so, it would be impossible to operate the tool with an acceptable force. Moreover, if the plastic tube is in a curved arrangement and high force is exerted on the actuation cable, the channels for the steering cables may be deformed, especially in bent/deflected portions, such that the steering cables are clamped and cannot move freely anymore in the channels, thus, impeding proper operation of the steering of the distal deflectable zones.

In medical applications where longer instruments are necessary, such as in colonoscopy where 1.5 meter long instruments (or longer) may be applied, requirements as to steerability, flexibility, stiffness and accuracy increase seriously. There is a desire to develop such instruments with a better performance than prior art devices as to steerability also under end-effector actuation, longitudinal stiffness, torsion stiffness, durability and applicability of a mechanically actuated tool at the distal end. Moreover, there is a need to design such instruments such that they can be manufactured at such low costs that they are, preferably, disposable, thus avoiding the need to reuse them because of cost efficiency which requires applying cleaning and sterilization of the instrument after each use. Improper cleaning and sterilization may result in undesired post-operative complications which is a well-known and frequently occurring problem.

US2004/0236316 discloses an articulating mechanism for remote manipulation of various surgical instruments and diagnostic tools within, or to, regions of the body. Movement of segments at the proximal end of the mechanism results in a corresponding, relative movement of segments at the distal end of the mechanism. The proximal and distal segments are connected by a set of cables in such a fashion that each proximal segment forms a discrete pair with a distal segment. This configuration allows each segment pair to move independently of one another. Each segment comprises a link element having closed channels and optionally a channel being open towards the outside surface. The channels accommodate cables for different purposes. Adjacent links touch another and are movable relative to one another in any angular direction relative to a longitudinal central axis of the instrument. Since the instrument has to be made of many separate links and all cables have to be guided through all channels of all links individually, manufacturing of the instrument according to this prior art document is time consuming and complex.

US2005096694 discloses an endoscopic or laparoscopic instrument which includes a distal tool, a rigid or flexible elongated shaft that supports the distal tool, and a proximal handle or control member, where the tool and the handle are coupled to the respective distal and proximal ends of the elongated shaft via bendable motion members. In FIGS. 21A-23D, this document shows a bendable section which is made from a solid element in which channels are made in its longitudinal direction to accommodate cables and which has a slotted structure to provide the required bendability. No materials used for making the bendable section are mentioned in this document. Moreover, the structure as shown would be extremely difficult to make from metal and therefor would be typically made from plastic. Both this material and the shown structure are unsuitable for longer devices because of high manufacturing cost and of too low mechanical properties for longitudinal and rotational stiffness WO2005/067785 discloses an instrument for high-precision or surgical applications of a minimally invasive nature, comprising a distally positioned directable head, a shaft upon which the head is positioned, and a proximally positioned handgrip for operating the head. A ring of cables comprising longitudinally extending cables connects to the head. Each cable of the ring of cables is disposed such that at least a part of both sides is in direct contact with another cable of the ring of cables. The cables are fixedly secured in the radial direction, e.g. by an outer tube and an inner coil. A disadvantage of this known instrument is that the ring of cables is not blocked from tangential rotation relative to the outer tube and/or inner coil which may result in insufficient steerability of the instrument when the instrument is actuated to make two curves in different directions. Upon actuation, the pulled cables have the tendency to seek for the shortest route from the steering end to the distal end and therefore have the tendency to move to the inner curve of the instrument and thus tangentially rotate about the instrument longitudinal axis. This will result in loss of steering. Moreover, because the cables of the ring of cables at least in part contact adjacent cables there is friction between adjacent cables. Furthermore, in operation, in bent/deflected parts of the instrument a force may be exerted on some cables such that they have a tendency of being clamped between an adjacent cable and the outer tube/inner coil because of a "wedge" effect. Secondly, in a curve, the steering wires in the inner curve are clamped between the inner and outer tube if tension is applied to the outer steering wires. This can result in uncontrolled steering.

In this application, the terms "proximal" and "distal" are defined with respect to an operator, e.g. a physician that operates the instrument or endoscope. For example, a proximal end part is to be construed as a part that is located near the physician and a distal end part as a part located at a distance from the physician.

In the context of this document, to explain the invention, the term "colonoscopic instrument" will be used. The term is not used to limit its application to certain types of operations in a body or elsewhere.

SUMMARY OF THE INVENTION

It is an object of the invention to provide a steerable instrument for medical and non-medical operations that has a high steerability even in case the instrument has to be as long as, e.g., 2 meter and in case an end-effector is actuated.

This is achieved by a steerable instrument as claimed in claim 1.

Thus, the tubular body according to the invention can be designed such that it meets high demands as to rotational stiffness, longitudinal stiffness, flexibility, with variable bending stiffnesses, along its entire length and deflectability at its deflectable zones which is especially an issue for instruments with a relatively small diameter and that are longer than 1 m. It becomes possible to make a single use instrument at fair costs which combines several functions like controlling a tool (if applied), rotating a tool, deflecting a tip section, adapting to curves in a longer duct, as required in colonoscopy and gastroscopy. The instrument is suitable for complex operations and is a step forward in minimal invasive gastro-intestinal surgery.

The invention also relates to a method of manufacturing a flexible tube element as defined in an independent method claim.

In a second aspect, the invention relates to a steerable instrument having a proximal end and a distal end and comprising at least one steering device arranged at said proximal end, a tubular body surrounding a first channel extending in a longitudinal direction along a first central axis from said proximal end to said distal end, the tubular body having a flexible zone and at least one deflectable zone arranged distally from said flexible zone, said at least one deflectable zone being connected to said steering device by one or more cables allowing deflection of said at least one deflectable zone by said steering device, said steering device comprising:

a supporting member having a second channel having a second central axis arranged in line with said first central axis, said second channel extending from a distal side to a proximal side of the supporting member, the tubular body extending from a distal side of the supporting member, the supporting member having a ball-shaped member arranged around said second channel at the proximal side of the supporting member;

a steering member having a cable fastening mechanism connected to said one or more cables, and being rotationally arranged on said ball-shaped member such as to allow either pulling or relaxing said one or more cables.

Thus, a steerable instrument is provided with a proximally arranged steering device with a high stability and steering capability.

Embodiments of the invention are claimed in dependent claims.

Further features and advantages of the invention will become apparent from the description of the invention by way of non-limiting and non-exclusive embodiments. These embodiments are not to be construed as limiting the scope of protection. The person skilled in the art will realize that other alternatives and equivalent embodiments of the invention can be conceived and reduced to practice without departing from the scope of the present invention. Moreover, separate features of different embodiments can be combined, even if not explicitly shown in the drawings or explained in the specification, unless such combination is physically impossible. The scope of the present invention is only limited by the claims and their technical equivalents.

BRIEF DESCRIPTION OF THE DRAWINGS

The present invention will be discussed in more detail below, with reference to the attached drawings, in which like or same reference symbols denote like, same or corresponding parts, and in which:

FIGS. 8A, 8B, 8C show a tube having a corrugated cross section with cable channels covered with an integrated plastic liner.

DESCRIPTION OF EMBODIMENTS

Figure 1:
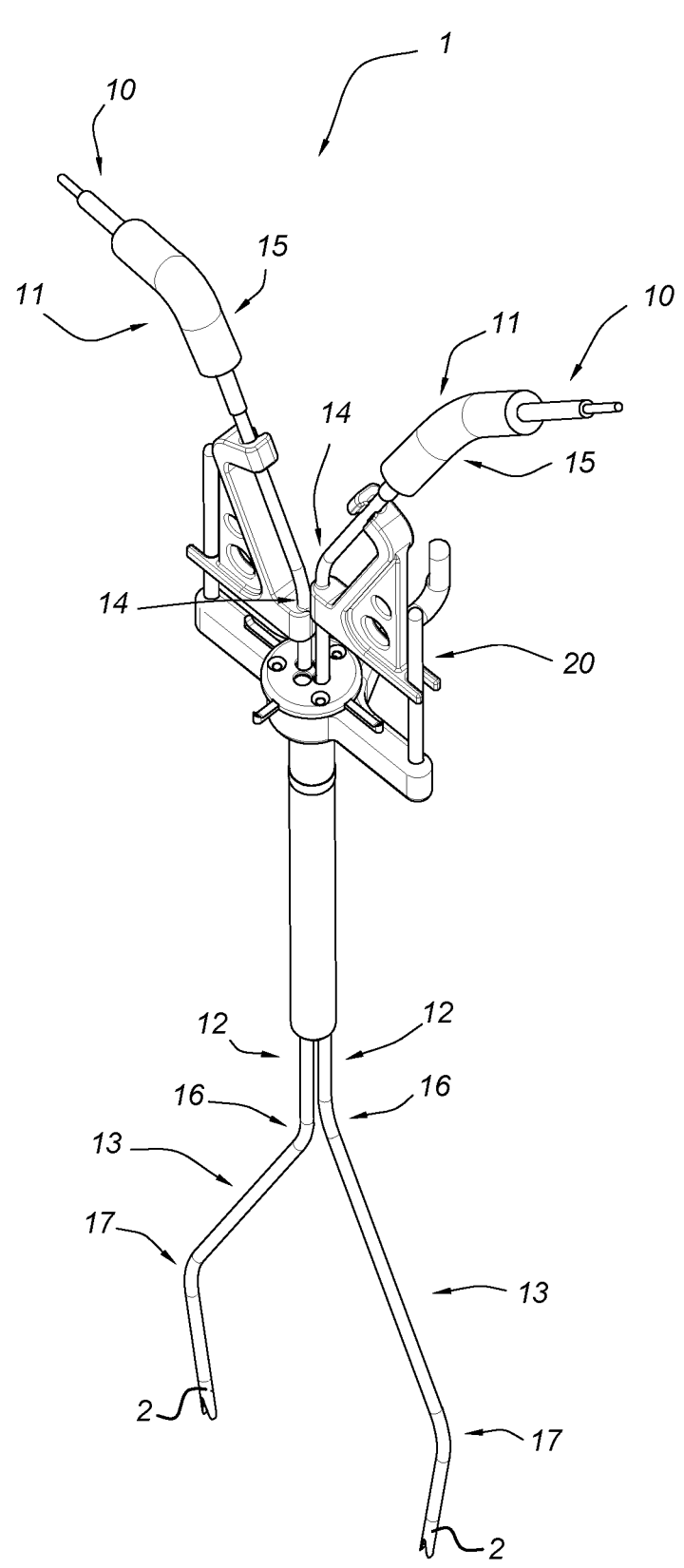
FIG. 1 depicts general setup for operations where two deflectable instruments are used, each with two distal deflectable zones.
Figure 2:
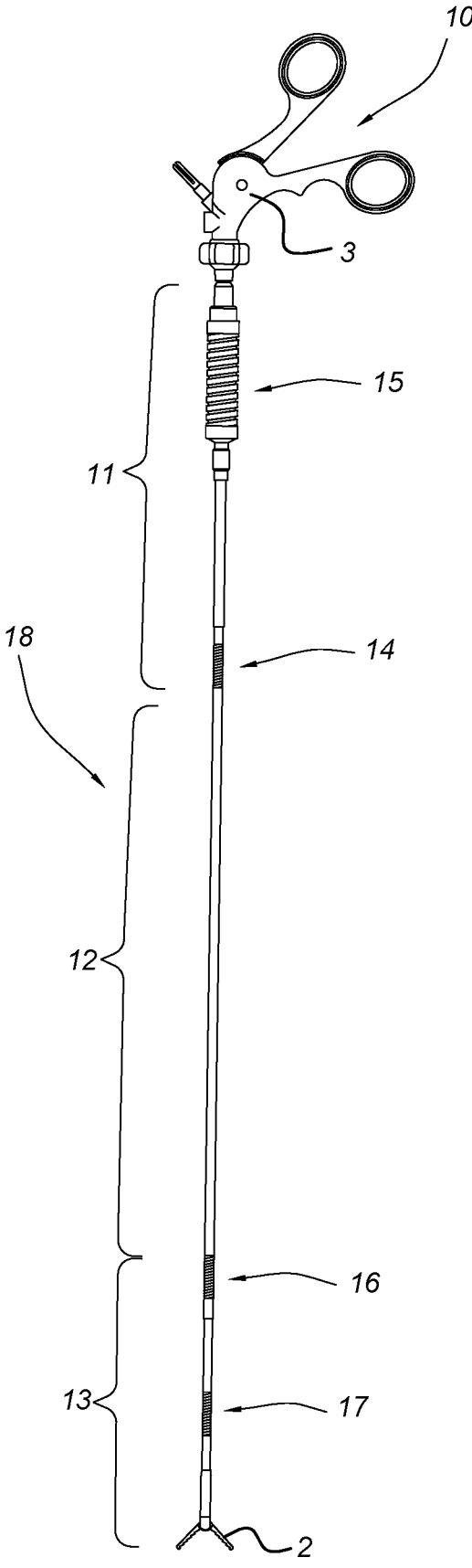
FIG. 2 shows one deflectable instrument with two deflectable zones.

FIG. 1 shows a non-limiting embodiment of an invasive instrument assembly 1 having an introducer accommodating two steerable invasive instruments 10. FIG. 2 shows a side view of the steerable invasive instrument 10.

Each steerable instrument 10 (cf. FIG. 2) comprises an elongated tubular body 18 having a proximal end part 11 including two actuation deflectable zones 14, 15, a distal end part 13 including two distal deflectable zones 16, 17, and a rigid intermediate part 12. The actuation deflectable zones 14, 15 in the present embodiment are configured as deflectable proximal zones, and will further be referred to as deflectable proximal zones. These deflectable proximal zones 14, 15 are connected to the distal deflectable zones by suitable longitudinal elements (not shown in FIG. 2). Such longitudinal elements may be cables. Alternatively, such longitudinal elements may be implemented by longitudinal strip shaped elements in tube elements and separated by longitudinal slots resulting from laser cutting predetermined patterns in the cylindrical tube, as explained in detail in for example WO 2009/112060 A1, WO 2009/127236 A1, WO 2017/213491 A1, and WO 2018/067004. As an alternative to laser cutting other techniques may be used, e.g., cutting by means of water beams. Also, 3D laser printing may be used. This also holds for other embodiments discussed below where reference is made to laser cutting.

By deflecting one such proximal deflectable zone 14, 15, respectively, in an angular direction from a longitudinal axis of the instrument a corresponding deflectable distal zone 16, 17 will also deflect. The rigid intermediate part 12 may also have one more flexible zones. However, these flexible zones are just flexible and their bending is not controlled by another bendable zone. If desired, one or more steerable deflectable distal zones 16, 17 can be provided.

At the distal end part 13 a tool, like a forceps 2 is arranged. At the proximal end part 11 a handle 3 is arranged that is adapted for opening and closing the jaws of the forceps 2 via, e.g., a suitable actuation cable (not shown) arranged within the instrument. Cable arrangements for doing so are well known in the art.

The steerable instrument typically comprises a handle 3 that is arranged at the proximal end part of the steerable tube for steering the tube and/or for manipulating the tool, such as forceps 2 that is arranged at the distal end part of the steerable tube. Alternatively, such a tool can for example be a camera, a manual manipulator, e.g. a pair of scissors, manipulators using an energy source, e.g. an electrical, ultrasonic or optical energy source. The instrument has no limitation as to the type of tool applied at the distal end. The type of handle 3 will be selected in dependence on the type of tool applied at the distal end, as will be evident to persons skilled in the art.

FIG. 1 shows two instruments 18 of FIG. 2 inserted into an introducer 20. Such an introducer 20 can, during an operation, be inserted into a trocar (not shown) arranged in, e.g., a abdominal wall of a human. Further details of an example of such an introducer 20 are disclosed in WO2015/084157. Both instruments 18 are deflected at proximal deflectable zones 14, 15 causing distal deflectable zones 16, 17 to be deflected too. The setup of FIG. 2 can typically be used in laparoscopic applications.

Some locations to be operated in a body need specifically designed instruments. E.g., by making the intermediate part 12 of the instrument of FIG. 2 completely flexible, the instrument can also be used in areas in the body which are only accessible via curved natural access guides/channels, like the colon, the stomach via the oesophagus or the heart via curved blood vessels.

Figure 3:
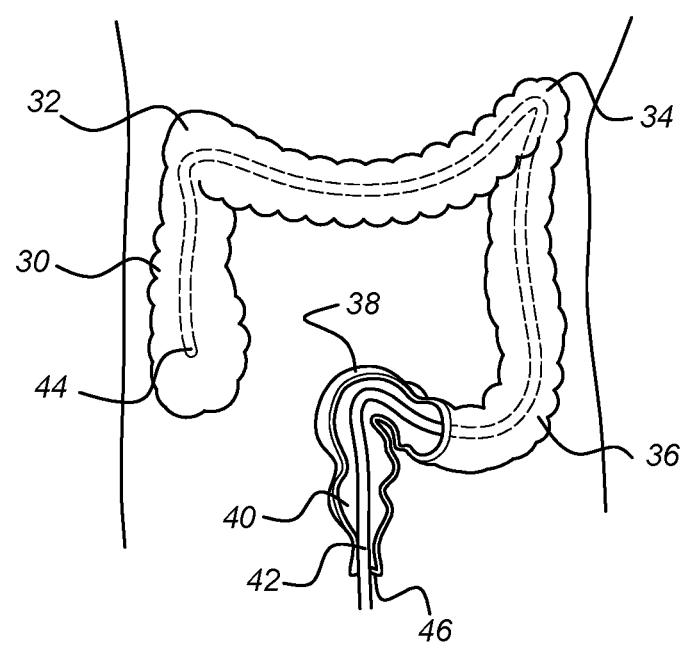
FIG. 3 shows a schematic picture of a colonoscopic instrument in use.

FIG. 3 shows a schematic view of a colonoscope 42 in use. The colonoscope 42 is inserted into a colon 30 of a human body. Typically, the colon 30 has several almost square angled sections 32, 34, 36, and 38. If a surgeon needs to operate an area of the colon 30 upstream from square angled section 32 the colonoscope 42 needs to be inserted into the colon 30 along a distance of up to 1.5 meter. Moreover, the colonoscope 42 needs to be so flexible that it can be guided from an anus through all squared angled sections 32-38 of the colon 30 easily without risks of damaging the inner wall of the colon 30.

In operation, usually, several invasive instruments are inserted through the colonoscope 42 to provide one or more tools for some function at its distal end 44. In colonoscopy, such a tool typically includes a camera lens and a lighting element. To assist the surgeon in steering the camera view to the desired location and view in colon 30, typically, the distal end is deflectable from a longitudinal axis in all angular directions. This also holds for the inserted instruments with tools 2. That can be implemented by providing such an instruments with one or more deflectable zones, like the deflectable zones 16, 17 of the instrument shown in FIG. 2. These distal deflectable zones are controlled by suitable steering cables accommodated in the instruments connected to a suitable steering mechanism at the proximal ends of the instruments.

Figure 4:
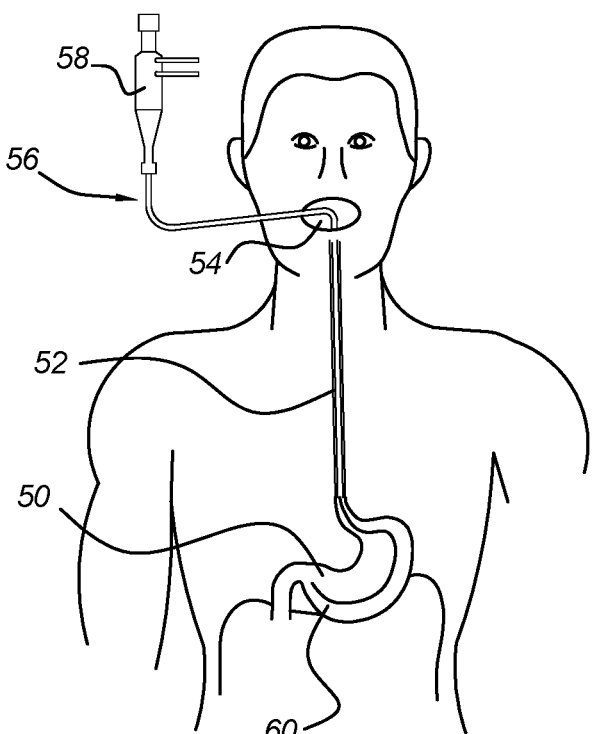
FIG. 4 shows a schematic picture of a gastroscopic instrument in use.

FIG. 4 shows a schematic view of a gastroscope 56 in use. The gastroscope 56 is inserted into a stomach 50 of a human body via mouth, oral cavity/throat 54 and oesophagus 52. Especially when a surgeon needs to operate a lower portion of the stomach 50, the gastronoscope 56 needs to be guided through several curved/angled sections. Therefore, the gastroscope 56 needs to be flexible such that there is little risk of damaging inner walls of the mouth/throat 54, oesophagus 52 and stomach 50.

Figures 5A, 5B, 5C:
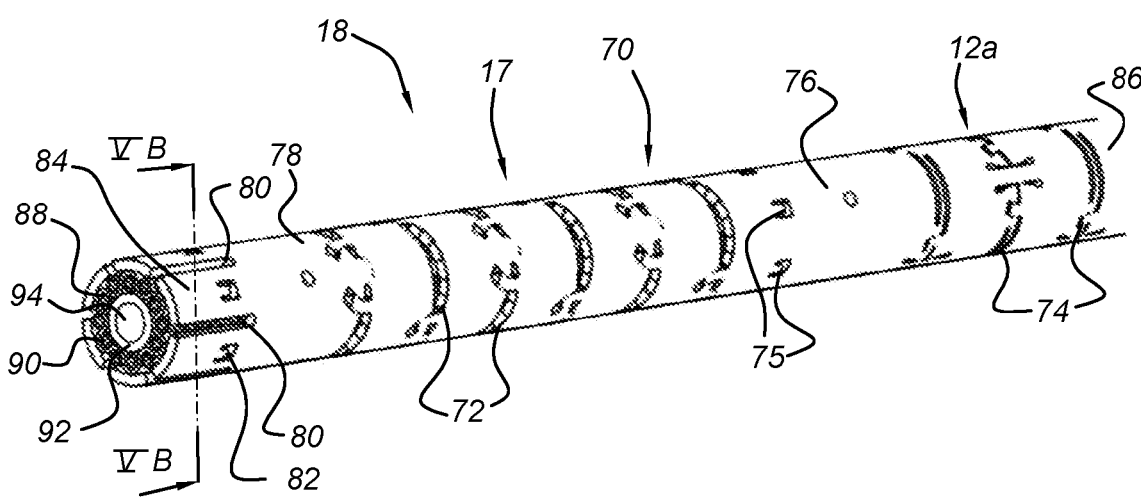
FIGS. 5A, 5B, 5C, 6A, 6B, 6C, 7A, 7B, 7C, 7D show different views of embodiments of the invention in which a tube with a corrugated cross section is used such as to define cable channels for steering cables.

In operation, usually, several invasive instruments are inserted through the gastroscope 56 to provide one or more tools for some function at its distal end 60. In gastroscopy, such a tool typically includes a camera lens and a lighting element. To assist the surgeon in steering the camera view to the desired location and direction in stomach 50, typically, the distal end 60 of the is deflectable from a longitudinal axis in all angular directions. This also holds for the inserted instruments with tools 2. That can be implemented by providing such an instrument with one or more deflectable zones, like the deflectable zones 16, 17 of the instrument shown in FIG. 2. These distal deflectable zones are controlled by suitable steering cables accommodated in the instruments connected to a suitable steering mechanism of these instruments. instruments according to the invention can be used in such colonoscopes and gastroscopes. Therefore, general requirements to the presented instrument are that they show a high rotational stiffness, high longitudinal stiffness, flexibility along its entirely length and deflectability at its deflectable zones even in cases of long instruments, e.g., longer than 1 m, and with a relatively small diameter that fits to the working channels within or attached to colonoscopes and gastroscopes Also, such instruments should be designed such that they can be manufactured quite easily. In accordance with the invention this can be achieved with instruments having a tubular body with at least one tube element made from a metal and provided with suitable slotted structures to provide the instrument with enough flexibility along its entire length FIGS. 5A-5C show a first embodiment of the present invention. FIG. 5C is an enlarged version of the tip of the instrument shown in FIG. 5A. FIG. 5B is a cross section view through the tip at a location indicated with the two arrows VB in FIGS. 5A and 5C.

FIG. 5A shows a 3D view of the distal end 70 of the elongated tubular body 18 of the steerable instrument between a tool and the proximal end of the steerable instrument according to the embodiment. The elongated tubular body 18 comprises an outer tube element 86, an intermediate tube element 88 and an inner tube element 92. The elongated tubular body 18 may comprise more tube elements located outside the outer tube element 86 or inside the inner tube element 92 or between the inner and outer tube elements 92, 86 at either side of the intermediate tube element 88. The inner tube element 92 surrounds an elongated channel 94 extending from the distal end 70 towards the proximal end of the tubular body 18. Preferably, all tube elements 86, 88, 92 are symmetrical about a central longitudinal axis 98 of the tubular body 18. They are shown as cylindrical elements with a substantial circular cross section. However, they may have other cross sections like an oval, hexagon, rectangle, etc. Moreover, it is observed that cross sections of several tube elements of the present invention may deviate from an ideal circle, or oval or hexagon, etc.

Intermediate tube element 88 functions as a tangential rotation blocker for cables 90.

In the embodiment shown, the tubular body 18 has one deflectable zone 17. Between this deflectable zone 17 and the proximal end the tubular body has a flexible zone 12a. In the deflectable zone 17 and the flexible zone 12a all tube elements 86, 88, and 90 are flexible. The deflection of deflectable zone 17 is controlled by steering cables 90. When operating the steering cables 90 also the flexible zone 12a will show a tendency to deflect. However, preferably, the deflectable zone 17 is more flexible than flexible zone 12a such that deflectable zone 17 will bend more easily than flexible zone 12a when steering cables 90 are operated. Moreover, cables 90 will typically be operated when the tubular body 18 has been inserted in an object to its target location and, then, deflectable zone 17 will have more free space in the object than the flexible zone 12a which may be located in a rather fixed orientation as determined by one or more curved sections (like a colon) of the object through which the tubular body 18 extends. E.g., when tubular body 18 has been inserted into a colonoscope or gastroscope to such an extent that the distal end, including deflectable zone 17, extends from the distal end of the colonoscope or gastroscope, flexible zone 12a will be rather fixed in the curvature of the colonoscope or the gastroscope and its surrounding curvature of the colon or upper intestinal tract, and deflectable zone 17 can deflect freely. This helps in only deflecting deflectable zone 17 when operating steering cables 90.

The intermediate tube element 88 has an inner surface and an outer surface and is shaped such that it defines longitudinal cable channels 96, 97 in the longitudinal direction of the tubular body 18. FIG. 5A-5C show six such cable channels 96 at the outside of intermediate tube element 88 and six such cable channels 97 at the inside of intermediate tube element 88. In the embodiment shown in FIG. 5A, each cable channel 96, 97 accommodates one steering cable 90. In one embodiment, all cable channels 96, 97 extend in a straight direction in parallel to the central axis 98. However, the cable channels 96, 97 may, alternatively spiral in the longitudinal direction of intermediate tube element 88. The spiral form may be such that a tangential location of a channel 96, 97 at the distal end and a tangential location of the same channel 96, 97 at the proximal end of the tubular body 18 are relatively shifted by a rotation angle of e.g. 90°, 180° or 270°. However, any other rotation angle can be implemented if desired.

Figure 19A:
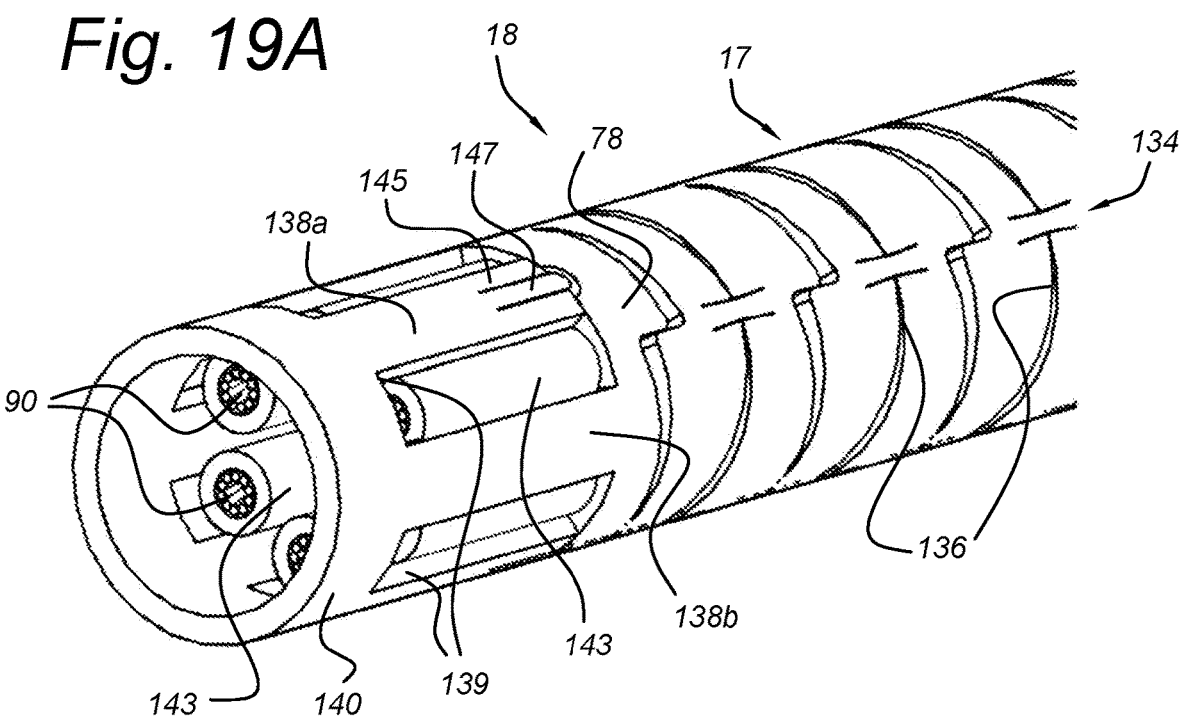
FIGS. 19A, 19B and 19C show an example of crimp bushings used to connect cables to the distal end of the tubular body.
Figure 19B:
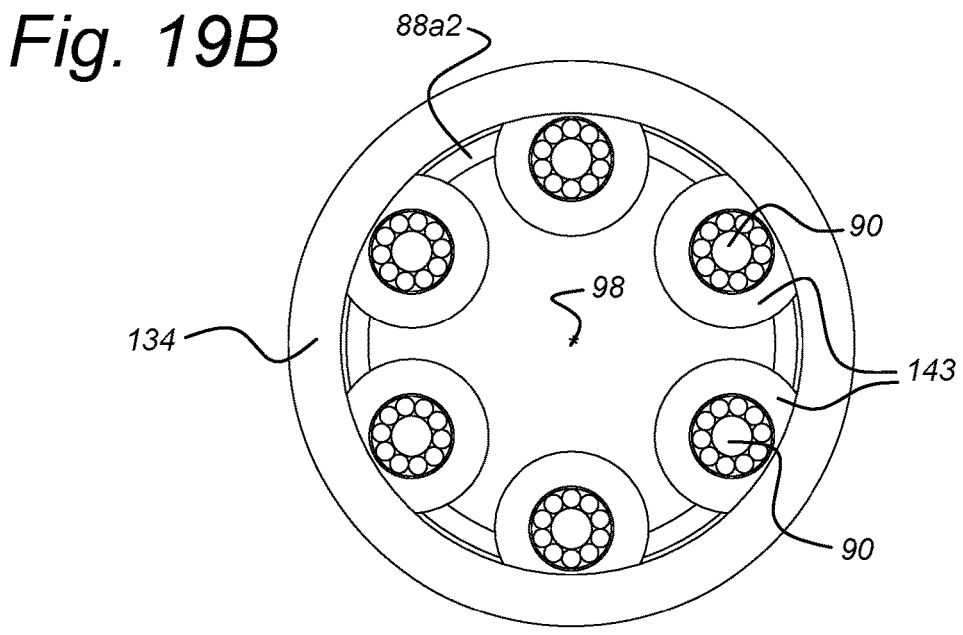

The tip of the outer tube element 86 comprises a plurality of longitudinal slots 80. In the embodiment shown there are six of them and they are equally spaced in the tangential direction. They are open towards the outer distal edge of the outer tube element 86. Between each two adjacent slots 80 there is a strip 84 at the most distal end of the outer tube element 86. So, in total there are six strips 84. Each slot 80 is aligned with one cable 90. These slots 80 are used for alignment with crimp bushings which are applied to clamp cables 90 at the distal end such that cables 90 cannot move in their cable channels in the proximal direction anymore at the most distal end. Such a connection with crimp bushings is shown in FIGS. 19A and 19B. Of course, any other known means of fastening the distal ends of the cables 90 to the tip of the tubular body 18 like welding or providing cables 90 with suitable beads may be used instead.

Each strip 84 is provided with a lip 82. Each lip 82 is aligned with an outside portion of the intermediate tube element 88 and serves as a laser welding portion of strip 84. Each lip 82 is laser welded to such outside portion of the intermediate tube element 88 such that, at the tip, the outer tube element 86 is firmly attached to the intermediate tube element 88. Thereby, intermediate tube element 88 and outer tube element 86 cannot rotate or move relative to one another at the distal end of the tubular body, thus, providing stability. Thus, at the distal end, cables 90 are blocked from tangential rotation relative to the outer tube element 86. This can, alternatively, be established by other features like laser welding without lips, or lips that are present in at least one of the intermediate tube element 88 and outer tube element 86 which are bent into a suitable aligned opening in the other one of these tube elements 86, 88. Gluing or brazing is also a possible option for attaching.

Located proximally from the slots 80 the outer tube element 86 comprises a deflectable section 72 aligned with deflectable zone 17. This deflectable section 72 is separated from the tip of the outer tube element 86 by a non-flexible section 78. Preferably section 78 is a ring shaped portion of the outer tube element 86 that has no, or hardly any holes or slots in it such that it cannot be bent. Section 78 is optional and can be left out.

In the embodiment shown in FIG. 5A, deflectable section 72 is implemented by laser cutting a predetermined pattern of slots in the material of the outer tube element 86. These slots extend through the whole thickness of the material. The slots are arranged such that the deflectable section 72 operates as a hinge and is optimized as to deflectability relative to the flexible zone 12a. Apart from that, deflectable section 72 should have a certain minimum rotational stiffness and minimum longitudinal stiffness. Preferably, the deflectable section 72 does not show any play in the longitudinal and tangential direction. However, for the deflectable section 72 this is not an absolute requirement. Any suitable slotted structure known from the prior art can be used to that effect. More details as to a preferred deflectable section 72 are shown in and explained with reference to FIG. 16A.

In the flexible zone 12a, outer tube element 86 has a flexible section 74. In a preferred implementation, the flexible section 74 is also implemented by laser cutting a predetermined pattern of slots in the material of the outer tube element 86. These slots extend through the whole thickness of the material. The slots are arranged such that the flexible section 74 is flexible to a certain predetermined extent but is optimized as to rotational stiffness. Again, this flexible section 74 should also have a certain minimum longitudinal stiffness. Preferably, the flexible section 74 does not show any play in the longitudinal and tangential direction. Any suitable slotted structure known from the prior art can be used to that effect. More details as to a preferred flexible section 74 are shown in and explained with reference to FIG. 16B.

In an embodiment, the flexibility of the flexible section 74 is less than the flexibility of the deflectable section 72.

Between deflectable section 72 and flexible section 74, outer tube element 86 may have a ring shaped, non-flexible section 76. So, preferably, ring-shaped section 76 has no, or hardly any holes or slots in it such that it cannot be bent. Ring-shaped section 76 is optional and can be left out.

At the proximal side of deflectable section 72, outer tube element 86 comprises a plurality of lips 75. Like lips 82 they are aligned with an outside portion of the intermediate tube element 88 and serve as laser welding portions. Each lip 75 is laser welded to such outside portion of the intermediate tube element 88 such that, at the proximal side of deflectable section 72, the outer tube element 86 is firmly attached to the intermediate tube element 88. Other mechanisms to connect outer tube element 86 to intermediate tube element 88 may be applied instead, like direct welding or using lips in one of the tube elements 86, 88 bent into aligned openings in the other one of the tube elements 86, 88. Gluing or brazing is also a possible option for attaching.

Also at locations along flexible zone 12a, outer tube element 86 may be attached to intermediate tube element 88, e.g. by laser welding suitable welding lips, shaped like lips 75, to outer portions of intermediate tube element 88 or using lips in one tube element bent into suitable aligned openings in the other tube element. Gluing or brazing is also a possible option for attaching. This provides the tubular body 18 with more stability and less risks of being deformed during use. In this way, intermediate tube element 88 cannot tangentially rotate relative to outer tube element 86 and functions even better as a tangential rotation blocker for cables 90.

The need to attach all applied tube elements 86, 88, 92 at several locations to one another along the entire length of the instruments increases the longer the instrument is. I.e., hinges at the same longitudinal locations in all applied tube elements 86, 88, 92 should be aligned at all times, both longitudinally and tangentially, in such longer instruments. The applied tube elements should, then, be free of rotation relative to one another as much as possible. For longer instruments it is also necessary to prevent the intermediate tube element 88 from being rotatable relative to the inner tube element 92 and/or outer tube element 86 (which ever one is applied) to prevent cables 90 from being rotated tangentially. If the applied tube elements would not be fixed in tangential rotation, a lot of slack and play may occur, resulting in instable controllability. Laser welding is, therefore, a preferred method because that results in zero play.

Outer tube element 86 has, preferably, a uniform thickness and is preferably made from a metal. Suitable materials are steel alloys like stainless steel, cobalt-chromium alloys, or a shape memory alloy such as Nitinol®. However, any other material that can meet the requirements as to rotational stiffness, longitudinal stiffness, play and manufacturability as regards the above explained slots/slotted structures can be selected too, like plastic, polymer, composites or other cutable material in which hinges can be made. Preferably, the material has an as low as possible friction coefficient relative to cables 90, a material like UHMWPE and/or Teflon™.

The thickness of outer tube element 86 depends on its application. For medical applications the thickness may be in a range of 0.02-2.0 mm, preferably 0.03-1.0 mm, more preferably 0.05-0.5 mm, and most preferably 0.08-0.4 mm. The diameter of the outer tube element 86 depends on its application. For medical applications the diameter may be in a range of 0.5-20 mm, preferably 0.5-10 mm, more preferably 0.5-6 mm.

The slots of the slotted structures 72, 74 in outer tube element 86 can be made by laser cutting. These slots which are made to just separate adjacent elements may have a width, preferably, in a range of 0-50 μm, more preferably 0-30 μm. Slots having a width of 0 μm or very close to that can be made by cutting a notch on locations where the slot should come, which notch does not extend through the whole thickness of the material but weakens the material to such an extent that one can easily break the material along the notch. Cutting such a notch can be done by laser engraving or by interruptions of the cutting path. This will be explained in more detail with reference to FIG. 19 hereinafter.

In the embodiment of FIGS. 5A-5C, the cross section of intermediate tube element 88 has a corrugated structure along its entire longitudinal direction. Here, the intermediate tube element 88 has a uniform thickness. So, also both its inner and outer surface have a corrugated structure.

The corrugated structure may be sine shaped and may be entirely symmetric. Here, the term "sine shaped" is used to refer to a shape that looks like a sine but is not really an ideal sine. The corrugated structure has a plurality of outer peaks 100. In the embodiment shown there are six outer peaks 100. They are all located at the same radial distance from the central axis 98 and may touch the inside of outer tube element 86. Lips 75 and 82 of outer tube element 86 are attached to intermediate tube element 88 at such outer peaks 100. Outer tube element 86 may also be attached to intermediate tube element 88 at locations in flexible zone 12a, e.g. by means of laser welding suitable welding lips in outer tube element 86 which are aligned with outer peaks 100.

When a connection between outer tube element 86 and intermediate element 88 is made by means of lips and suitable aligned openings, as referred to above, such lips are preferably made in outer tube element 86 and such openings in intermediate element 88. The openings are then located at such peaks 100. Gluing or brazing is also a possible option for attaching.

The corrugated structure also has a plurality of inner peaks 102. In the embodiment shown there are six inner peaks 102. They are all located at the same radial distance from the central axis 98 and may touch the outside of inner tube element 92. Preferably, one or more of those inner peaks 102 are attached to inner tube element 92 somewhere in the tip, e.g. at the same distance from the distal edge as the lips 82. When the inner tube element 92 and intermediate tube element 88 are both made from a metal, such an attachment may be implemented by laser welding. However, any other suitable attachment technique may be used instead, like gluing or brazing or lips in one of the tube elements and suitable aligned openings in the other tube element as referred to above. As explained above, such connections/attachments between adjacent tube elements may be present along the entire length of the instrument.

The corrugated structure of intermediate tube element 88 is the same along its entire length and defines longitudinal channels extending from the distal end to the proximal end of the tubular body 18 for accommodating cables 90. The corrugated structure has a plurality of outward facing cable channels 96 and a plurality of inward facing cable channels 97. Here, there are six cable channels 96 and six cable channels 97. However, any other number may be used instead. At least three such cable channels 96, 97 are necessary to accommodate three steering cables 90 to allow for a deflection of the deflectable zone 17 in all directions. All cable channels 96, 97 are preferably equally spaced in the tangential direction.

The corrugated structure may spiral in the longitudinal direction such that it defines spiraling cable channels 96, 97.

Figure 7A:
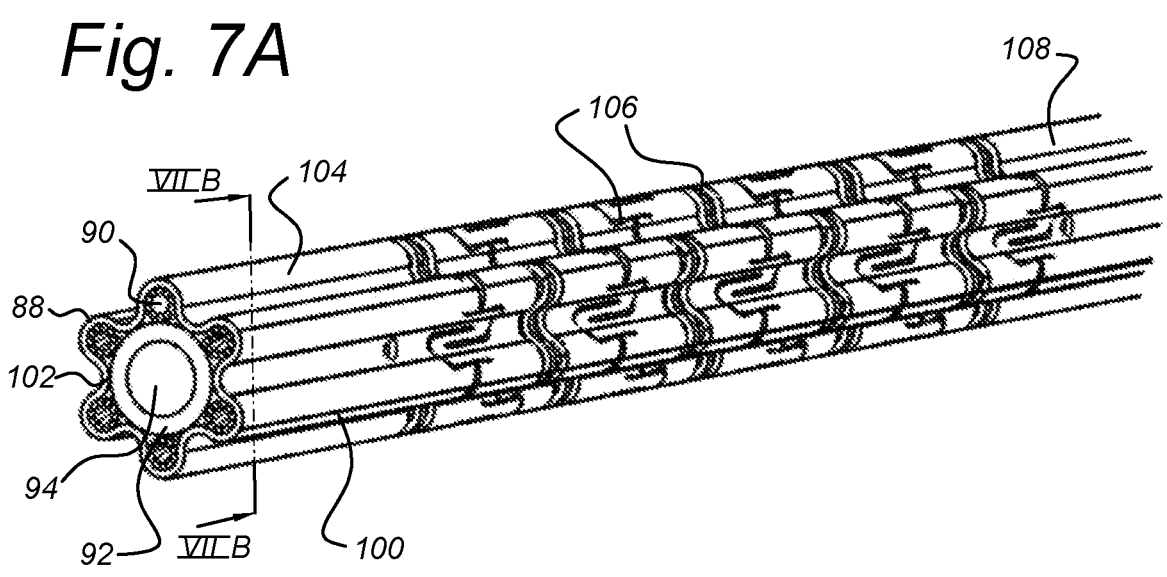

Intermediate tube element 88 is provided with a deflectable section in deflectable zone 17 and a flexible section in flexible zone 12a. Any suitable technical implementation can be used. E.g., slotted structures like the ones shown at 72 and 74 in the outer tube element 86 can be used. An alternative slotted structure 106 is shown in corrugated intermediate tube element 88 shown in FIG. 7A. The example slotted structure 106 of FIG. 7A is shown in more detail in FIG. 16C. as a further alternative, any of the slotted structures shown in detail in FIGS. 16A-16C can be used in the deflectable section of the intermediate cylindrical section 88 whereas the rest of the structure of intermediate tube element 88 is flexible, such that it bends easy enough for a certain envisaged application, like colonoscopy.

Intermediate tube element 88 has, preferably, a uniform thickness and is preferably made from a metal. Suitable materials are steel alloys like stainless steel, cobalt-chromium or a shape memory alloy such as Nitinol®. However, any other material that can meet the requirements as to rotational stiffness, longitudinal stiffness, play and manufacturability as regards the above explained slots/slotted structures can be selected too, like plastic, polymer, composites or other cutable material in which hinges can be made. Preferably, the material has an as low as possible friction coefficient relative to cables 90. like UHMWPE and/or Teflon™ may be used. Intermediate tube element 88 can be made by shaping an originally cylindrical tube with circular cross section into the desired form.

The thickness of intermediate tube element 88 depends on its application. For medical applications the thickness may be in a range of 0.02-2.0 mm, preferably 0.03-1.0 mm, more preferably 0.05-0.5 mm, and most preferably 0.08-0.4 mm. The inner and outer diameters of the intermediate tube element 88, as defined by its internal peaks 102 and outer peaks 100, depend on its application. For medical applications the inner and outer diameters may be in a range of 0.5-20 mm, preferably 0.5-10 mm, more preferably 0.5-6 mm. The outer diameter of intermediate tube element 88 is selected such that it is substantially the same as the inner diameter of outer tube element 86. Then, outer tube element 86 touches intermediate tube element 88 at its outer peaks 100. Similarly, the inner diameter of intermediate tube element 88 is selected such that it is substantially the same as the outer diameter of inner tube element 92. Then, inner tube element 92 touches intermediate tube element 88 at its internal peaks 102.

Even though the intermediate tube element 88 has a corrugated cross section, experiments have shown that the slots of the slotted structure 106 in intermediate tube element 88 can be made by laser cutting with a laser beam. Such a laser beam may be directed perpendicular to the central axis 98. However, it is also possible to direct such a laser beam such that it is located in a plane perpendicular to the central axis 98 and substantially perpendicular to the outer surface of intermediate tube 88. Here "substantially" means within +/−10% of an angle of 90°. These slots which are made to just separate adjacent elements may have a width, preferably, in a range of 0-50 μm, more preferably 0-30 μm.

Cables 90 are selected such that their diameter is slightly less than the height of channels 96, 97, where the height of the channels 96, 97 is defined as their cross section width in the radial direction. Suitable cable diameters are within a range of, for instance, 0.1 to 1.0 mm. The cross section width of channels 96, 97 should be larger than the cable diameter at any location of channels 96, 97. Then, cables 90 can move in channels 96, 97 in the longitudinal direction substantially without any friction. Only in bent portions of the tubular body 18 some of the cables 90 will experience friction, as will be addressed later on.

The cables 90 should be selected such as to have an as high as possible tensile strength in combination with an as low as possible bending stiffness and as high as possible longitudinal stiffness. Therefore, preferably, the cables 90 are made from several twisted metal wires instead of a solid single wire. Alternatively, materials like Kevlar™, aramid or dyneema can be used. Such cables can contain several twisted wires and may have a circular cross section, or even an oval or flat cross section.

Because the corrugated structure of intermediate tube element 88 is, by nature, difficult to deform by an external mechanical force, both in the radial and tangential direction, it will function as walls of channels 96, 97 that are difficult to be deformed. This assists significantly in keeping the entire tubular body 18 in its original shape as much as possible even when it has a length of 1 meter or more and is inserted into a curved duct like a human colon, and is rotated by the surgeon at the proximal end to bring the tool at the distal end in a desired orientation.

Inner tube element 92 has an internal channel 94. The cross section dimensions of internal channel 94 are such as to be suitable for the intended purpose. In many applications, the internal channel 94 accommodates an actuation cable 184 (cf. FIG. 15B) that may be thicker and stronger than steering cables 90. Such an actuation cable 184 is, at its proximal end, connected to the handle 3 and operated by the grips of handle 3. I.e., moving the grips towards and away from one another results in longitudinal movement of the actuation cable which can be transformed into an opening and closing movement of a pair of scissors or the jaws of a clamping device. Such techniques are widely known to persons skilled in the art and need no further explanation here.

Channel 94 may accommodate one or more electrically conductive or optical wires. Such electrical or optical wires may transport electrical or optical energy to a tool using that energy to perform a predetermined function like heating, burning, lighting, sensing (looking), etc.

Inner tube element 92 has, preferably, a uniform thickness and needs to be flexible at least in the deflectable zone 17 and flexible zone 12a. Thus, tube element 92 can be entirely flexible along its entire length. It can, e.g. be made of a spring or coil. Alternatively it can be made of a flexible material like plastic. As a further alternative, it can be made of a metal of which the flexibility is, e.g., increased in the deflectable zone 17 and flexible zone 12a by suitable slotted structures as known from the prior art or as explained with reference to FIGS. 16A-16C hereinafter.

Suitable materials for inner tube element 92 are steel alloys like stainless steel, cobalt-chromium alloysor a shape memory alloy such as Nitinol®. However, any other material that can meet the requirements as to rotational stiffness, longitudinal stiffness, and play and manufacturability as regards the above explained slots/slotted structures can be selected too, like plastic, polymer, composites or other cutable material in which hinges can be made. Preferably, the material has an as low as possible friction coefficient relative to cables 90, a material like UHMWPE and/or Teflon™.

The thickness of inner tube element 92 depends on its application. For medical applications the thickness may be in a range of 0.03-2.0 mm, preferably 0.03-1.0 mm, more preferably 0.05-0.5 mm, and most preferably 0.08-0.4 mm. The diameter of the inner tube element depends on its application. For medical applications the diameter may be in a range of 0.5-20 mm, preferably 0.5-10 mm, more preferably 0.5-6 mm. The outer diameter of inner tube element 92 is selected such that it is substantially the same as the inner diameter of intermediate tube element 88 as defined by its internal peaks 102. Then, inner tube element 92 touches intermediate tube element 88 at its internal peaks 102.

Slots of slotted structures in inner tube element 92, if applied, can be made by laser cutting. These slots which are made to just separate adjacent elements may have a width, preferably, in a range of 0-50 μm, more preferably 0-30 μm.

To provide the tubular body 18 with enough rotational stiffness and longitudinal stiffness, at least one of outer tube element 86, intermediate tube element 88 and inner tube element 92 is made from a metal like steel alloy, cobalt-chromium alloy and Nitinol®.

Figures 6A, 6B, 6C:
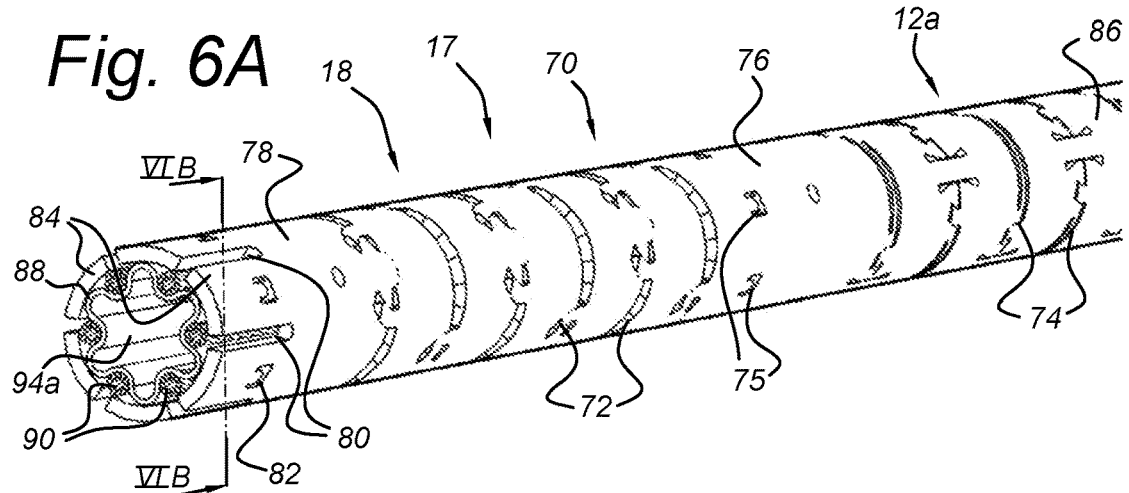

FIGS. 6A, 6B, 6C show an embodiment in which only the outside cable channels 96 are accommodating cables 90. So, the inside channels 97 are empty or and designed to contain electrical wires, optical fibres or wires for some kind of mechanical actuation. Thus, in the embodiment of FIGS. 6A, 6B, 6C no inner tube element 92 is needed for keeping cables 90 in place. For the rest all elements are the same as in the embodiment of FIGS. 5A, 5B, 5C. They are indicated with the same reference signs.

To provide the tubular body 18 with enough rotational stiffness and longitudinal stiffness, here, at least one of outer tube element 86 and intermediate tube element 88 is made from a metal like steel alloy, cobalt-chromium alloy and Nitinol®.

Figure 7B:
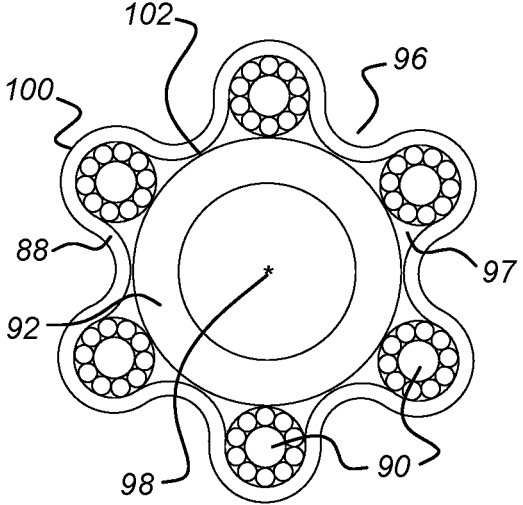
Figure 7C:
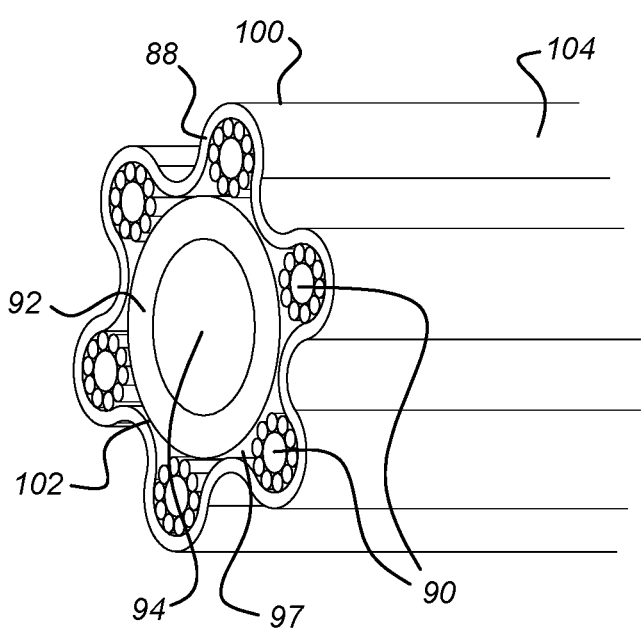

FIGS. 7A, 7B, 7C show an embodiment in which the outer channels 96 are empty and do not accommodate cables 90. They may contain electrical wires, optical fibres or wires for some kind of mechanical actuation. So, the embodiment of FIGS. 7A, 7B, 7C does not need outer tube element 86 for keeping cables 90 in place. For the rest all elements are the same as in the embodiment of FIGS. 5A, 5B, 5C. They are indicated with the same reference signs.

Thus, in FIG. 7A, one can clearly see the outside of intermediate tube element 88 (note that this is the same intermediate tube element 88 of FIGS. 5A-5C and 6A-6C). Intermediate tube element 88 has a tip section 104 at the distal end. Proximally from the tip section 104, intermediate tube element 88 has a deflectable section, here implemented as a hinge structure 106 which is aligned with deflectable zone 17. Proximally from the hinge structure 106, the intermediate tube element 88 has an intermediate section 108.

Crimp bushings or laser welded bushings may be provided to connect cables 90 to the tip section.

In the shown embodiment, the hinge structure 106 is made by a slotted structure comprising a plurality of slots. The hinge structure 106 may be manufactured by laser cutting a predetermined pattern of slots in the material of the intermediate tube element 88. These slots extend through the whole thickness of the material. The slots are arranged such that the hinge structure 106 is optimized as to deflectability relative to the flexible zone 108. Apart from that, deflectable section should have a certain minimum rotational stiffness and minimum longitudinal stiffness. Preferably, the hinge structure 106 does not show any play in the longitudinal and tangential direction. However, for the hinge structure 106 this is not an absolute requirement. Any suitable slotted structure known from the prior art can be used to that effect. More details as to a preferred hinge structure 106 are shown in and explained with reference to FIG. 16C.

The intermediate section 108 is aligned with flexible zone 12a and should be flexible. So, it should be either made of a flexible material or made flexible, e.g., by providing this intermediate section 108 with a suitable slotted structure. Any suitable slotted structure known from the prior art may be used. Advantageously, a slotted structure is used as shown in and explained with reference to FIG. 16C.

In an embodiment, deflectable section 106 is more flexible than intermediate section 108.

The structures shown in FIGS. 5A-5C, 6A-6C, and 7A-7C may suffer from cables 90 getting stuck because of a wedge effect in bent or deflected portions of the tubular body 18. This will be explained in more detail with reference to FIGS. 17A and 17B now.

Figure 17A:
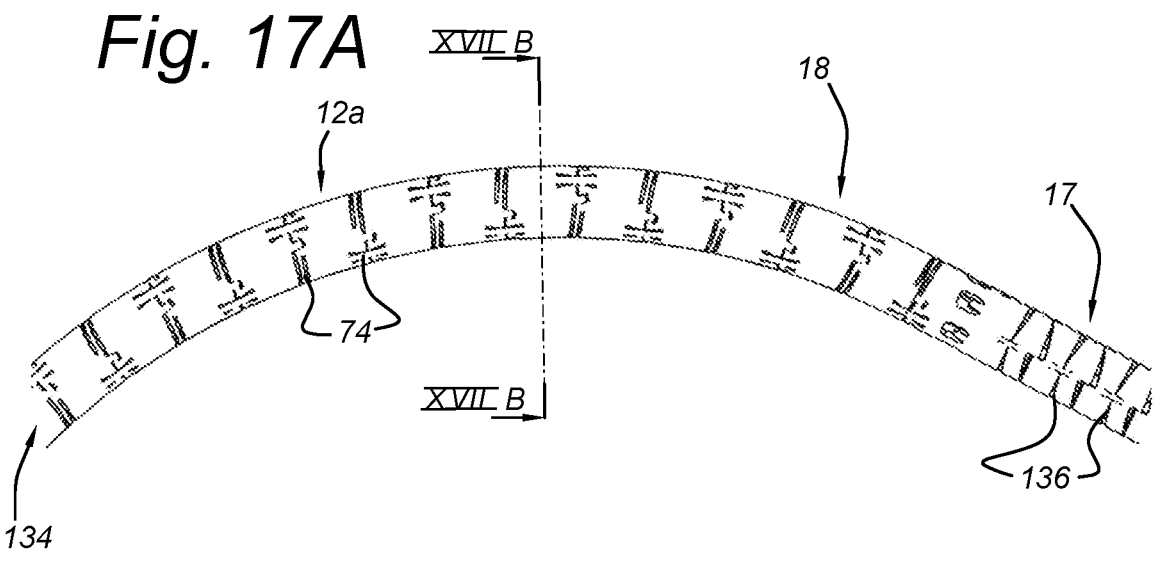
FIG. 17A shows a deflectable zone of a tubular body in a deflected position.
Figure 17B:
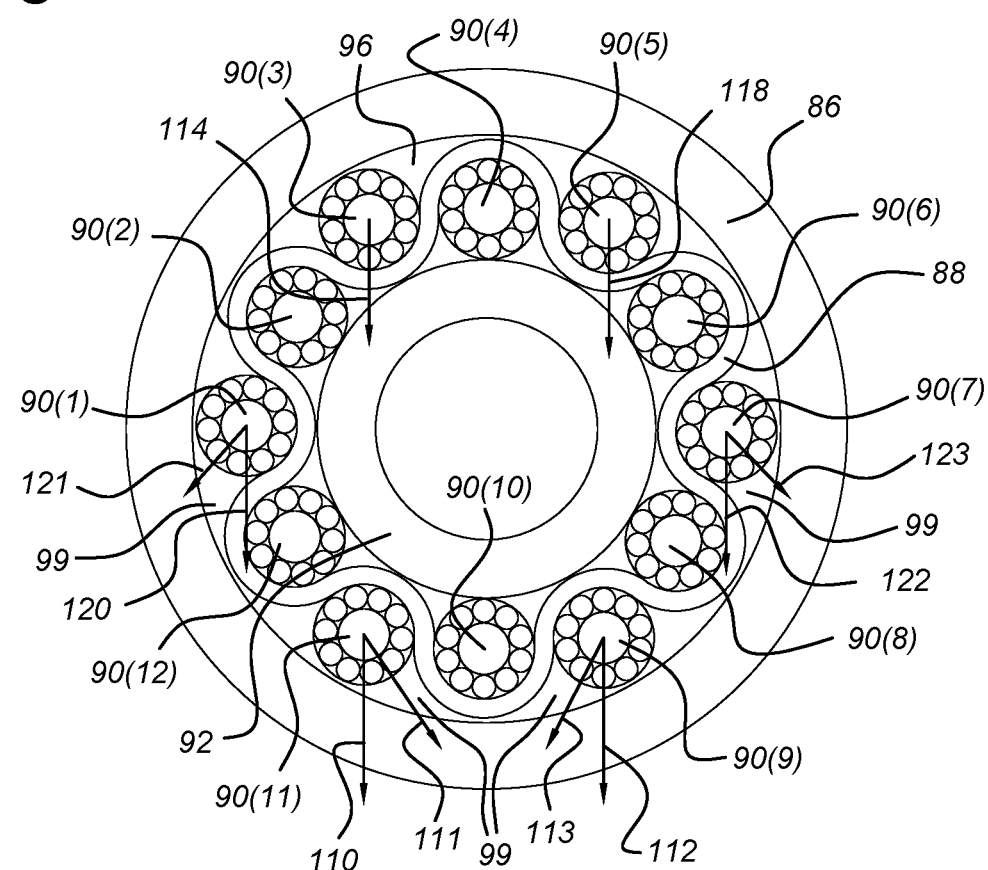
FIG. 17B shows a cross section through such deflected tubular body at a position indicated by arrows XVIIB.

FIG. 17A shows bendable zone 12 of tubular body 18 in a bent position. The tubular body 18 is one as explained in further detail in FIGS. 9A, 9B (and viewed from the opposite side). FIG. 17B shows a cross section through such bent tubular body 18 at a position indicated by arrows XVIIB.

It is assumed that in the case of FIG. 17A the tip of the deflectable end 17 is desired to be deflected downward, as seen in the plane of the drawing. This is done by exerting a pulling force on cables 90 located in the lower portion of intermediate tube element 88 as seen in the surface of the drawing and relaxing or pushing the cables 90 in the upper portion of intermediate tube element 88 as seen in the surface of the drawing. Stated differently, the lower located cables 90 are pulled towards the left from the proximal end in the surface of the drawing of FIG. 17A and the upper located cables 90 are relaxed from the proximal end such that they can move in the right direction.

Because of the bent status at the cross section location of FIG. 17B, this will cause downward directed forces 110, 112, 120, 123, 114, 118 on cables 90 as shown in FIG. 17B (here only the forces on the cables located in outer channels 96 are shown). The closer cable 90 is located at the downside of the bent tubular body 18 the greater downward directed force 110, 112, 120, 123, 114, 118 on cable 90 will be. Channels 96 are not circular but are tapering from their central axis, which substantially coincides with a central axis of a cable 90, towards an area of contact between intermediate tube element 88 and outer tube element 86. At the lower side and middle side of the tubular body 18, the exerted forces 110, 112, 120, and 122, respectively, have components 111, 113, 121, and 123, respectively, directed towards tapered sections 99 of the channels 96 such that a "wedge" effect occurs and there is a risk the cables 90 get clamped, which results in longitudinal friction on the cables 90, or even get stuck between intermediate tube element 88 and outer tube element 86. For shorter tubular bodies 18 and relatively small forces exerted on the cables 90, this may not be serious but for longer instruments which are already curved at many locations in use, like in colonoscopy, this increase in friction on the cables 90 may become more serious and prevent proper deflectability of the deflectable zone 17.

As may be evident to persons skilled in the art this effect may also occur in the deflectable zone 17 itself.

Figure 7D:
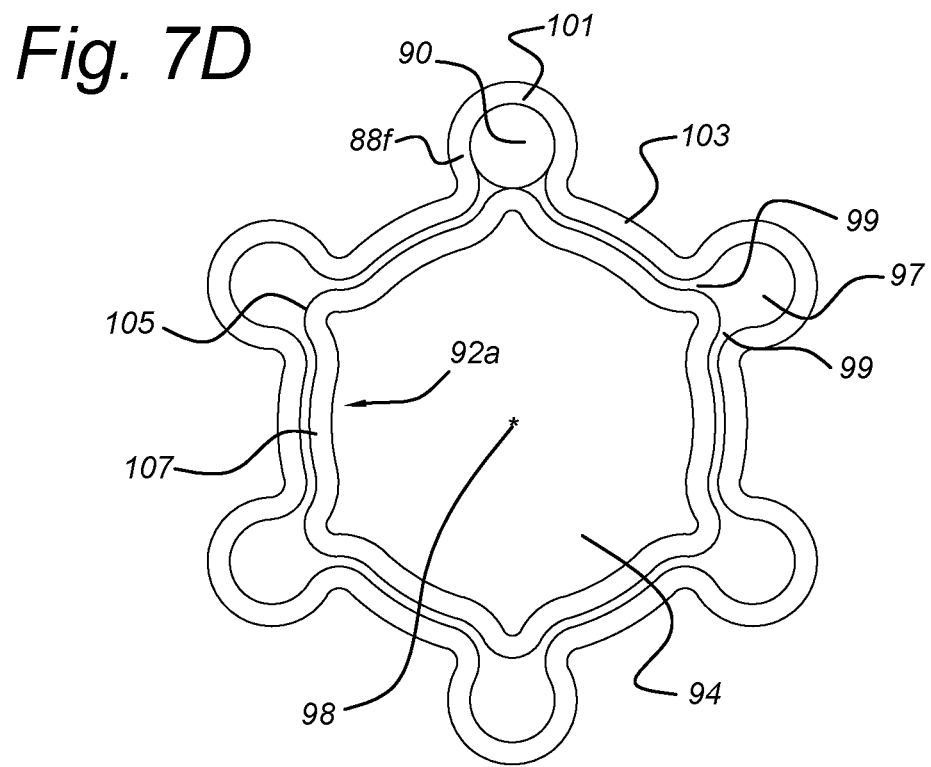

Several embodiments of the present invention solve this issue. One such solution is schematically shown in FIG. 7D which shows a variant of the embodiment of FIGS. 7A-7C. FIG. 7D shows an intermediate tube element 88f shaped such that it defines inwardly directed cable channels 97. Each cable channel 97 is partly surrounded by a cable tube portion 101. Each two adjacent cable tube portions 101 are mutually connected via intermediate tube element portions 103 all located on a same circle about central axis 98.

An inner tube element 92a is provided inside intermediate tube element 88f. Inner tube element 88f is provided with a plurality of rims 105, one rim 105 per cable channel 97. Each rim 105 extends to a certain predetermined extent in an open portion of one cable channel 97 facing towards central axis 98. Moreover, each rim 105 extends along the entire length of inner tube element 92a. Each two adjacent rims 105 are mutually connected via inner tube element portions 107 all located on a same circle about central axis 98, such that intermediate tube element portions 103 are aligned with inner tube element portions 107 such that one intermediate tube element portion 103 touches one inner tube element portion 107.

There may be small tapered sections 99 of cable channel 97 between inner tube element 92a and intermediate tube element 88f, as indicated in FIG. 7D. However, because rims 105 extend slightly into channels 97 and support cables 90, risks for cables 90 to get stuck in these tapered sections 99 are reduced.

As a further alternative, inner tube element 92 may be provided with a plurality of longitudinal rims, two per cable 90. Each one of such rims extend outwardly from the outer surface of inner tube element 92 and are aligned with one tapered section 99 along the entire length of tubular body 18. So, each cable 90 is, then, supported by two such rims.

For the rest, the same properties may apply to inner tube element 92a as to inner tube element 92.

Another solution may be providing extra tubes in channels 96, 97, e.g. extra tubes 166 as shown in and explained hereinafter with reference to FIGS. 14A, 14B.

To provide the tubular body 18 with enough rotational stiffness and longitudinal stiffness, at least one of intermediate tube element 88 and inner tube element 92/92a is made from a metal like steel alloy, cobalt-chromium alloy and Nitinol®.

Another solution is shown in FIGS. 8A, 8B, 8C. FIG. 8B is a cross section at a location indicated with arrows VIIIB, and FIG. 8C is an enlarged view of the tip section of the tubular body 18. Here, the tubular body 18 comprises an outer tube element 130 and an intermediate tube element 88a. No inner tube element is provided. Instead of intermediate tube element 88a, alternatively, intermediate tube element 88 may be used or another suitable form.

The outer tube element 130 is shaped such as to have a plurality of internal channels 132 for accommodating cables 90. Preferably these channels 132 have a circular cross section, like cables 90. FIG. 8C shows these channels 132 without the cables 90. The channels 132 are completely surrounded by the material of the outer tube element 130. Again, the channels 132 may have a spiral form in the longitudinal direction of the tubular body 18. In this embodiment, all cables 90 are enclosed entirely in their radial direction by channels 132. So, if, as caused by an increased tension of cables 90 in a deflected zone 17 of the tubular body 18, cables 90 will experience radial forces as seen from their own central axis, they will not experience increased friction or get stuck in tapered portions of the channels 132 because of a wedge effect but will always remain fully supported by channels 132.

An alternative outer tube element 130 may be designed such that it defines an open channel 132 towards central axis 98. These channels 132 together with the inner surfaces of the inner U-shaped portions 88*a*1 define channels for accommodating cables 90. Stated differently, then, outer tube element 130 is provided with a plurality of rims, two per cable 90, and aligned with the channels 132. Each pair of such rims then supports one cable 90 at both sides along their entire length.

Cables 90 can be fixed to outer tube element in ways known from the prior art, e.g. by providing their most distal ends with a thicker section which is much thicker than the channel cross section. This can e.g. be done by clamping a bead like element or crimp bushings on the most distal end of the cables 90 which remains clamped after the clamping action.

Intermediate tube element 88*a* has a corrugated cross section. In the embodiment shown, it has six outer portions 88*a*2 designed such that they are arranged on a circle and six inner portions 88*a*1 having a U-shape. Any other number than six may be applied to. Each U-shaped inner portion 88*a*1 connects two adjacent outer portions 88*a*2. The inner side of outer tube element 130 is shaped to match the outer surface of intermediate tube element 88*a*. Channels 132 are located in inwardly extending portions of outer tube element 130 which are at least partly arranged within the U-shaped inner portions 88*a*1 of intermediate tube element 88*a*. By this corrugated structure, intermediate tube element 88*a* supports outer tube element 130 and counteracts deformation of outer tube element 130 by radial forces (caused by bending of the tubular body 18) or tangential forces (caused, e.g., by rotating the tubular body 18 at the proximal end in use). Thus, even when the tubular body 18 is bent and rotated it will keep its original cross section shape as much as possible and so do channels 132. Consequently, cables 90 do not get stuck in use.

Outer tube element 130 is preferably made from a flexible plastic, like polymer, that shows a predetermined rotational stiffness, longitudinal stiffness, and manufacturability. Such a tube element can be designed flexible and yet rigid enough such that it can be deflected in deflectable zone 17 and is flexible in flexible zone 12*a*. It can be made by extrusion, 3D printing, etc. Preferably, the material has an as low as possible friction coefficient relative to cables 90, a material like UHMWPE and/or Teflon™

The thickness of outer tube element 130 depends on its application. For medical applications the thickness may be in a range of 0.02-2.0 mm, preferably 0.03-1.0 mm, more preferably 0.05-0.5 mm, and most preferably 0.08-0.4 mm. The inner and outer diameters of the outer tube element 130 depend on its application. For medical applications the inner and outer diameters may be in a range of 0.5-20 mm, preferably 0.5-10 mm, more preferably 0.5-6 mm. The thickness of outer tube element 130 at locations between channels 132 may be in a range of 0.02-2.0 mm, preferably 0.03-1.0 mm, more preferably 0.05-0.5 mm, and most preferably 0.08-0.4 mm. The thickness of outer tube element 130 at locations including channels 132 may be 0.1 mm.

Channels 132 have a diameter slightly larger than cables 90, so, for instance, in a range of 0.1 mm 1.0 mm.

Intermediate tube element 88*a* is provided with a deflectable section in deflectable zone 17 and a flexible section in flexible zone 12*a*. Any suitable technical implementation can be used. E.g., slotted structures like the ones shown at 72 and 74 in the outer tube element 86 of the embodiment of FIGS. 5A-5C or 6A-6C can be used. Alternatively, the slotted structure 106 as shown in corrugated intermediate tube element 88 of FIG. 7A can be used. A possible implementation is shown in FIGS. 14A, 14B.

Intermediate tube element 88*a* has, preferably, a uniform thickness and is made from a metal to meet the requirements as to rotational stiffness, longitudinal stiffness, play and manufacturability of the tubular body 18. Suitable materials are steel alloys like stainless steel, cobalt-chromium alloys or a shape memory alloy such as Nitinol®. Intermediate tube element 88*a* can be made by shaping an originally cylindrical tube with circular cross section into the desired form. Preferably, the material has an as low as possible friction coefficient relative to cables 90.

The thickness of intermediate tube element 88*a* depends on its application. For medical applications the thickness may be in a range of 0.02-2.0 mm, preferably 0.03-1.0 mm, more preferably 0.05-0.5 mm, and most preferably 0.08-0.4 mm. The inner and outer diameters, respectively, of the intermediate tube element 88*a*, as defined by most inner points of the U-shaped inner portion 88*a*1 and outer portion 88*a*2, respectively, depend on its application. For medical applications the inner and outer diameters may be in a range of 0.5-20 mm, preferably 0.5-10 mm, more preferably 0.5-6 mm.

Even though the intermediate tube element 88*a* has a corrugated cross section, experiments have shown that the slots of the slotted structure 106 in intermediate tube element 88*a* can be made by laser cutting with a laser beam which may be directed in a plane perpendicular to the central axis 98 and either perpendicular to the central axis 98 or perpendicular to the outside surface of intermediate tube element 88*a*. These slots which are made to just separate adjacent elements may have a width, preferably, in a range of 0-50 μm, more preferably 0-30 μm.

Also here cables 90 may have a thickness of 0.1 to 1.0 mm.

Figure 9A:
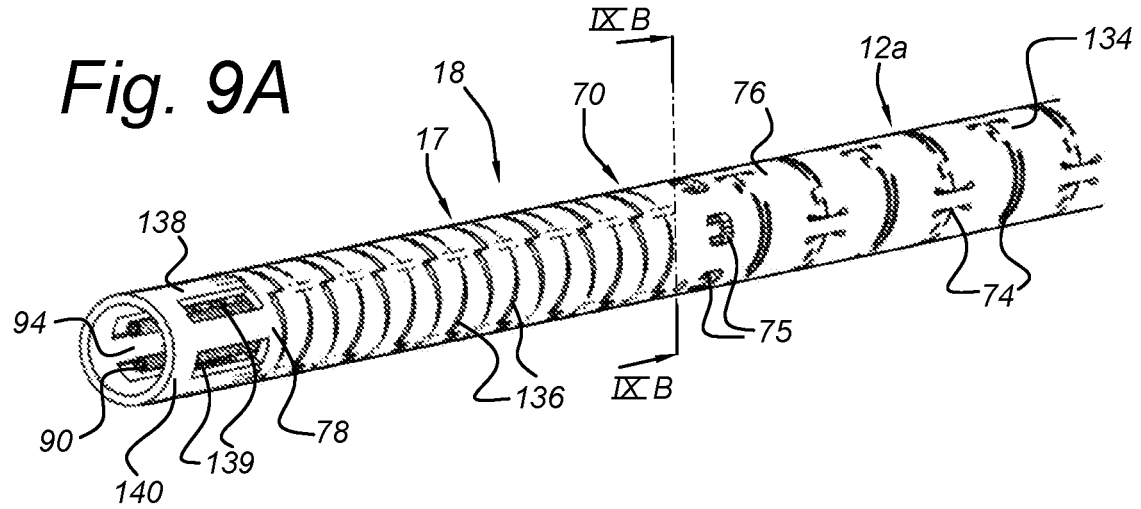
FIGS. 9A, 9B show a hollow tube having a specially shaped liner with cable channels for steering cables.
Figure 9B:
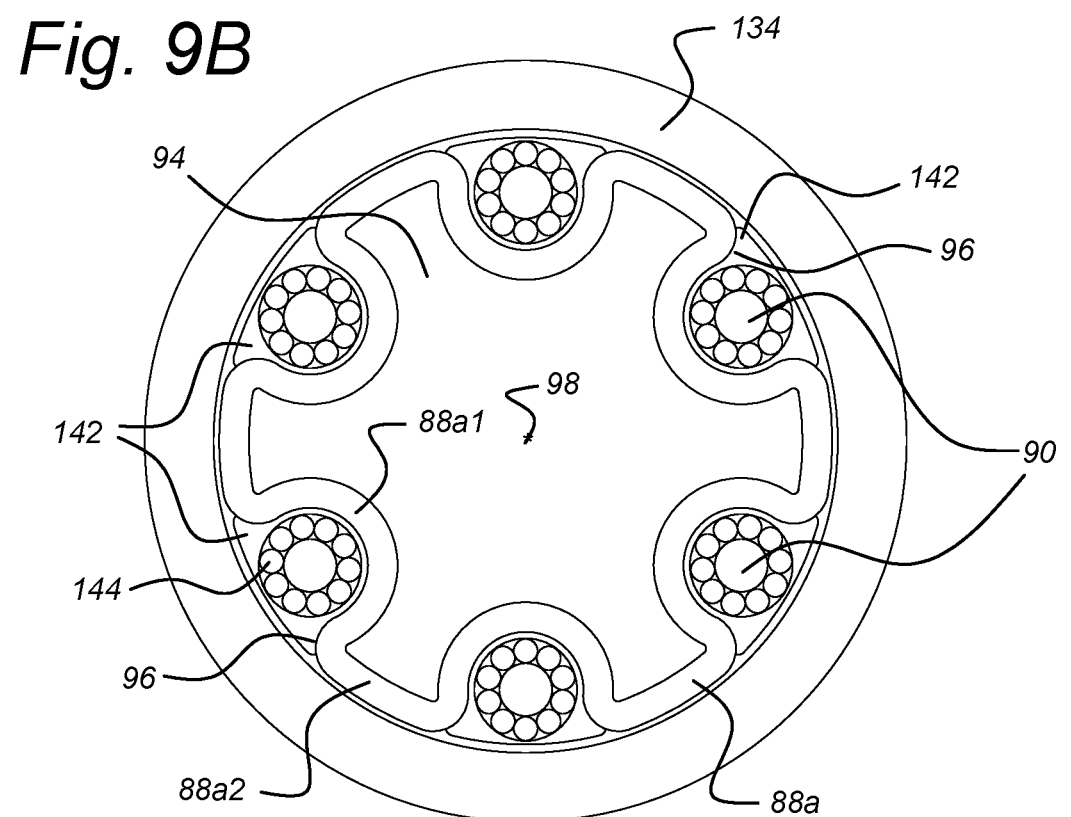

The embodiment shown in FIGS. 9A and 9B is an alternative to the one of FIGS. 8A-8C. FIG. 9B is a cross section view as defined by arrows IXB in FIG. 9A. Here, the tubular body 18 comprises an outer tube element 134 that has a uniform thickness. Outer tube element 134 encloses intermediate tube element 88*a*. Instead of intermediate tube element 88*a*, alternatively, intermediate tube element 88 may be used or another suitable form.

Outer tube element 134 may be made from any suitable material as long as it meets the requirements as to rotational stiffness, longitudinal stiffness, and manufacturability, as well as deflectability in deflectable zone 17 and flexibility in flexible zone 12*a*.

In the embodiment shown in FIGS. 9A and 9B outer tube element 134 is similar to the outer tube element 86 of FIGS. 5A-5C. However, one can use the same outer tube element as shown in FIGS. 5A-5C, or 6A-6C or 8A-8C instead.

Figure 16A:
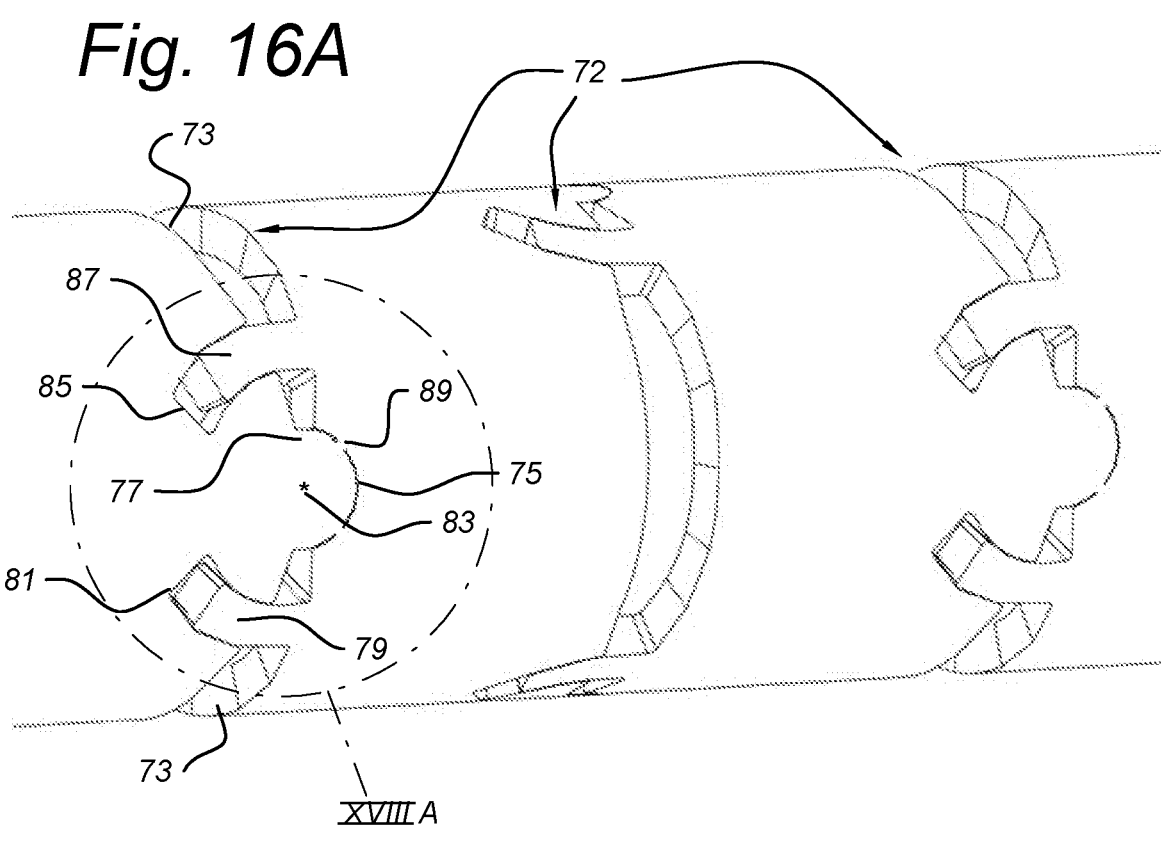
FIGS. 16A-16H show some alternative slotted structures that can be used in flexible and deflectable sections of the instrument.
Figure 16B:
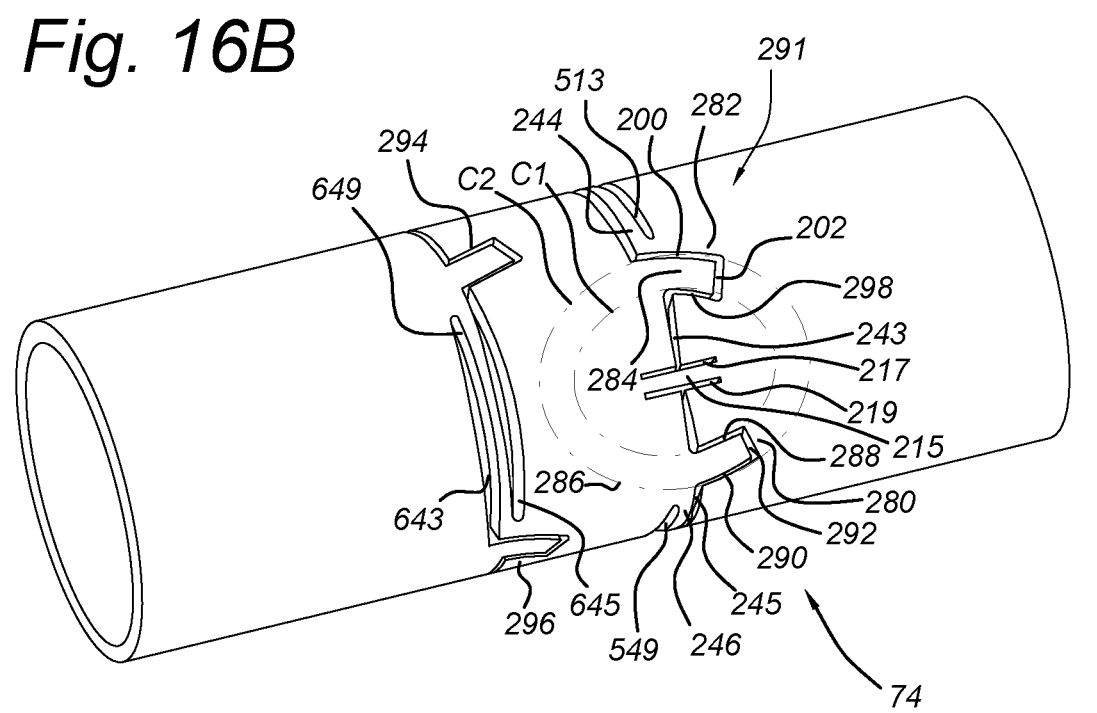

In flexible zone 12*a*, outer tube element 134 has a flexible section 74 with the same slotted structure as shown in FIG. 5A (cf. also FIG. 16B). Other slotted structures can be used instead.

Figure 16C:
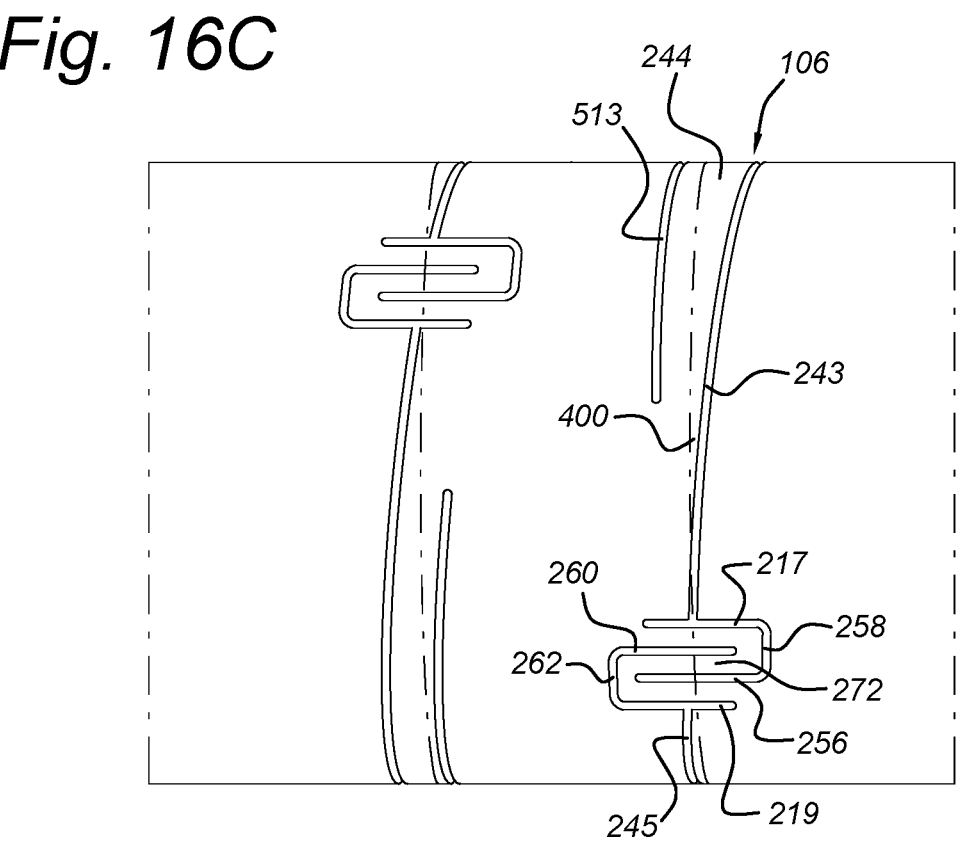
Figure 16D:
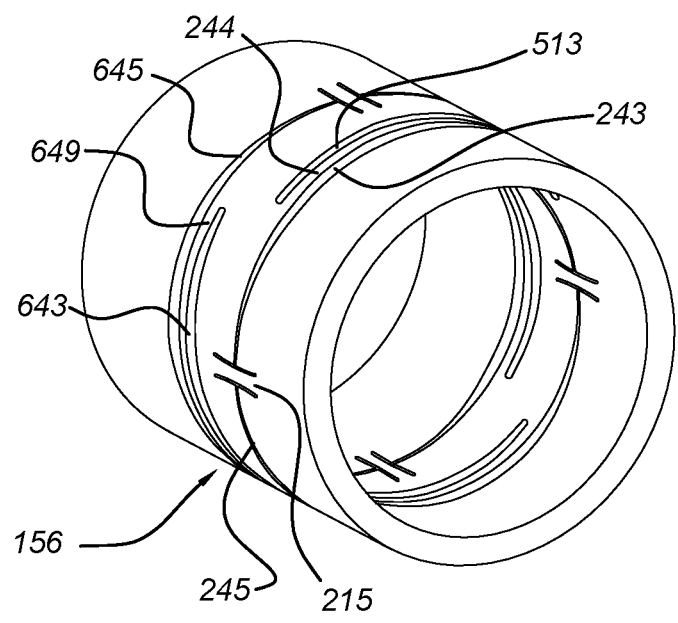

In deflectable zone 17, outer tube element 134 has a deflectable section 72 with a slotted structure as shown in more detail in FIG. 16D. Other slotted structures can be used instead.

In the tip section, distal to deflectable zone 17, outer tube element 134 comprises non-flexible section 78 which is preferably a ring shaped portion of outer tube element 134 that has no, or hardly any holes or slots in it such that it cannot be bent. Distal from non-flexible section 78 and connected/attached to it, outer tube element 134 is provided with strips 138 defining slots 139 between them. At their distal ends, the strips 138 are all connected/attached to a non-flexible section 140 which is preferably also a ring shaped portion of outer tube element 134 that has no, or hardly any holes or slots in it such that it cannot be bent. Preferably, there are as many strips 138 as there are outer portions 88a2 of intermediate tube element 88a. And, preferably, each strip 138 is attached or connected to one such outer portion 88a2, e.g., by laser welding, gluing or brazing or a bent lip/opening connection.

Outer tube element 134 is also attached to intermediate tube element 88a at welding lips 75. Each welding lip 75 is welded to one outer portion 88a2 of intermediate tube element 88a. Also at other locations along flexible zone 12a, outer tube element 134 may be attached to intermediate tube element 88a, e.g. by gluing or brazing, or laser welding suitable welding lips to outer portions 88a2, or bent lip/opening connections.

Outer tube element 134 is preferably made from a metal. Suitable materials are steel alloys like stainless steel, cobalt-chromium alloys, or a shape memory alloy such as Nitinol®. However, any other material that can meet the requirements as to rotational stiffness, longitudinal stiffness, play and manufacturability as regards the above explained slots/slotted structures can be selected too, like plastic, polymer, composites or other cutable material in which hinges can be made.

The thickness of outer tube element 134, which is preferably uniform, depends on its application. For medical applications the thickness may be in a range of 0.02-2.0 mm, preferably 0.03-1.0 mm, more preferably 0.05-0.5 mm, and most preferably 0.08-0.4 mm. The diameter of the outer tube element 134 depends on its application. For medical applications the diameter may be in a range of 0.5-20 mm, preferably 0.5-10 mm, more preferably 0.5-6 mm.

The slots of the slotted structures 72, 74 in outer tube element 134 can be made by laser cutting. These slots which are made to just separate adjacent elements may have a width, preferably, in a range of 0-50 µm, more preferably 0-30 µm.

Inner U-shaped portions 88a1 enclose channels 96 (cf. also FIG. 5B). Again, these channels 96 may be straight or spiraled in the longitudinal direction of tubular body 18. In this embodiment, each channel 96 accommodates a liner 142. The outer surface of liner 142 has a first portion directed outwardly as seen from central axis 98 which has a shape matching the inside surface of outer tube element 134. So, the first portion has the form of a portion of a circle. The outer surface of liner 142 has a second portion directed inwardly as seen from central axis 98 which has a shape matching the inside surface of inner U-shaped portion 88a1. Thus, each liner 142 is firmly supported at all sides by either the inside surface of an inner U-shaped portion 88a1 or the inside surface of outer tube element 134. Moreover, each liner 142 fills the tapered section 99 of channel 96 where outer portion 88a2 touches outer tube element 134.

Each liner 142 is provided with an internal channel 144 extending in the longitudinal direction and accommodating a cable 90.

An alternative liner 142 may be designed such that it defines an open channel 144 towards central axis 98. These open channels 144 together with the inner surfaces of the inner U-shaped portions 88a1 define channels for accommodating cables 90. The inner surface of open channels 144 has a shape of a portion of a circle to support a cable 90.

Liner 142 may, as a further alternative be implemented by a wire shaped element. Such a wire shaped element met have a circular, oval, triangular, etc. shaped cross section.

Liner 142 may be made from a flexible plastic, like polymer, that shows a predetermined rotational stiffness, longitudinal stiffness, and manufacturability. Alternatively, it can be made from a metal, e.g. one of the metals mentioned above. It can be made by extrusion, 3D printing, etc. Preferably, the material has an as low as possible friction coefficient relative to cables 90. UHMWPE and/or Teflon™. Its dimensions are such that they match those of the selected cable 90, intermediate tube element 88a and outer tube element 134.

Due to its corrugated structure, intermediate tube element 88a counteracts its own deformation by radial forces (caused by bending of the tubular body 18) or tangential forces (caused, e.g., by rotating the tubular body 18 at the proximal end in use). Thus, channels 96 defined by the inner U-shaped portions 88a1 keep their form even when the tubular body 18 is bent/deflected along its length at several locations. The liners 142 being located in these channels 96 will, therefore, also keep their form when the tubular body 18 is bent/deflected along its length, as will the channels 144 defined within liners 142 or will the channels defined between open channels 144 and channels 96 accommodating the cables 90. Moreover, the tapered portions of channels 96 at locations where outer portions 88a2 touch outer tube element 134 are now filled with liners 142. Consequently, cables 90 do not experience increased friction or get stuck in these tapered portions in use.

In the embodiment of FIGS. 9A, 9B at least one of outer tube element 134 and intermediate tube element 88a is made from a metal like stainless steel, cobalt-chromium alloy, or a shape memory alloy such as Nitinol®.

Figure 9C:
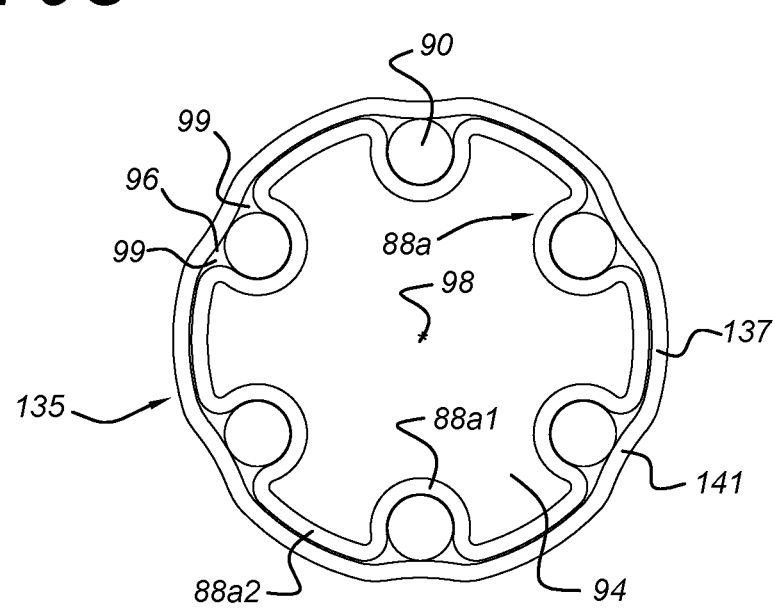
FIG. 9C shows an alternative structure for the embodiment of FIGS. 9A and 9B.

FIG. 9C shows an alternative solution to the one of FIGS. 9A and 9B. The intermediate tube element 88a is the same as the one of FIGS. 9A and 9B. However, an alternative outer tube element 135 is applied. Outer tube element 135 is provided with a plurality of rims 141, one rim 141 per cable channel 96. Each rim 141 extends to a certain predetermined extent in an open portion of one cable channel 96 facing away from central axis 98. Moreover, each rim 141 extends along the entire length of outer tube element 135. Each two adjacent rims 141 are mutually connected via outer tube element portions 137 all located on a same circle about central axis 98, such that intermediate tube element portions 88a2 are aligned with outer tube element portions 137 such that one intermediate tube element portion 88a2 touches one outer tube element portion 137.

There may be small tapered sections 99 of cable channel 96 between outer tube element 135 and intermediate tube element 88a, as indicated in FIG. 9C. However, because rims 141 extend slightly into channels 96 and support cables 90, risks for cables 90 to experience increased friction or get stuck in these tapered sections 99 are reduced.

For the rest, the same properties may apply to outer tube element 135 as to outer tube element 134 (or 86).

In the embodiment of FIG. 9C at least one of outer tube element 135 and intermediate tube element 88a is made from a metal like stainless steel, cobalt-chromium alloy, or a shape memory alloy such as Nitinol®. They are attached to one another at predetermined locations along their length to provide the tubular body with enough rotational and longitudinal stiffness.

Figure 10A:
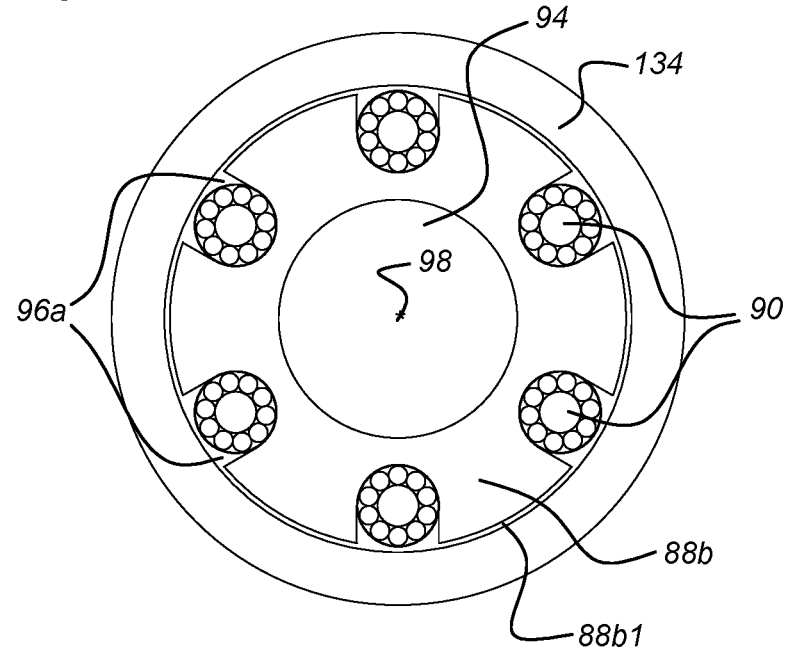
FIG. 10A shows a cross section through two hollow tubes inserted into one another; the inside tube is extruded/machined/laser engraved such that it has cable channels at its outside surface; an outer liner closes the channels and protects the inside tube.

FIG. 10A shows a further embodiment of the invention. It has the same outer tube element 134 as the embodiment of FIGS. 9A, 9B. However, intermediate tube element 88b has a different shape. I.e., intermediate tube element 88b has, in general, both an internal and external circular cross section and a uniform thickness but has a plurality, here six, of channels 96a arranged in its outside surface. They have a shape of an open U, the open end of which is facing outward as seen from central axis 98. Each one of them accommodates a cable 90. At their internal sides, the U-shaped channels, preferably, have the form of half a circle to properly support a cable 90. Towards the outer surface of intermediate tube element 88b, U-shaped channels 96a have walls with a planar cross section oriented perpendicular to the outside surface. Deviations of up to +/−10%, preferably less than +/−5%, from such a 90° orientation may be acceptable.

Between the channels 96a, intermediate tube element 88b has outer surface portions 88b1 having a circular shape which, in the assembled state of the tubular body 18, touches the inside surface of outer tube element 134. Outer surface portions 88b1 are attached at predetermined locations to outer tube element 134 in the same way, e.g. by means of gluing or brazing or lips, as are outer portions 88a2 in the embodiment of FIGS. 9A, 9B.

The channels 96a may be straight or spiral along the length of the tubular body 18.

Intermediate tube element 88b is provided with a deflectable section in deflectable zone 17 and a flexible section in flexible zone 12a. Any suitable technical implementation can be used. E.g., slotted structures like the ones shown at 72 and 74 in the outer tube element 86 of the embodiment of FIGS. 5A-5C or 6A-6C can be used. Alternatively, the slotted structure 106 as shown in corrugated intermediate tube element 88 of FIG. 7A can be used.

Intermediate tube element 88b has, preferably, a uniform thickness and is preferably made from a metal. Suitable materials are steel alloys like stainless steel, cobalt-chromium alloys, or a shape memory alloy such as Nitinol®. However, any other material that can meet the requirements as to rotational stiffness, longitudinal stiffness, play and manufacturability as regards the above explained slots/slotted structures can be selected too. Preferably, the material has an as low as possible friction coefficient relative to cables 90. a material like UHMWPE and/or Teflon™.

The thickness of intermediate tube element 88b depends on its application. For medical applications the thickness in locations without channels 96a may be in a range of 0.3-1.5 mm, preferably 0.4-0.8 mm, more preferably 0.5-0.7 mm.

Even though, due the channels 96a, intermediate tube element 88b has a cross section with varying thickness, experiments have shown that the slots of slotted structures, like 72, 74, 106, 136 in intermediate tube element 88b can be made by laser cutting with a laser beam substantially directed perpendicular to the central axis 98. These slots which are made to just separate adjacent elements may have a width, preferably, in a range of 0-50 μm, more preferably 0-30 μm.

Channels 96a can be made in intermediate tube element 88b by means of laser engraving a metal tube element by a laser beam directed perpendicular to its outside surface. An advantage of intermediate tube element 88b is that the slotted structures and channels 96a can be made in one single process with the same laser machine resulting in an intermediate tube element 88b that can be produced at reasonable costs and high reliability. Other techniques may be used instead. E.g., 3D laser printing may be used, or intermediate tube element 88b may be made by extrusion.

Also here cables 90 may have a thickness of 0.1 to 1.0 mm.

Due to its essentially circular cross section, intermediate tube element 88b counteracts its own deformation by radial forces (caused by bending of the tubular body 18) or tangential forces (caused, e.g., by rotating the tubular body 18 at the proximal end in use). Moreover, at locations without channels 96a, the thickness of intermediate tube element 88b may be rather large which is advantageous for its rotation stiffness, longitudinal stiffness, and the strength of hinges made by slotted structures. This is especially true if intermediate tube element 88b is made from metal. Thus, channels 96a defined by the U-shaped channels 96a keep their form even when the tubular body 18 is bent/deflected along its length at several locations. Moreover, the channels 96a do not have tapered portions at locations where U-shaped channels 96a meet outer portions 88b1. Consequently, cables 90 do not experience increased friction or get stuck in a transition area from U-shaped channels 96a to outer portions 88b1.

It will be understood by persons skilled in the art that channels 96a may be provided on the inside surface of intermediate tube element 88b1 instead of, or in addition to on the outside surface. If applied on its inside surface, inner tube element 92 should be applied too.

In the embodiment of FIG. 10A at least one of outer tube element 134 and intermediate tube element 88b is made from a metal like stainless steel, cobalt-chromium alloy, or a shape memory alloy such as Nitinol®. They are attached to one another at predetermined locations along their length to provide the tubular body with enough rotational and longitudinal stiffness.

Figure 10B:
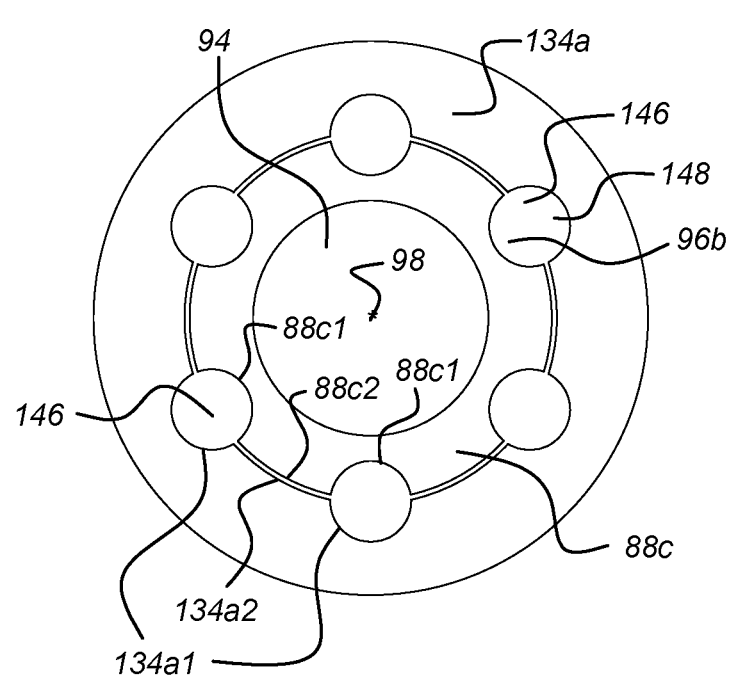
FIG. 10B shows a cross section through two hollow tubes inserted into one another; the inner tube is extruded/machined/laser engraved such that it has portions of cable channels at its outside surface; the outer tube is extruded/machined such that it has portions of cable channels at its inside surface aligned with the portions of the cable channels at the outside surface of the inner tube.

FIG. 10B shows a further alternative embodiment. Here, inner tube element 88c has a plurality of, here six, channels 96b in its outside surface having a cross section of half a circle, as defined by outer portions 88c1. In between these outer portions 88c1, intermediate tube element 88c has outer portions 88c2 having comparable or identical cross sections as outer portions 88b1 shown in FIG. 10A. For the rest, intermediate tube element 88c may be identical to intermediate tube element 88b of FIG. 10A. Channels 96b may be formed such that their cross sections form a smaller portion or larger portion of a circle.

In FIG. 10B, outer tube element 134a has an essentially uniform thickness but is provided with a plurality of, here six, channels 148 in its inside surface having a cross section of, preferably, half a circle, as defined by inner portions 134a1. In between these inner portions 134a1, outer tube element 134 has outer portions 134a2 having circular cross sections. Channels 148 may be longitudinal slots formed in the inside surface of outer tube element 134a. For the rest, outer tube element 134 may be identical to outer tube element 134 of FIG. 10A. Channels 148 may be formed such that their cross sections form a smaller portion or larger portion of a circle, as long as one channel 96b with its counterpart channel 148 together form one channel 146 with a circular cross section. Outer tube element 134a is, e.g., made from plastic and may be manufactured by extrusion or 3D printing techniques.

Together, one channel 96b and one channel 148 forms one channel 146 with a circular cross section accommodating one cable 90 (not shown in FIG. 10B). Other cross sections than circular may be applied as well. Each such channel 146 may be straight or spiral in the longitudinal direction of tubular body 18.

The structure of FIG. 10B may be designed such as to have the same advantages as the one of FIG. 10A, as regards longitudinal stiffness and rotational stiffness. Channels 96b can be made in intermediate tube element 88c by means of laser engraving a metal tube element by a laser beam directed perpendicular to its outside surface. An advantage of intermediate tube element 88c is that the slotted structures and channels 96b can be made in one single process with the same laser machine resulting in an intermediate tube element 88c that can be produced at reasonable costs and high reliability. Other techniques may be used instead. E.g., 3D laser printing may be used, or intermediate tube element 88b may be made by extrusion.

In the embodiment of FIG. 10B at least one of outer tube element 134a and intermediate tube element 88c is made from a metal like stainless steel, cobalt-chromium alloy, or a shape memory alloy such as Nitinol®. They are attached to one another at predetermined locations along their length to provide the tubular body with enough rotational and longitudinal stiffness.

Figure 11A:
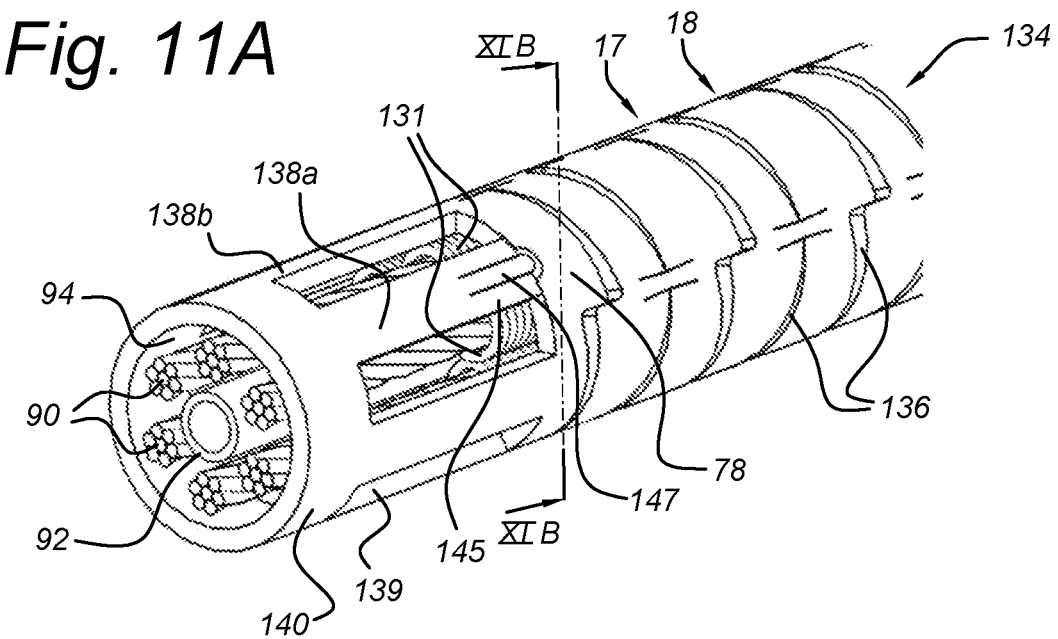
FIGS. 11A-11H show alternative embodiments where tangential movement of cables is blocked by other means than an intermediate tube element.
Figures 11B, 11C, 11D:
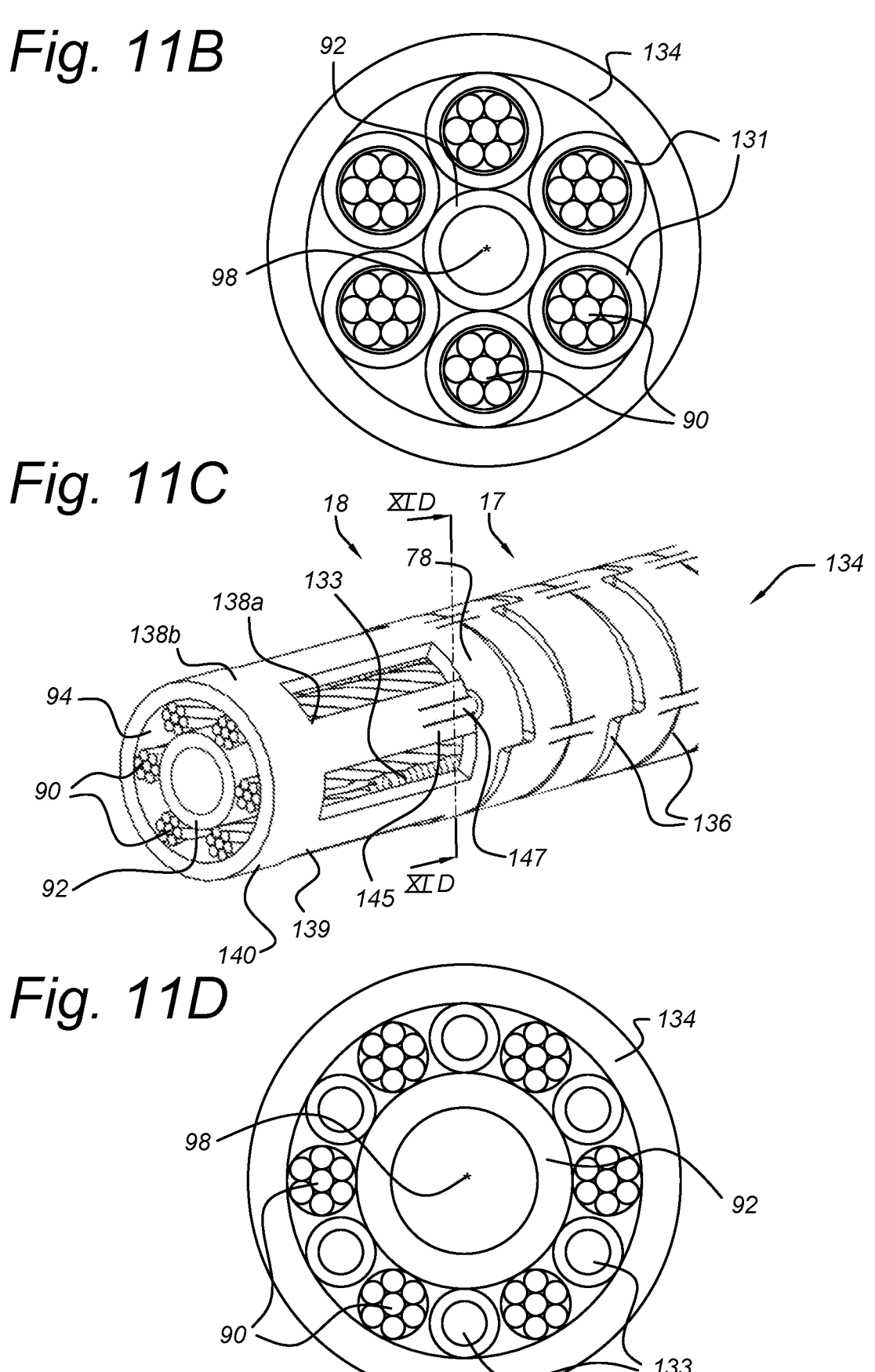
Figures 11E, 11F:
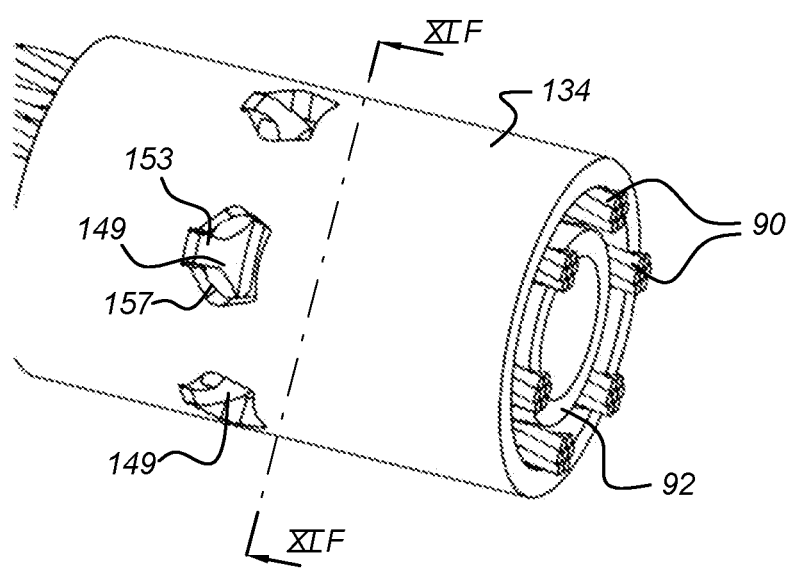

FIGS. 11A, 11B, 11C, 11D, 11E, 11F show embodiments in which cables 90 are blocked from tangential movements by other tangential blockers than an intermediate tube element. FIG. 11B shows a cross section through the embodiment of FIG. 11A perpendicular to the central axis 98 as indicated by arrows XIB in FIG. 11A. FIG. 11D shows a cross section through the embodiment of FIG. 11C perpendicular to the central axis 98 as indicated by arrows XID in FIG. 11B. FIG. 11F shows a cross section through the embodiment of FIG. 11E perpendicular to the central axis 98 as indicated by arrows XIF in FIG. 11E.

In the embodiment of FIGS. 11A, 11B outer tube element 134 is the same as in in FIG. 9A. As shown, in the embodiment of FIGS. 11A and 11B, strips 138 are implemented as two different types, i.e., alternating strips 138a and 138b. Strip 138a is designed such that, at its distal end, it is attached to ring-shaped portion 140. At its proximal end 145, strip 138a is disconnected from ring-shaped portion 78. Moreover, proximal end 145 may be provided with an additional lip 147. Adjacent to strip 138a, at both sides, strips 138b are present which are at both their distal end and proximal end, respectively, attached to ring-shaped portion 140 and ring-shaped portion 78, respectively. In the shown embodiment there are three strips 138a and three strips 138b. However, other numbers may be applied.

The embodiment has six adjacent cables 90 (other numbers may be applied). Each one of them is accommodated in a tube 131. These tubes 131 are flexible and, in an embodiment, contacting both inner tube element 92 and outer tube element 134 such that they are slightly clamped between inner tube element 92 and outer tube element 134. Each one of these tubes 131 has an internal hollow channel accommodating one cable 90. The cross section size of these hollow channels is such that the cable 90 inside them can freely move in the longitudinal direction with as low friction as possible.

In the longitudinal direction, each one of the tubes 131 with their cables 90 inside may extend completely linearly or spirally to provide the cables 90 with a tangentially rotated location along the body 18, for purposes explained above.

The cross sectional form of the tubes 131 may be circular, as shown in FIG. 11B. However, the invention is not limited to such an implementation. Its cross section may be oval, rectangular, etc. This also applies to the hollow channels within them.

Tubes 131 may be implemented by coils, e.g. made of metal, extending longitudinally from deflectable zone 17 below strips 138a, 138b, as shown in FIG. 11A. The metal may be a steel alloy like stainless steel, cobalt-chromium alloy, Nitinol™, etc. In such a case, each one of the lips 147 of the strips 138b is, preferably, welded to one tube 131. By doing so, at the location of the strips 138a, 138b, the tubes 131 and cables 90 are blocked from tangential rotation relative to outer tube element 134. To block such tangential rotation of tubes 131 and cables 90 relative to outer tube 134 along the entire body 18, tubes 131 are also attached to outer tube element 134 at other locations along the tubular body 18. The number of such attachments depends on the required rotational stiffness, and play, as well as flexibility of the intermediate zone 12a. Moreover, such attachments to outer tube 134 support longitudinal stiffness. So, here, tubes 131 function as tangential rotation blockers for cables 90.

Tubes 131 may, alternatively, be made from a suitable other material including polymers, UHMWPE and/or Teflon™. These materials cannot be welded to outer tube element 134. So, other tangential blockers should be applied to prevent tubes 131 from tangential rotation relative to outer tube 134. Such tangential blockers may be implemented by lips arranged at predetermined locations along outer tube element 134 and bent inwardly towards central axis 98 in order to fix the tangential position of tubes 131. An alternative may be that outer tube element 134 is provided with longitudinal rims on its inner surface which may each taper towards central axis 98 and contact two adjacent tubes 131 in order to fix the tangential position of tubes 131. Also inner tube 92 may be provided with such tangential blockers on its outer surface, e.g. in the form of longitudinal rims or extensions at predetermined locations. Such (extra) tangential blockers can also be applied in case tubes 131 are made from a metal.

It is observed that the embodiment where outer tube element 134 has such rims on its inner surface corresponds to the alternative embodiment explained with reference to FIGS. 8A-8C where alternative outer tube element 130 is designed such that it defines an open channel 132 towards central axis 98.

Cables 90 may be provided with crimp bushings like crimp bushings 143 (cf. FIGS. 19A and 19B).

FIGS. 11C, 11D show a further alternative embodiment. Here, body 18 comprises outer tube element 134 and inner tube element 92 as explained with reference to earlier figures. It is observed that this embodiment is explained with reference to outer tube element 134. However, any other outer tube element, e.g., as explained here can be used instead. Adjacent cables 90 are separated from one another by tangential spacer elements 133. They may be implemented as flexible tubes, flexible and stretchable cables, etc. The flexible tubes 133 may be hollow or solid. They are, preferably, made from a material that provides an as low as possible friction to cables 90, e.g., polymers, UHMWPE and/or Teflon™. However, they can also be made from steel alloys like stainless steel, cobalt-chromium alloys, Nitinol™, etc. They may be made as a coil, as shown in FIG. 11C. Their main function is to prevent tangential movement/rotation of cables 90 in operation of the instrument. So, the tangential spacer elements 133 should have a minimum stiffness in their cross sectional direction, as determined by the application of the instrument.

Again, both cables 90 and tangential spacer elements 133 may extend linearly in the longitudinal direction of the body 18 or may spiral to a certain predetermined extent, as explained above.

The tangential spacer elements 133, if made from a metal, are preferably attached, e.g. by laser welding, to outer tube element 134 and/or inner tube element 92 at predetermined locations along body 18 to provide a suitable tangential blocking effect to cables 90. Alternatively, or in addition to that outer tube element 134 is provided with tangential blockers to block tangential spacer elements 133 from tangential rotation relative to outer tube 134. Such tangential blockers may be implemented by lips arranged at predetermined locations along outer tube element 134 and bent inwardly towards central axis 98 in order to fix the tangential position of tangential spacer elements 133. An alternative may be that outer tube element 134 is provided with longitudinal rims on its inner surface which may each taper towards central axis 98 and contact adjacent pairs of one cable 90 and one tangential spacer element 133 in order to fix their tangential positions. Also inner tube 92 may be provided with such means on its outer surface, e.g. in the form of longitudinal rims or extensions at predetermined locations.

In the embodiment of FIGS. 11A, 11B, 11C, 11D at least one of outer tube element 134 and inner tube element 92 is made from one of the above mentioned metals and attached to tubes 131/tangential spacers 133.

FIGS. 11E, 11F show another embodiment with tangential spacer elements 149. FIGS. 11E, 11F show a small portion of outer tube element 134. However, any other outer tube element, e.g., as explained here can be used instead. The small portion of outer tube element 134 can be located anywhere along its longitudinal direction.

FIG. 11E shows an exploded 3D view whereas FIG. 11F shows a cross section perpendicular to central axis 98 as indicated by arrows XIF in FIG. 11E.

The same embodiment has six cables 90, however, any other desired number may be applied. As explained before, cables 90 may extend linearly or spirally from the proximal end to the distal end of body 18, as explained above. Each pair of adjacent cables 90 is mutually separated by a lip 149 forming the tangential spacer element. Lips 149 may be formed by laser (or water) cutting suitable slots 157 in outer tube element 134. Each lip 149 is attached to the main body of outer tube element 134 by a strip 153. Opposite to the strip 153 the tangential width of each lip 149 may be larger than the tangential width of strip 153. Each lip 149 is bent inwardly such that its inner surface 159 (cf. FIG. 11F) contacts inner tube element 92. Because lip 149 is cut from outer tube element 134 its inner surface has a circular shape matching the circular shape of the outer surface of inner tube element 92 which it contacts. There is no strict need to attach lips 149 to inner tube element 92 but one could do so if desired, e.g. by laser welding or gluing or brazing. Such an attachment would cause inner tube element 92 and outer tube element 134 being not rotatable relative to one another. This effect can also be established by providing lip 149 with a lip extension that fits into a hole in inner tube element 92. Such a hole may be a cavity but may, alternatively, be a through-hole. This will be further explained with reference to FIG. 11H.

The tangential distance between tangential sides 161 of two adjacent lips 149 is designed such that cables 90 can move freely in the longitudinal direction of the body 18. All lips 149 are bent inwardly to such an extent they also form radial spacers for cables 90. I.e., they establish a radial distance between the outer surface of inner tube element 92 and the inner surface of outer tube element 134 such that cables 90 can move freely in the longitudinal direction of body 18. The radial distance between the outer surface of inner tube element 92 and the inner surface of outer tube element 134 is, e.g., in a range of 2-30% larger, or preferably in a range of 2-15% larger than the diameter of cables 90.

In an embodiment, the radial distance between the outer surface of inner tube element 92 and the inner surface of outer tube element 134 is slightly larger than the thickness of outer tube element 134 and, thus, of lips 149, e.g., in a range of 2-30% larger, or preferably in a range of 2-15% larger. However, the invention is not restricted to such embodiments.

Such sets of lips 149 are applied at predetermined longitudinal distances along outer tube element 134 such as to form channels for cables 90. If cables 90 need to spiral around the body 18, subsequent sets of such lips 149 will be tangentially shifted to provide the desired spiral form.

Figures 11G, 11H:
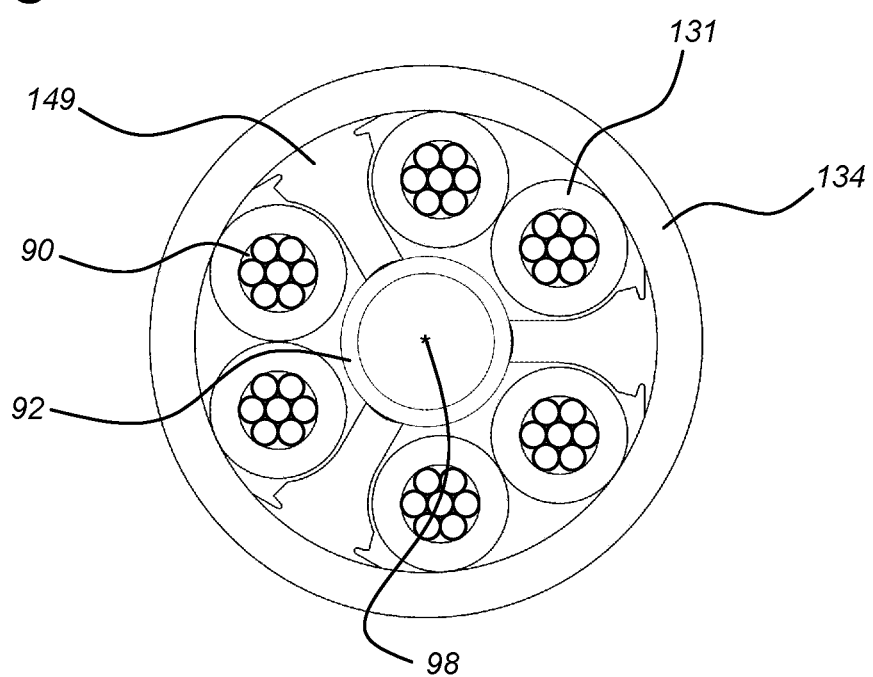

FIG. 11G shows a further embodiment of the instrument according to the invention. The same reference numbers refer to the same elements as in the preceding figures. The embodiment is an alternative to the one of FIGS. 11E and 11F.

FIG. 11G show a cross section through the instrument similar to the one of FIG. 11F. The difference with the embodiment of FIGS. 11E and 11F is that it comprises two tubes 131 between two adjacent lips 149. Each tube 131 forms a channel for guiding a cable 90. Enclosing the cables 90 in a tube 131 has the effect of lowering friction for the movable cables 90 (adjacent cables do not touch each other). At the same time, lips 149 can be made wider than in a situation where there would be one lip 149 per cable 90.

Lips 149 can be bent inwardly towards inner tube element 92 to such an extent that the plurality of lips 149 clamp inner tube element 92 such that it is hard for inner tube element 92 to rotate relative to outer tube element 134 due to the exerted friction. To increase this effect one can, alternatively, weld or glue the lips 149 to the inner tube element 92. As a further alternative, as schematically shown in FIG. 11H, lips 149 can be provided with a lip extension 154 which are inserted into a suitable cavity or through-hole in inner tube element 92. This can be combined with welding or other means of attachment (gluing).

In the embodiment of FIGS. 11E-11H, outer tube element 134 is preferably made from a suitable metal to facilitate inward bending of the lips 149 and ensure they remain in their inwardly bent position. Suitable materials are steel alloys like stainless steel, cobalt-chromium alloys, or a shape memory alloy such as Nitinol®. Thicknesses of outer and inner tube elements 134, 92 and cables 90 can be the same as in other embodiments.

Figure 12:
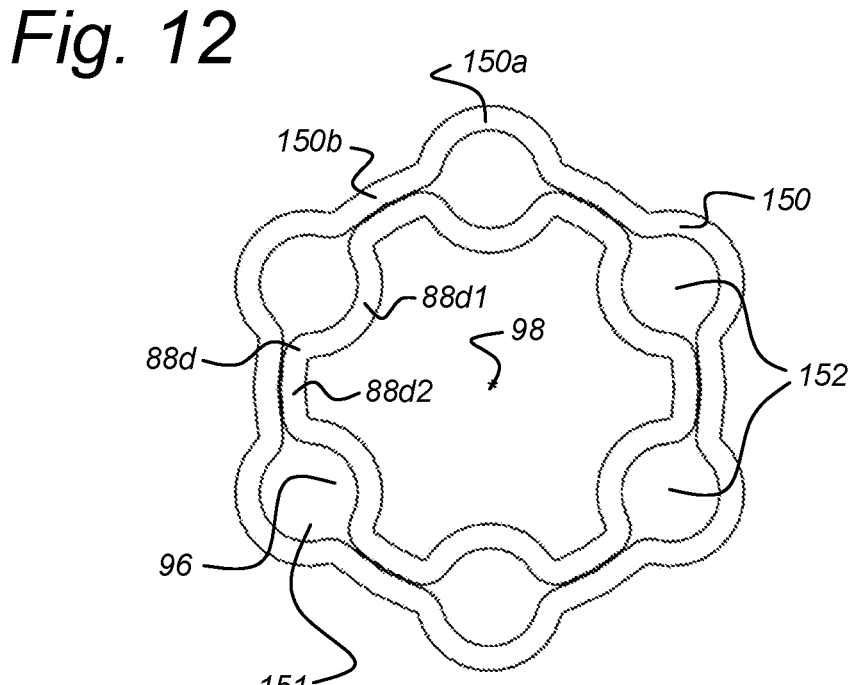
FIG. 12 shows a cross section view of an embodiment of the invention in which two tube shaped elements are inserted into one another; the inner tube has a cross section such as to define portions of cable channels; the outer tube has a cross section such as to define portions of cable channels; the cable channels of the inner and outer tubes are aligned.

In the embodiment of FIG. 12, the tubular body 18 has an intermediate tube element 88d and outer tube element 150. Intermediate tube element 88d has a similar cross section as intermediate tube element 88. Its structure is provided with outer portions 88d2 and inner portions 88d1. Inner portions 88d1 have a cross section of a circle portion. Outer portions 88d2 have outside surfaces with a partial circular cross section and touch inside portions 150b of outer tube element 150.

Outer tube element 150 also has a corrugated cross section. I.e., apart from inner portions 150b, it comprises outer portions 150a. Each outer portion 150a has a cross section of a circle portion and is arranged opposite to one inner portion 88d1. Thus, each outer portion 150a forms a channel 151 opposite to a channel 96 which together form a channel 152 accommodating one cable 90 (not shown in FIG. 12).

Thus, intermediate tube element 88d is designed such as to accommodate only a portion of one cable 90. For the rest, intermediate tube element 88d may have the same structure and features as intermediate tube element 88 or 88a. Intermediate tube element 88d can be made by shaping an originally cylindrical tube with circular cross section into the desired form.

Outer tube element 150 is designed such as to accommodate a portion of one cable 90. For the rest, outer tube element 150 may have the same structure and features as outer tube element 86 or 134. Outer tube element 150 can be made by shaping an originally cylindrical tube with circular cross section into the desired form.

The transitions from inner portions 88d1 to outer portions 88d2 of intermediate tube element 88d may be slightly curved due to the manufacturing process. Similarly, the transitions from inner portions 150b to outer portions 150a of outer tube element 150 may be slightly curved due to the manufacturing process. Consequently, in the area where an outer portion 88d2 of intermediate tube element 88d meets an inner portion 150b of outer tube element 150, channel 152 may show a small tapered portion which may trigger some stucking effect of cables 90 at locations where tubular body 18 is bent or deflected.

In order to prevent such potential stucking effect, a flexible tube may be inserted into each channel 152, in which one cable 90 is arranged. This may be a flexible tube like flexible tube 166 shown in FIGS. 14A, 14B. The flexible tube may be implemented as a flexible coil. Alternatively, a material like liners may be used to fill the tapered portions.

Inner portions 150b are attached to outer portions 88d2 at predetermined locations in a similar way as outer tube element 134 is attached to outer portions 88a2 of intermediate tube element 88a in FIGS. 9A, 9B.

In the embodiment according to FIG. 12, at least one of outer tube element 150 and intermediate tube element 88d are made from one of the above mentioned metals.

Figure 13A:
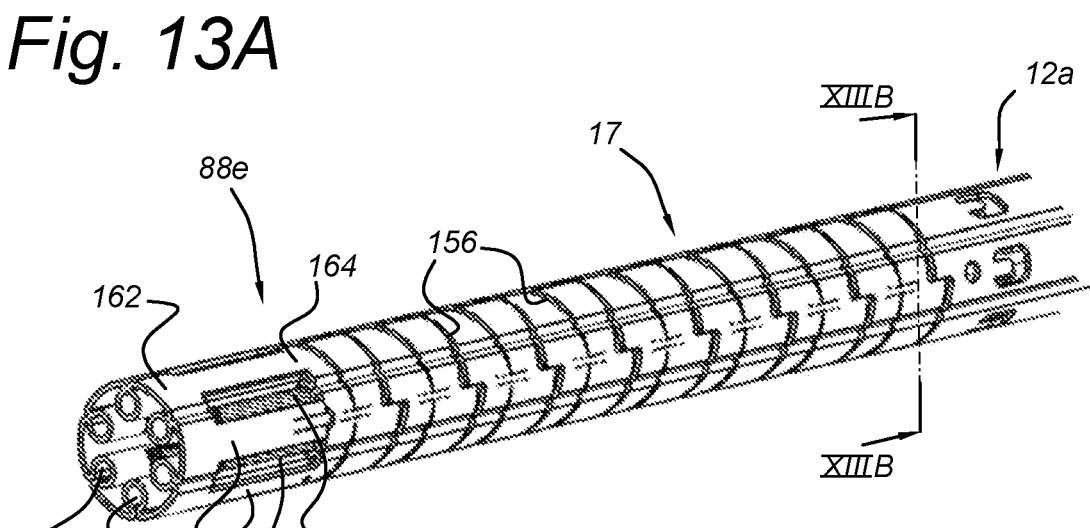
FIGS. 13A, 13B show a cross section view of an embodiment of the invention with one tube which has a cross section such as to define complete cable channels for steering cables.
Figure 13B:
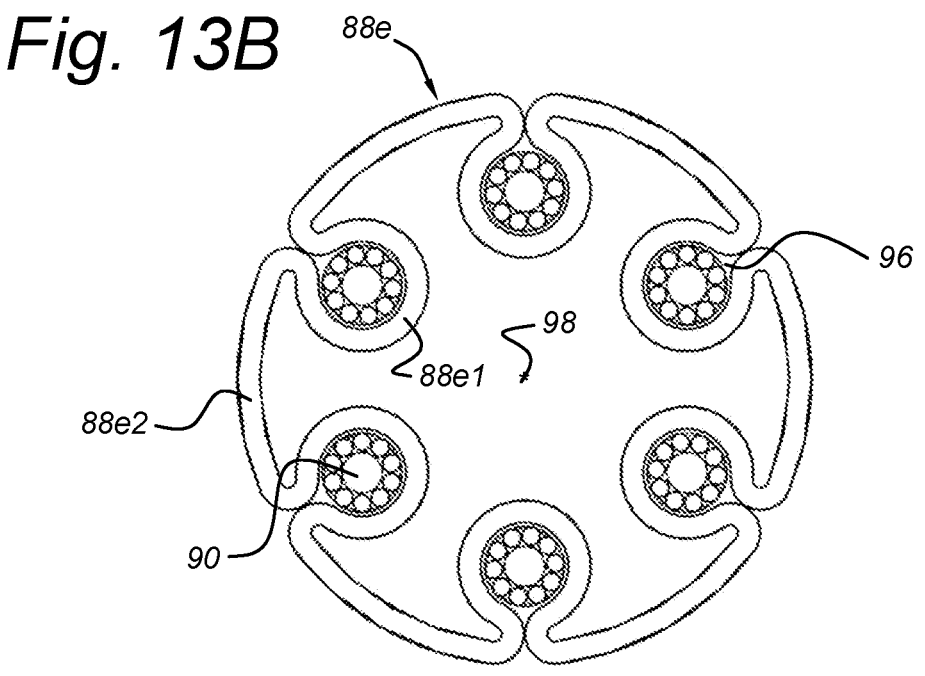

The embodiment shown in FIGS. 13A and 13B has a single intermediate tube element 88e. For its proper functioning no outer tube element and/or inner tube element is required. Of course, due to electrical or sterilization requirements a suitable liner (e.g. made of plastic) inside and/or outside intermediate tube element 88e can be provided. FIG. 13B is a cross section view as defined by arrows XIIIB in FIG. 13A.

Intermediate tube element 88e made from any of the above mentioned materials to meet the requirements as to rotational stiffness, longitudinal stiffness, and manufacturability, as well as deflectability in deflectable zone 17 and flexibility in flexible zone 12a.

In flexible zone 12a, intermediate tube element 88e has a flexible section which may be made with a slotted structure as shown in FIG. 5A (cf. also FIG. 16B). Other slotted structures can be used instead.

In deflectable zone 17, intermediate tube element 88e has a deflectable section 156 with a slotted structure as shown in more detail in FIG. 16D. Other slotted structures can be used instead.

In the tip section, distal to deflectable zone 17, intermediate tube element 88e comprises a non-flexible section 164 which is preferably a ring shaped portion of intermediate tube element 88e that has no, or hardly any holes or slots in it such that it cannot be bent. Distal from non-flexible section 164 and connected/attached to it, intermediate tube element 88e is provided with strips 160 defining slots 158 between them. At their distal ends, the strips 160 are all connected/attached to a non-flexible section 162 which is preferably also a ring shaped portion of intermediate tube element 88e that has no, or hardly any holes or slots in it such that it cannot be bent. Preferably, there are as many strips 160 and slots 158 as there are cables 90.

Intermediate tube element 88e has a corrugated cross section. It is provided with outer portions 88e2 and inner portions 88e1. Outer portions 88e2 define the outer circumference of intermediate tube element 88e and may be located on a circle. Adjacent outer portions 88e2 are connected to one another by means of one inner portion 88e1. Inner portions 88e1 have a cross section of almost an entire circle. I.e., at locations where inner portions 88e1 meet outer portions 88e2, inner portion 88e1 has opposing sides touching one another such as to form an essentially closed channel 96. Each channel 96 accommodates one cable 90 and may be straight or spiraled in the longitudinal direction.

The transitions from inner portions 88e1 to outer portions 88e2 of intermediate tube element 88e may be slightly curved due to the manufacturing process. Consequently, in the area where two opposing sides of inner portion 88e1 touch each other, channel 96 may show a small tapered portion which may trigger some stucking effect of cables 90 at locations where tubular body 18 is bent or deflected.

In order to prevent such potential stucking effect, a flexible tube may be inserted into each channel 96, in which one cable 90 is arranged. This may be a flexible tube like flexible tube 166 shown in FIGS. 14A, 14B. Alternatively, some form of liner may be used to fill up the tapered portion. The flexible tube may be implemented as a flexible coil.

The thickness of intermediate tube element 88e, which is preferably uniform, depends on its application. For medical applications the thickness may be in a range of 0.02-2.0 mm, preferably 0.03-1.0 mm, more preferably 0.05-0.5 mm, and most preferably 0.08-0.4 mm. The diameter of the intermediate tube element 88e depends on its application. For medical applications the diameter may be in a range of 0.5-20 mm, preferably 0.5-10 mm, more preferably 0.5-6 mm.

The slots of the slotted structure 156 in intermediate tube element 88e can be made by laser cutting as indicated above. These slots which are made to just separate adjacent elements may have a width, preferably, in a range of 0-50 μm, more preferably 0-30 μm.

Due to its corrugated structure, intermediate tube element 88a counteracts its own deformation by radial forces (caused by bending of the tubular body 18) or tangential forces (caused, e.g., by rotating the tubular body 18 at the proximal end in use). Thus, channels 96 defined by the inner U-shaped portions 88e1 keep their form even when the tubular body 18 is bent/deflected along its length at several locations.

Figure 14A:
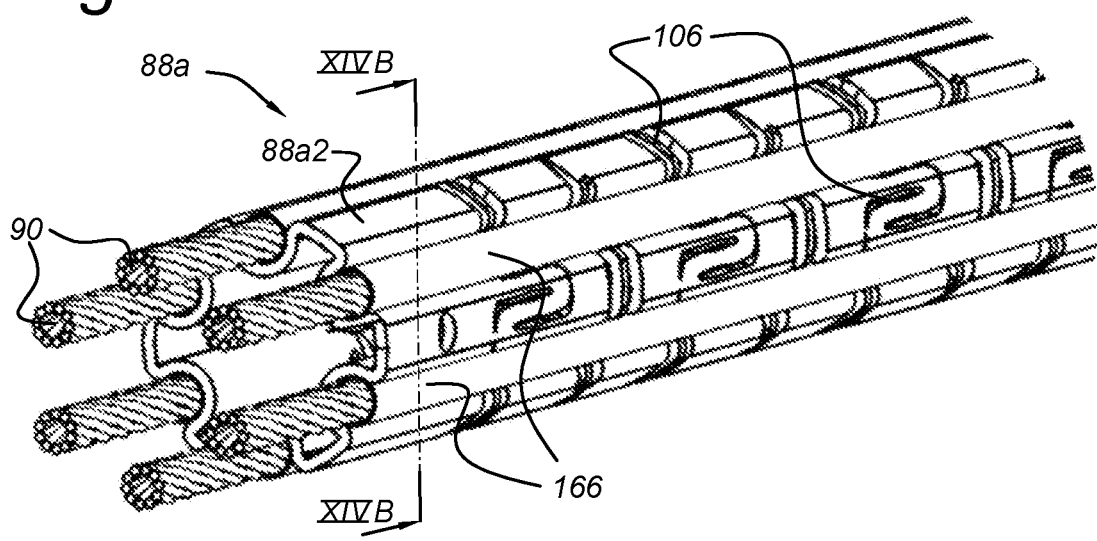
FIGS. 14A, 14B show an embodiment in which steering cables are arranged in additional tubes which are embedded in the cable channels of the tube and attached to the tube.
Figure 14B:
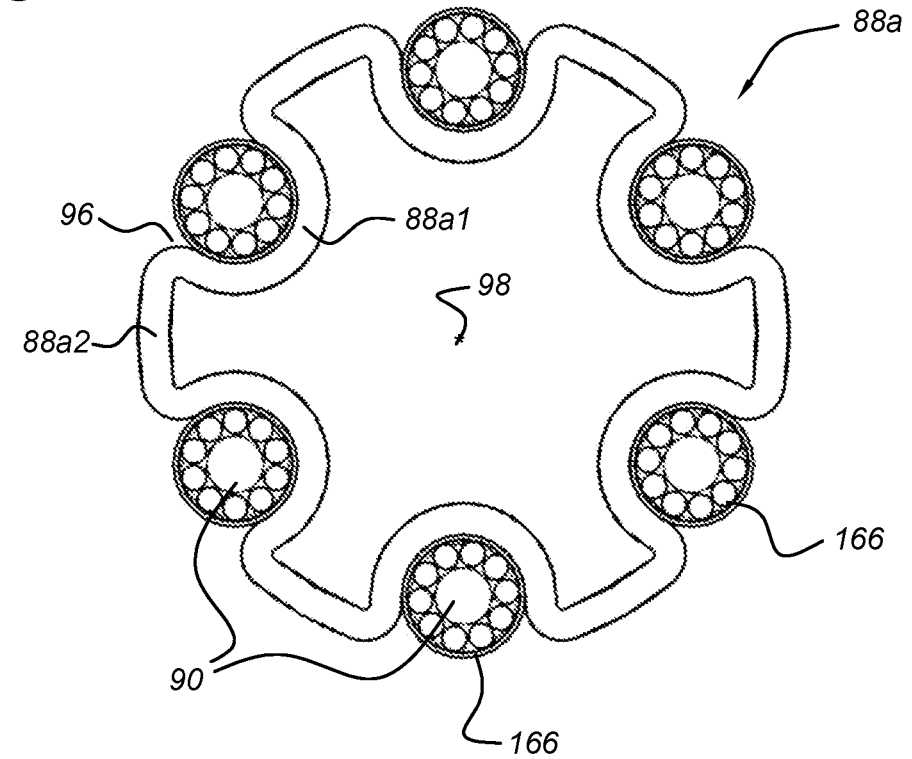

FIGS. 14A, 14B show intermediate tube element 88a of FIGS. 8A, 8B, 8C, 9A, 9B once more. Whereas FIGS. 8A-8C show a specially designed outer tube element 130 and FIGS. 9A, 9B show specially designed liners 142 to prevent cables 90 from being stuck in tapering areas of channel 96. FIGS. 14A, 14B show an alternative solution. I.e., in the embodiment of FIGS. 14A, 14B an extra tube 166 is provided in each channel 96. Each such tube 166 accommodates one cable 90.

Tubes 166 are made from a suitable material and have a suitable thickness such that they meet certain predetermined requirements as to longitudinal and radial stiffness, as well as friction with cables 90. An example is Ultra High Density Polyethylene. Due to its low friction, such a material would also simplify inserting the cables 90 into the channels of intermediate tube element once ready. The tube 166 can be made strong and yet flexible enough to allow deflectable zone 17 and flexible section 12a to deflect/bend in use with acceptable forces, while still essentially keeping their cross section shape.

In the embodiment shown in FIG. 14A, intermediate tube element 88a is provided with deflectable section 106 with a same slotted structure as the one applied in intermediate tube element 88 of FIG. 7A.

Tubes 166 have a circular cross section and have, preferably a uniform thickness. They may be made of a suitable plastic like polymer. Alternatively, they may be made from steel alloys like stainless steel, cobalt-chromium alloys, or a shape memory alloy such as Nitinol®. If desired, tubes 166 may be provided with slotted structures to increase their flexibility. For medical applications, a typical thickness may be in a range of 0.05-0.5 mm, preferably 0.05-0.3 mm.

The extra tubes 166 can be used themselves as a elements that control a function of the steerable instrument at its distal end as controlled by a suitable steering member at the proximal end.

Figure 15A:
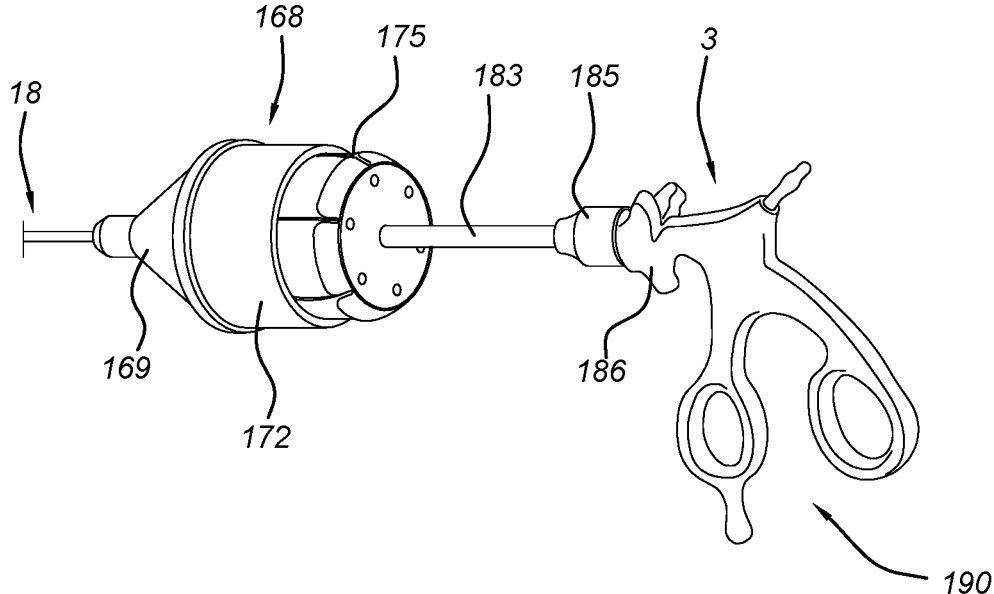
FIGS. 15A, 15B show a 3D and cross sectional view, respectively, of a proximal steering arrangement.
Figure 15B:
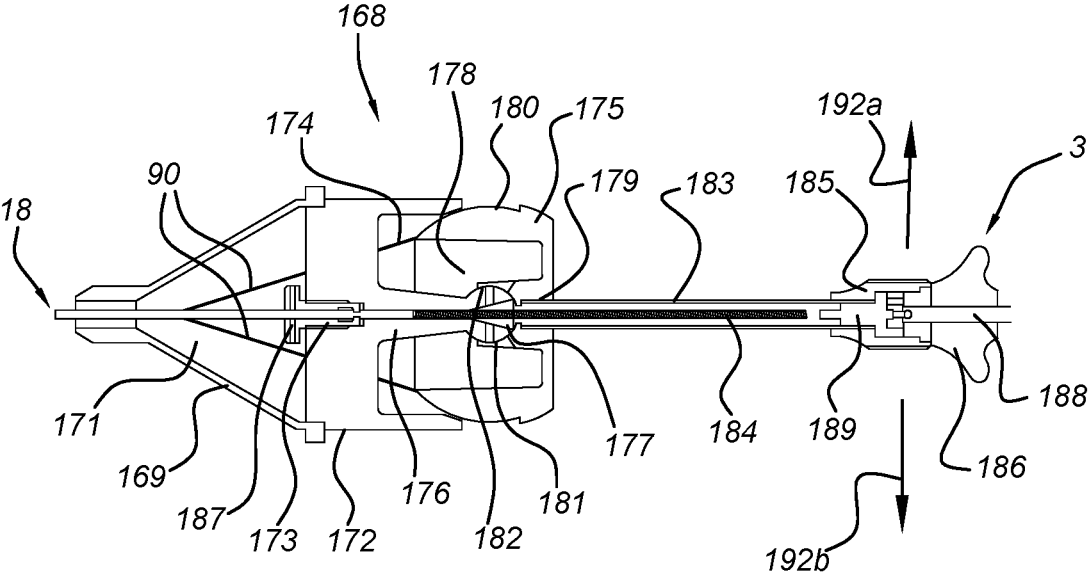

FIGS. 15A, 15B show an implementation example of the proximal end of the steerable instrument. FIG. 15B shows a cross sectional view of the structure shown in FIG. 15A.

At its proximal end, cables 90 may be controlled, i.e. pulled, by any suitable steering mechanism. Such steering mechanism may, for instance, be a proximally arranged deflectable zone like distally arranged deflectable zone 17 and attached in a suitable way to cables 90. Alternatively, the proximal steering mechanism may be implemented by means of a robot. As a further example, the proximal steering mechanism may be implemented as a steering device 168 with a ball-shaped steering device 180. Such a steering device 168 may have any suitable design. An example is shown in FIGS. 15A, 15B.

Steering device 168 comprises a housing 169. Housing 169 tapers towards its distal end and increases in diameter towards its proximal end. In an example, housing 169 has a conical shape which is symmetrical about a central axis. Housing 169 encloses a hollow space 171 and is open both to its distal end and proximal end.

At its distal end, hollow space 171 ends in a channel accommodating a proximal end portion of tubular body 18. At its proximal end, housing 169 is connected/attached to a supporting member 172. Supporting member 172 has a channel 173 at its central axis which accommodates the most proximal end of tubular member 18. A clamping ring shaped element 187 surrounds tubular body 18 within channel 173 such as to clamp tubular body 18 within channel 173. Tubular body 18 can be attached to supporting member 172 in any other way such that it extends for the distal end of supporting member 172 along the central axis if housing 169. In an embodiment, housing 169 is not applied.

Supporting member 172 has a hollow space 174 towards its proximal end. Inside this hollows space 174, supporting member 172 comprises a pin-shaped member 176 extending in the proximal direction. At its most proximal end, pin-shaped member 176 is provided with a ball-shaped member 181 with a ball-shaped outer surface. Channel 173 extends through this pin-shaped member 176 and ball-shaped member 181 along a central axis of supporting member 172. Inside ball-shape member 181, channel 173 has an increasing diameter towards the proximal end such as to define a conical space 177.

Supporting member 172 supports a ball-shaped steering member 180. Steering member 180 has a, partially, ball-shaped outer surface which is symmetrical about a central axis of the ball-shaped steering member 180 and supported by a suitably designed proximal inner surface portion of supporting member 172. Ball shaped steering member 180 has a ball-shaped inner surface 182 supported by ball-shaped member 181 of supporting member 172.

Hollow space 174 is designed such that ball-shaped steering member 180 can rotate about ball-shaped member 181 towards and away from the central axis of supporting member 172 such that the central axis of ball-shaped steering member 180 deflects from the central axis of supporting member 172 in any desired direction. In an embodiment, the ball-shaped steering member 180 and supporting member 172 are arranged such that if ball-shaped steering member 180 is rotated in the tangential direction about its central axis also supporting member 172 and housing 169 are forced to rotate about their central axes together with tubular body 18. This can, e.g., be implemented by providing ball-shaped member 180 and supporting member 172 with suitable cooperating slots and ribs/pins.

At its proximal side, ball-shaped member 180 is provided with a cable fastening mechanism 175. In the embodiment shown, the cable fastening mechanism 175 comprises a flange with a plurality of slots. Each slot accommodates and clamps a proximal end of one cable 90. This can be done in several ways known from the prior art. There are no limitations as to the specific implementation. Other structures than a flange 175 can be implemented to provide this clamping effect.

As shown in FIG. 15B, channel 173 in ball-shaped 181 widens towards its proximal end and defines a conically shaped space 177 towards the proximal end.

At its central axis, ball-shaped member 180 has a channel 179 accommodating a distal end of a hollow tube 183. Proximal end of hollow tube 183 is accommodated by a rotation element like a knob 185. Hollow tube 183 is connected to ball-shaped member 180 and to knob 185 such that when knob 185 is rotated about its central axis, also hollow tube 183 and ball-shaped member 180 are rotated about their central axes. Thus, rotating knob 185 causes the whole steering device 168 to rotate with the same angular amount. The same applies to tubular body 18 since tubular body 18 is fixed or clamped to supporting member 172 by clamping ring shaped element 187.

Internally, knob 185 has a hollow space accommodating cable fastening member 189 attached to a proximal end of actuation cable 184. Actuation cable 184 extends through hollow tube 183, channel 179 of ball-shaped member 180, channel 173 of supporting member 172 and elongated channel 94 of tubular body 18 towards its most distal end. At the most distal end of tubular body 18, actuation cable 184 is connected or attached to a tool such that longitudinal movement of actuation cable 184 operates the tool, e.g. jaws of forceps 2. This is known to persons skilled in the art and needs no further explanation here.

When ball-shaped member 180 rotates such that its central axis is deflected from the central axis of supporting member 172 actuation cable 184 can also deflect within ball-shaped member 181 because of the conically shaped space 177 through which actuation cable 184 extends.

Handle 3 is shown to comprise a rotation knob 186 and two jaws 190 which can be operated by two fingers of a hand. The rotation knob 186 is connected to rotation knob 185, e.g., by a screw thread or bayonet connection. I.e., rotation knob 185 is forced to rotate by rotating rotation knob 186 while, then, the rest of the handle 3 keeps its orientation.

Handle 3 comprises an actuation rod 188 which, in the shown embodiment, can be clicked on cable fastening member 189 such that any longitudinal movement of actuation rod 188 translates into a longitudinal movement of cable fastening member 189, and therefore of actuation cable 184. Actuation rod 188 itself is operated by grips 190. The invention is not limited to the handle as shown in FIGS. 15A and 15B. Other suitable handles known from the art may be applied as well.

Instead of to a handle 3, proximal end of hollow tube 183 may be connected or attached to another device, e.g., when the longitudinal channel 94 is not used for accommodating actuation cable 184 but for other purposes. For instance, longitudinal channel 94 may accommodate an electrical cable for supplying electrical current to an electrical tool at the distal end of the tubular body 18, or a gas and/or liquid tight tube for supplying or draining a gas and or a liquid.

An operator of the handle 3 may perform the following actions.

With two fingers the operator can operate the grips 190 such as to longitudinally move actuation cable 184 which then actuates tool 2 at the distal end of tubular body 18.

The operator can rotate rotation knob 186 and thereby rotate the whole steering device 168 and tubular body 18. In the embodiment shown, also actuation cable 184 will then rotate while cable fastening member 189 then rotates relative to actuation rod 188, thus allowing the jaws 190 to keep their orientation. Such rotation of the tubular body 18 is transferred to the distal end of the tubular body 18 even about portions of tubular body 18 which are bent/deflected in use, as is apparent to persons skilled in the art. The tool 2 at the distal end of the tubular body 18 is attached or connected to the tubular body 18 in such a way as to rotate together with the tubular body 18. Thus, the tool can be rotated by rotating knobs 185, 186. Of, course, if desired other rotation mechanisms may be used like a flexible rod extending from knobs 185, 186 to the tool at the distal end. Such a flexible rod can be a hollow tube. Instead of two knobs 185, 186 one knob may be used. The knob or knobs may be located at other places on handle 3.

The operator can deflect hollow tube 183 from the central axis of tubular body 18, as indicated with two arrows 192*a*, 192*b* which then rotates ball-shaped member 180 about a point of rotation as defined by a center point of ball-shaped member 181. By this rotation some of the cables 90 which are connected to a portion of flange 175 moving to the proximal direction of the instrument are pulled whereas other cables 90 which are moving in the distal direction are relaxed. As is evident to persons skilled in the art, this translates into some cables 90 moving to the proximal direction which then cause a bending/deflection of deflectable zone 17 of the tubular body 18, connected at the distal end to these cables 90. Preferably, there are three or more cables 90 which are equally distributed tangentially such that deflectable zone 17 can be deflected in all directions.

In the situation shown, cables 90 are connected at locations on flange 175 which are at a larger distance from the central axis of tubular body 18 than are points of connection of the cables 90 at the deflectable zone 17.

Now some examples of slotted structures that may be used in deflectable/flexible sections of outer, intermediate and/or inner tube elements will be explained in more detail with reference to FIGS. 16A-16D. Several of these deflectable/flexible sections have been shown and explained in great detail in WO2018/067004. Also the other slotted structures of WO2018/067004 may be used here. It is observed that here the term "slotted structure" refers to a structure with one or more slots that extend through the entire thickness of the material.

FIG. 16A shows slotted structure 72 in more detail. This slotted structure 72 comprises, as shown at the left hand side, a circumferential slot 73 in the tube element. Slot 73 extends circumferentially.

Slot 73 has two opposing side walls both extending circumferentially. Slot 73 has a curved slot 85 extending longitudinally, here in the distal direction, from one such side wall and formed as a channel along a portion of a circle having a center point 83. A lip 87 that is shaped as a portion of a circle and matches the form of the curved slot 85 extends from the opposing side wall into this curved slot 85.

Slot 73 has a further curved slot 81 extending longitudinally, here in the distal direction, from one side wall and formed as a channel along a portion of the same circle along which curved slot 85 extends. A lip 79 that is shaped as a portion of a circle and matches the form of the curved slot 81 extends from the opposing side wall into this curved slot 81.

Symmetrically located between lips 87, 79 the slotted structure comprises a convex section 77 with a circular outside surface that abuts an oppositely located concave circular section 75. Convex section 77 and concave section 75 have matching circular outside surfaces such that convex section 77 can rotate in concave section 75 about center point 83.

At the other side of the tube element 180° rotated away in the tangential direction, the slotted structure has an identical shape with two further lips and mating convex and concave sections. Thus, two portions of the tube element at either side of the slot 73 can "rotate" relative to one another about two center points 83, such that they deflect relative to one another. The lips 79, 87 move in the curved slots 81, 85 during such rotation and provide no extra friction. The lips 79, 87 provide extra tangential stability to the tube element when one rotates the entire tube element about its longitudinal central axis. This is an important aid in increasing torque stiffness. They define a predetermined tangential play as determined by the width of the slots 81, 85 surrounding the lips 79, 87.

Hereinafter, a tube element including at least one hinge such as to allow bending of the tube element about the at least one hinge will be explained in more detail. The at least one hinge structure comprises a slotted structure allowing opposite tube element portions of the hinge to bend to a predetermined maximum angle by rotating said at least one hinge. Opposing portions of the hinge at either side of the slotted structure are attached to one another by one or more fracture elements designed such as to break once the hinge is rotated.

As shown in FIG. 16A, slot 73 between convex section 77 and concave section 75 is interrupted one or more times such that convex section 77 and concave section 75 are connected to one another by one or more small bridges 89. These small bridges 89 operate as "fracture elements" as will be explained in more detail with reference to FIG. 18A-18C. I.e., these fracture elements 89 are made on purpose when the instrument is manufactured but are so weak that they will break once convex section 77 is rotated relative to concave section 75 with a predetermined force. Before breaking, the fracture elements 89 provide the tube element with a predetermined extra stiffness such that the tube element can be maneuvered more easily when inserting the tube element inside an other tube element or inserting an other tube element in the tube element. Once broken, the fracture elements 89 play no role anymore and convex section 77 can freely rotate in concave section 75.

At a predetermined longitudinal distance away from slots 73, the tube element comprises an identical slot but then rotated 90° in the tangential direction relative to the slot 73. Thus, two further points of rotation are provided at said predetermined longitudinal distance about which the tube element can rotate but then in a direction perpendicular to the direction of rotation allowed by center points 83.

At a further predetermined longitudinal distance away from slot 73, the structure as defined by slot 73 is again repeated but now identical to the one formed by slot 73. These alternating structures are repeated several times in the longitudinal direction. Thus, the tube element comprises 90° tangentially rotated centers of rotation at predetermined longitudinal distances away from each other allowing the tube element to deflect in all directions.

FIG. 16B shows an embodiment of slotted structure 74, cf. FIGS. 6A and 9A. It has a circumferential slot 243 which comprises an intermediate section 282 and a circumferential slot 245 which comprises an intermediate section 280.

FIG. 16B shows how circumferential slot 245, at one end, ends in a longitudinal slot 219. Opposite to longitudinal slot 219 there is a further longitudinal slot 217. Longitudinal slots 217, 219 define sides of a longitudinal bridge 215.

At its other end, circumferential slot 245 ends at a location rotated between 90° and 160° away in the tangential direction from longitudinal slot 219. Intermediate section 280 comprises a portion with a U-shape. The U-shape is defined by two parallel long sides connected to one another by a base side. Both long sides are curved, preferably such that the curve shape of one long side coincides with a portion of a first circle C1. The second long side has a curve shape preferably coinciding with a portion of a second circle C2. The first and second circles C1 and C2 preferably have a common center point coinciding with the center point of bridge 215. This is implemented as follows.

The intermediate section 280 is communicatively connected to the circumferential slot 245 via a first curved slot 288. Furthermore, the intermediate section 280 is communicatively connected to the circumferential slot 245 via a second curved slot 290. The first curved slot 288 may have the same or a different length than the second curved slot 290. The first curved slot 288 may be shorter than the second curved slot 290. The first curved slot 288 extends between a first end at the circumferential slot 245 and a second end. The second curved slot 290 extends between a first end at the circumferential slot 245 and a second end wherein the second end of the first curved slot 288 is communicatively connected to the second end of the second curved slot 290 via an intermediate slot 292. The first curved slot 288 and the second curved slot 290 are curved about the bridge 215. I.e., the concave sides of the first and second curved slots 288, 290 are facing the longitudinal slot 219 of the bridge 215.

The first curved slot 288 extends between its first end and second end along the first circle C1 wherein the first circle C1 has as a center coinciding with the center point of the bridge 215. The second curved slot 290 extends between its first end and second end along the second circle C2 wherein the second circle C2 has the same center as circle C1.

FIG. 16B shows how circumferential slot 243, at one end, ends in longitudinal slot 217 which, as observed above, forms bridge 215 together with longitudinal slot 219.

At its other end circumferential slot 243 ends at a location rotated between 90° and 160° away in the tangential direction from longitudinal slot 217. Intermediate section 282 comprises a portion with a U-shape. The U-shape is defined by two parallel long sides connected to one another by a base side. Both long sides are curved, preferably such that the curve shape of one long side coincides with a portion of the first circle C1. The second long side has a curve shape preferably coinciding with a portion of the second circle C2. This is implemented as follows.

The intermediate section 282 is communicatively connected to the circumferential slot 243 via a third curved slot 298. Furthermore, the intermediate section 282 is communicatively connected to the circumferential slot 243 via a fourth curved slot 200. The third curved slot 298 may have the same or a different length than the fourth curved slot 200. The third curved slot 298 may be shorter than the fourth curved slot 200. The third curved slot 298 extends between a first end at the circumferential slot 243 and a second end. The fourth curved slot 200 extends between a first end at the circumferential slot 243 and a second end wherein the second end of the third curved slot 298 is communicatively connected to the second end of the fourth curved slot 200 via an intermediate slot 202. The third curved slot 298 and the fourth curved slot 200 are curved about the bridge 215. I.e., the concave sides of the third and fourth curved slots 298, 200 are facing the longitudinal slot 217 of the bridge 215.

The third curved slot 298 extends between its first end and second end along the first circle C1. The fourth curved slot 200 extends between its first end and second end along the second circle C2.

Thus, the first intermediate section 280 defines a U-shape enclosing a first lip 286 extending in a first circular direction as defined by circles C1 and C2. The second intermediate section 282 defines a U-shape enclosing a second lip 284 extending in a second circular direction also defined by circles C1 and C2 but then in the opposite direction of the first lip 286.

Both circumferential slots 243 and 245 extend around the tube element beyond the side of view of FIG. 16B, i.e. towards the side of the tube element not visible in FIG. 16B.

The tube element comprises two further circumferential slots 513 and 549. Circumferential slots 513 and 549, respectively, have an identical shape as circumferential slots 245 and 243, respectively, however, they are rotated 180° in the tangential direction about the tube element. Thus, the two further circumferential slots 513 and 549 define a further longitudinal bridge shaped like longitudinal bridge 215 and located exactly 180° rotated in the tangential direction relative to longitudinal bridge 215.

Circumferential slot 513 extends partly in parallel to circumferential slot 243 such that they define a tangential bridge 244. So, both circumferential slots 243 and 513 extend in planes slightly angled relative to a plane perpendicular to the central axis of the tube element. Similarly, circumferential slot 549 extends partly in parallel to circumferential slot 245 such that they define a tangential bridge 246. So, also circumferential slots 245 and 549 extend in planes slightly angled relative to a plane perpendicular to the central axis of the tube element.

Portions of the tube element at both longitudinal sides of the circumferential slots 243, 245, 513, and 549 can be deflected relative to one another because the center points of longitudinal bridge 215 and the further longitudinal bridge opposite longitudinal bridge 215 operate as rotation points. By such a deflection about the center points of the longitudinal bridges circumferential slots 245 and 549 will close and circumferential slots 243 and 513 will further open, or the other way around depending on the direction of deflection. Because lips 284 and 286 can freely move in circle shaped channels about the same center points they do not or hardly introduce any friction during such deflection.

Some predetermined distance away from the structure defined by circumferential slots 243, 245, 513, and 549, the tube element comprises an identical structure with four further circumferential slots. Two of these four further circumferential slots 643 and 645, respectively, with curved lips 296 and 294, respectively, are also shown in FIG. 16B. These four further circumferential slots 643, 645 are rotated 90° in the tangential direction about the tube element relative to the location of circumferential slots 243, 245, 513, and 549. Circumferential slots 643 and 645 define a longitudinal bridge 649 between them.

Thus, these four further circumferential slots 643, 645 define two further longitudinal bridges (not visible in FIG. 16B) having an identical structure as longitudinal bridge 215 and its counterpart at the opposite side of the tube element, but located 90° rotated. These four further circumferential slots 643, 645 form two further points of rotation allowing portions of the tube element at either longitudinal side of them to deflect relative to one another. However, this deflection is in a surface 90° rotated relative to a surface of deflection as allowed by circumferential slots 243, 245, 513, and 549. In total, the slotted structure shown in FIG. 16B allows a deflection in all directions.

By adding more of such structures with four circumferential slots at predetermined distances in the longitudinal direction of the tube element a hinge can be provided allowing the tube element to deflect in all directions within a predetermined solid angle.

It is observed that the tube element with the slotted structure as shown in FIG. 16B has an improved torque stiffness. The reason is as follows. First of all, circumferential slots 243, 245, 513, 549, 643, 645 do not extend almost 180° in the tangential direction as in some prior art structures and in the structure of FIG. 16A.

Moreover, when a user tries to rotate a tube element as shown in the embodiment of FIG. 16B, the pins 284, 286, 294, 296 can only move in the circumferential direction at a maximum distance of one curved slot 288, 290, 298, 200, and will then be blocked from any further circumferential movement as determined by the width of the slot surrounding them. So, the elastic deformation of and tension will never exceed a certain threshold as determined by the design of the intermediate sections 280, 282, 294, 296.

Also, the tube element shown in FIG. 16B has a very good longitudinal stiffness due the longitudinal bridges 215. I.e., none of the circumferential slots 243, 245, 513, 549, 643, 645 extend in a 360° circumferential distance.

The structure of FIG. 16B is less flexible than the structure shown in FIG. 16A because the tangential bridges 244, 246 between slots 513, 245/549, 643/645 are elastically deformed during deflection. No such tangential bridges are present in the embodiment of FIG. 16A.

FIG. 16C shows an embodiment of slotted structure 106 (cf. FIG. 7A and 14A) in a tube element having an alternative bridge 272. FIG. 16C shows how circumferential slot 245 ends in a longitudinal slot 219. However, here longitudinal slot 219 is communicatively connected to a longitudinal slot 260 via a curved slot 262 such that they form a U-shaped slot. Circumferential slot 243 ends in a longitudinal slot 217 However, here longitudinal slot 217 is communicatively connected to a longitudinal slot 256 via a curved slot 258 such that they form a U-shaped slot in the longitudinally opposite direction of U-shaped slot 219, 262, 260. Thus, a bridge 272 is present which has a mirrored S-shape. Of course, the shape may alternatively be equal to an S-shape. Alternatively, the shape may be a Z-shape or mirrored Z-shape.

Slots 243 and 245 do extend in a plane slightly angled relative to a plane perpendicular to the central axis. They extend along an angle<180° in the tangential direction. At a location 180° rotated relative to the bridge 272, there is an identical structure formed by an identical slot structure. A portion of one circumferential slot 513 of that identical structure, defining tangential bridge 244 with circumferential slot 243 is visible in FIG. 16C.

It is observed that slots 243, 245, 513 are extending in planes angled relative to a plane perpendicular to the central axis in a way opposite to the way shown in FIG. 16B.

Two such S-shaped bridges 272 at opposing sides of the tube element form excellent points of rotation such that portions of the tube element at either longitudinal side of the S-shaped bridges 272 can be deflected relative to one another.

The structure can be combined with curved lips like lips 284 and 286 of FIG. 16A.

The slotted structure shown at the right hand side of FIG. 16C may be repeated one or more times at predetermined longitudinal distances away and, preferably, each time 90° rotated in the tangential direction relative to the adjacent one. One such 90° rotated structure is shown at the left hand side of FIG. 16C without further reference signs.

It is observed that a tube element having S-shaped or Z-shaped bridges 272 as shown in FIG. 16C have a much larger bending angle than embodiments with single straight longitudinal bridges like bridges 215 of FIG. 16B.

FIG. 16D shows an implementation of slotted structure 156, cf. FIG. 13A. It is identical to the one shown in FIG. 16B apart from the lips 284, 286, 294, 296. FIG. 16D is oriented such that its view is partly inside the tube element such as to show the 3D, tangentially symmetrical structure of the slotted structure. Similar tangentially symmetries apply to the slotted structures of FIGS. 16A, 16B, 16C.

Figure 16E:
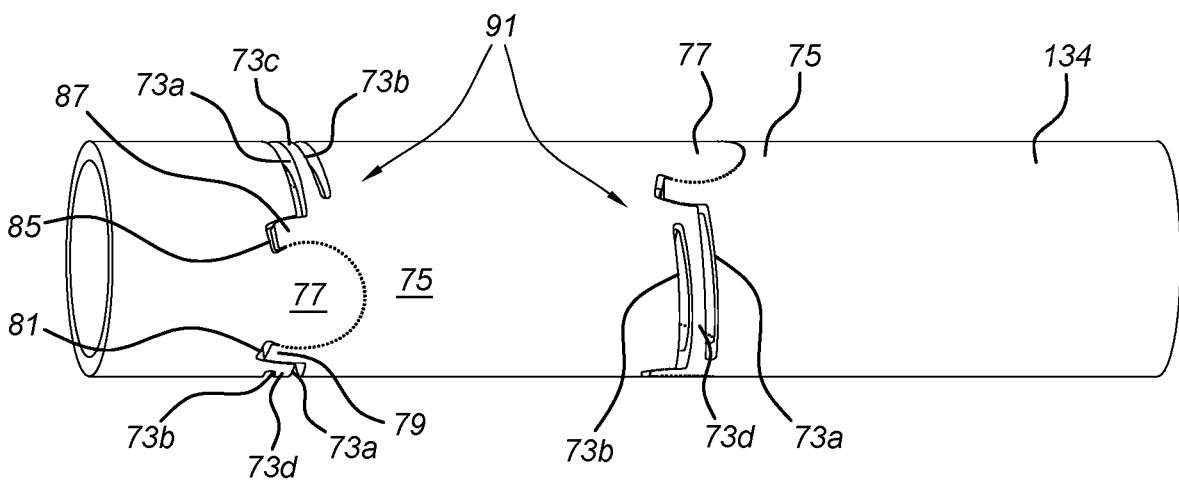

FIG. 16E shows a further example of slotted structures 91 in tube element 134. FIG. 16E shows two adjacent hinges of identical structure but tangentially rotated about 90° relative to one another. So, the two hinges are able to bend adjacent portions of tube element 134 in two different planes perpendicular to one another. By providing more such hinges consecutively rotated about 90° relative to one another, tube element 134 becomes flexible in all directions.

Each hinge 91 is a variant of the hinges shown in FIG. 16A. The same reference numbers refer to the same elements as in FIG. 16A. Whereas the hinges shown in FIG. 16A are formed by one single slot 73 entirely surrounding tube element 134, each hinge 91 is formed by two slots 73*a* and 73*b* which are both not entirely surrounding tube element 134. Slot 73*a* has a portion extending in a circumferential direction with a small angle relative to the tangential direction, which connects to curved slot 85. Curved slot 85 also connects to one end of a further portion of slot 73*a* between convex section 77 and concave section 75, which further portion, at its other end, connects to curved slot 81. Curved slot 81 is also connected to a last portion of slot 73*a* which again extends in a circumferential direction with a small angle relative to the tangential direction. In total, slot 73*a* extends in the circumferential direction along an arc of more than 180°.

Curved slots 85 and 81, respectively, accommodate curved lips 87 and 79, respectively, like in FIG. 16A.

At a location 180° rotated in the tangential direction tube element 134 is provided with a further slot 73*b* which is identical to slot 73*a*. Since both slots 73*a* and 73*b* extend in a circumferential direction at a small angle to the tangential direction along an arc of more than 180°, they define bridges 73*c* and 73*d* extending in the circumferential direction between the circumferential portions of slots 73*a* and 73*b*.

Since hinges 91 are not formed by a single slot 73 they provide more longitudinal stiffness than the hinges of FIG. 16A. They also provide some extra torque stiffness which, as explained above, is provided by curved lips 87, 79 in curved slots 85, 81.

Concave section 77 is able to rotate within concave section 75 to a predetermined maximum extend determined by the width of the circumferential portions of slots 73*a* and 73*b*, as well as the length of the curved slots 85 and 81.

Fracture elements 89 (not shown in FIG. 16E but further details are shown in FIGS. 18B-18E) may be applied in the same way as in the embodiment of FIG. 16A.

Figure 16F:
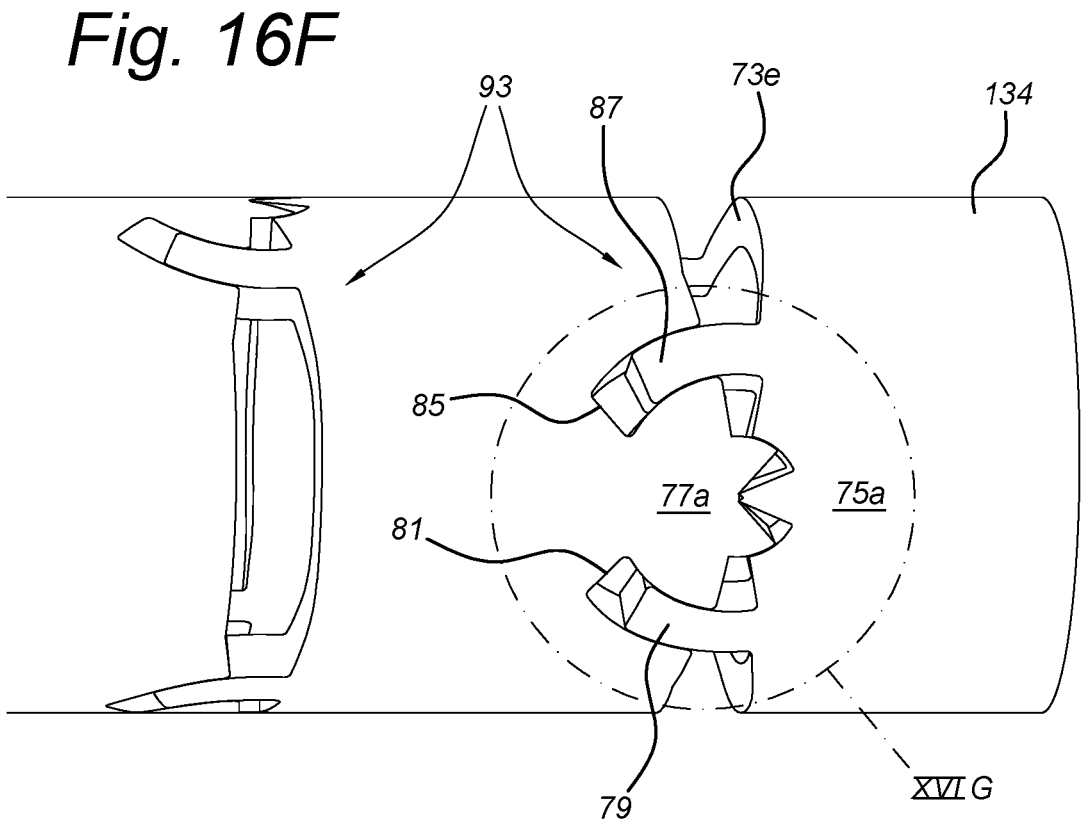

FIG. 16F shows a further alternative hinge embodiment. FIG. 16F shows hinges 93 formed by single slots 73*e* entirely surrounding tube element 134. The same reference numbers in FIG. 16F refer to the same elements as in FIG. 16A. Slot 73*e* is identical to slot 73 of the hinge shown in FIG. 16A apart from the portion between convex section 77*a* and concave section 75*a* such that convex section 77*a* and concave section 75*a*, respectively, differ in shape from convex portion 77 and concave section 75, respectively. This is shown in more detail in FIG. 16G which is an enlarged view of a portion indicated by XVIG in FIG. 16F.

Figure 16G:
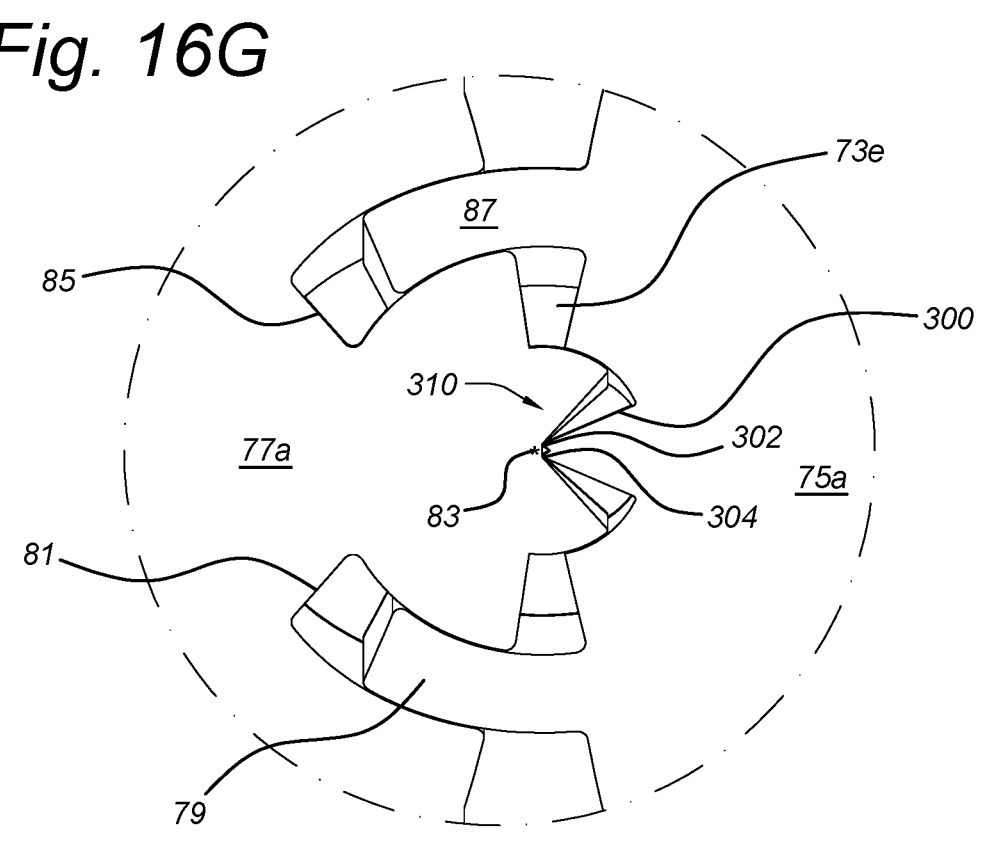

In the embodiment of FIG. 16G, the convex outside surface of convex section 77*a* is provided with a V-shaped notch 310. V-shaped notch 310 has two long sides 310(1) and 310(3), as shown in further enlarged view of FIG. 16H, and a base 310(2) connecting both long sides 310(1) and 310(3). In the embodiment shown, base 310(2) is straight but the invention is not restricted to this example. Base 310(2) may be slightly curved, e.g., having a V-shape or U-shape of which the base is pointing away from center point 83.

Concave section 75*a* is provided with an extension which is shown here as a V-shaped extension 300 accommodated by V-shaped notch 310. At its base, V-shaped extension 300 is provided with two corners 302 and 304 located at opposite sides of but at equal distance from a virtual line on the surface of tube element 134 and parallel to the central longitudinal axis 98 of tube element 134. In the embodiment shown, corners 302 and 304 are formed by providing the base of V-shaped extension 300 with a V-shape of which the base is pointing away from center point 83. However, the invention is not limited to this example. Corners 302 and 304, respectively, in the situation of FIG. 16G where convex section 77*a* and concave section 75*a* are not rotated relative to one another, contact or are extremely close to locations of V-shaped notch 310 where base 310(2) transitions into long sides 310(1) and 310(3), respectively. Here, "extremely close" refers to a distance less than 0.5 μm, preferably less than 0.1 μm. Corners 302 and 304 can be formed such that they each can contact V-shaped notch 310 only in a single point. In an embodiment, these corners 302 and 304 may still be attached to the opposing wall of V-shaped notch 310 after the laser or water cutting process. These attachments are designed such that they will easily fracture once a bending force is exerted on hinge 93 without deforming any other portion of the hinge structure (cf. also FIG. 18 which explains this for fracture elements 89). Then, after fracturing, corners 302 and 304 will still contact the opposing wall of V-shaped notch 310 making the structure even more stable.

Figure 16H:
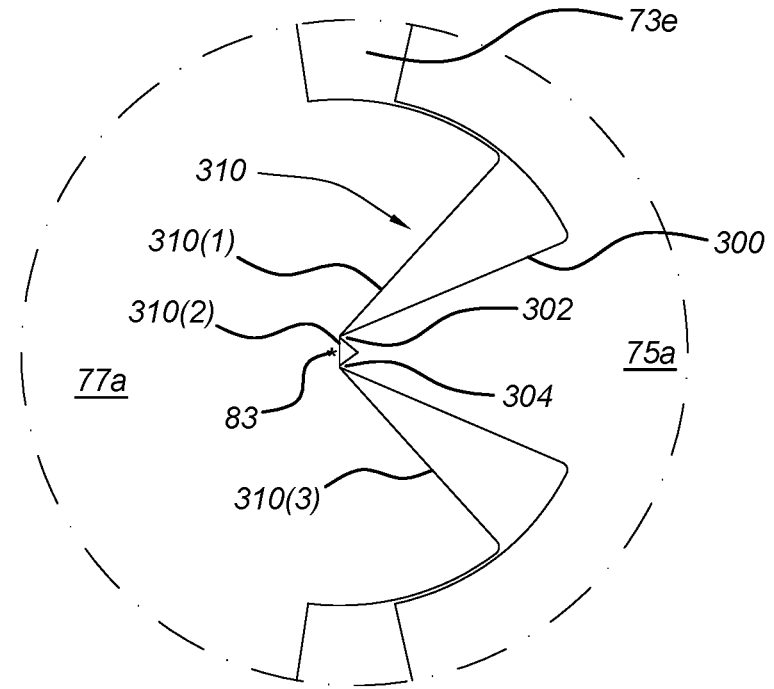

However, in the situation shown in FIG. 16H, convex section 77*a* and concave section 75*a* are rotated relative to one another, resulting in tilting of V-shaped extension 300 inside V-shaped notch 310 about corner 302 which then acts as a tilting point. So, then, corner 302 remains in contact with the transition point of base 310(2) and long side 310(1), and corner 304 is tilted away from the transition point of base 310(2) and long side 310(3).

In the embodiment of FIGS. 16F-16H, tube element 134 is provided with the same (or similar) structure at a location rotated 90° in the tangential direction.

The structure shown in FIGS. 16E-16H may solve the following issue. If tube element 134 is part of an instrument which is provided with an actuation cable 184 and such actuation cable 184 is tensioned for some actuation action at the tip of the instrument, at locations where such action cable 184 is not located exactly in the center of the tube element 134, the tube element 134 may have a tendency of bending. The effect of the structure shown in FIG. 16F-16H is that a certain threshold bending force should be exerted on hinge 93 before convex section 77*a* and concave section 75*a* start rotating relative to one another because, in a rest position, V-shaped extension 300 is supported by two corners 302, 304 at its base. The effect is the same as with a chair or table where one needs a threshold force to tilt the chair or table. Consequently, even if an off-axis actuation cable 184 is tensioned, hinge 93 tends to be not rotated. If one applies a plurality of identical or similar hinges 93 along at least a portion of tube element 134, that portion will have a larger tendency to remain straight. Again, adjacent hinges 93 in the longitudinal direction may be rotated about 90° relative to one another in the tangential direction to provide tube element 134 with flexibility in all directions.

It will be evident that FIGS. 16F-16H only show one example of a more general concept. The general concept can be worded as follows. The slotted structure of hinge 93 is configured such that, at one side of tube element 134, it comprises two portions 77*a*, 75*a* of tube element 134 at opposite sides of a slot 73*e*, the two portions 77*a* and 75*a* are configured such that they can rotate about a center point 83. In a rest situation, one of the portions, here 75*a*, is supported by the other portion, here 77*a*, at two points which points are located at opposite sides of and equal distance from a virtual line on the surface of tube element 134 parallel to central longitudinal axis 98.

The minimum width of slots of the slotted structures 72, 74, 106, 136, 156 can be made very small, i.e. equal to 0 μm or very close to that. This is e.g. preferred in slotted structure 72 where convex section 77 abuts concave section 75 (cf. FIG. 16A).

Figure 18A:
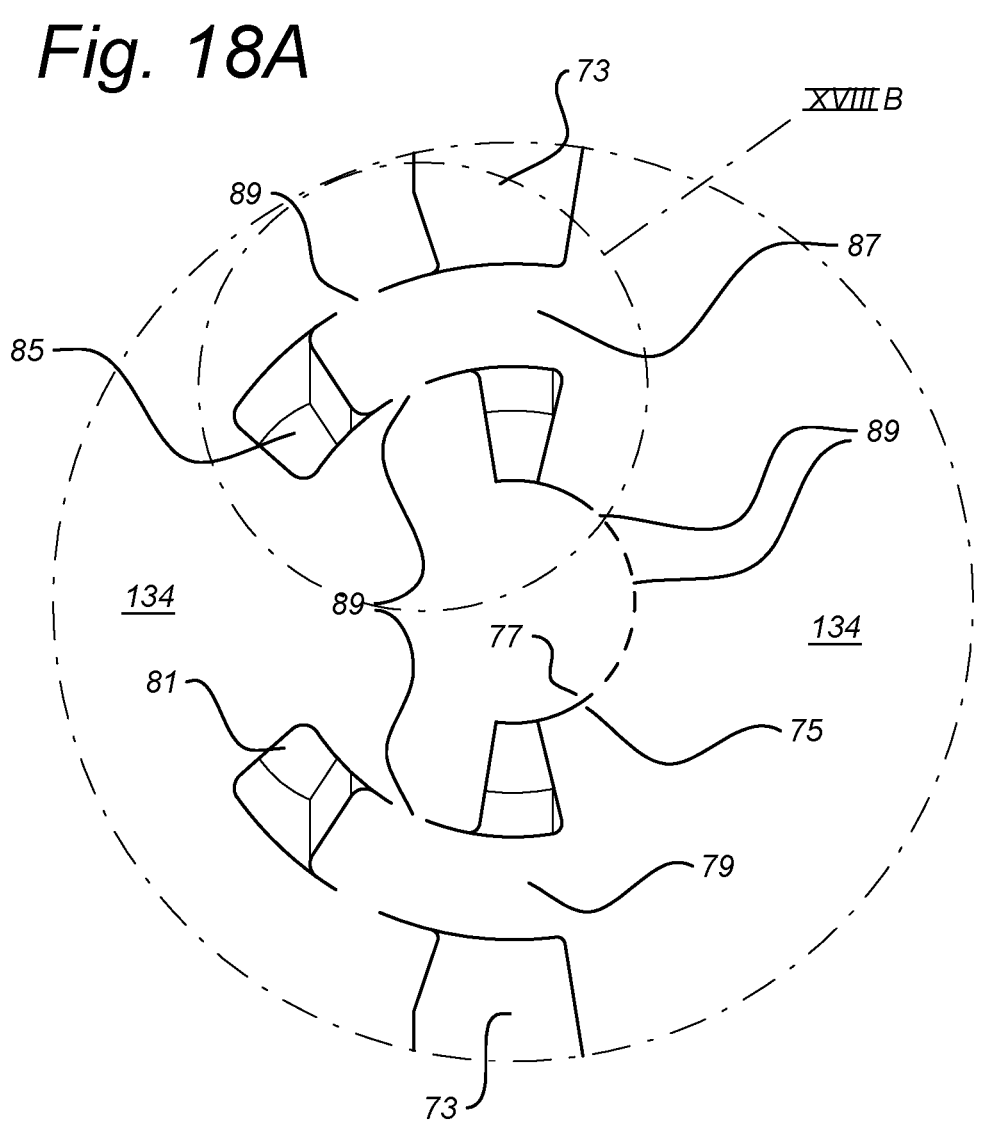
FIGS. 18A, 18B, 18C, 18D, and 18E show examples of fracture elements in a slotted hinge structure.

FIG. 18A shows how slot 73 in, for example, outer tube element 134 at the location where convex section 77 abuts concave section 75 can be made narrow while using fracture elements 89. FIG. 18A shows an enlarged portion of the slotted structure 72 shown in FIG. 16A directly after its manufacturing. It shows that convex section 77 is, then, still attached to concave section 75 by means of a plurality of fracture elements 89. Moreover, lips 87 and 79 are still attached to the opposing part of the tube element 134 by means of one or more fracture elements 89.

Such fracture elements 89 can be made as follows. Slot 73 is, e.g., made by directing a laser beam, or water beam, with a predetermined energy and width to the tube element such as to cut through the entire thickness of the tube element. The laser beam moves relative to the tube element outer surface by moving a laser source relative to that outer surface. However, at locations where fracture elements 89 are to be formed, the laser beam is interrupted for a certain period of time whereas the laser source still moves relative to the tube element outer surface.

As explained above, when deflecting different portions of slotted structure 72 relative to one another for the first time, these fracture elements 89 will fracture. A great advantage of such fracture elements 89 is that, after being fractured, the distance between two opposite sides of the fracture element 89 is substantially 0 μm which results in an extremely low play between them.

Figure 18B:
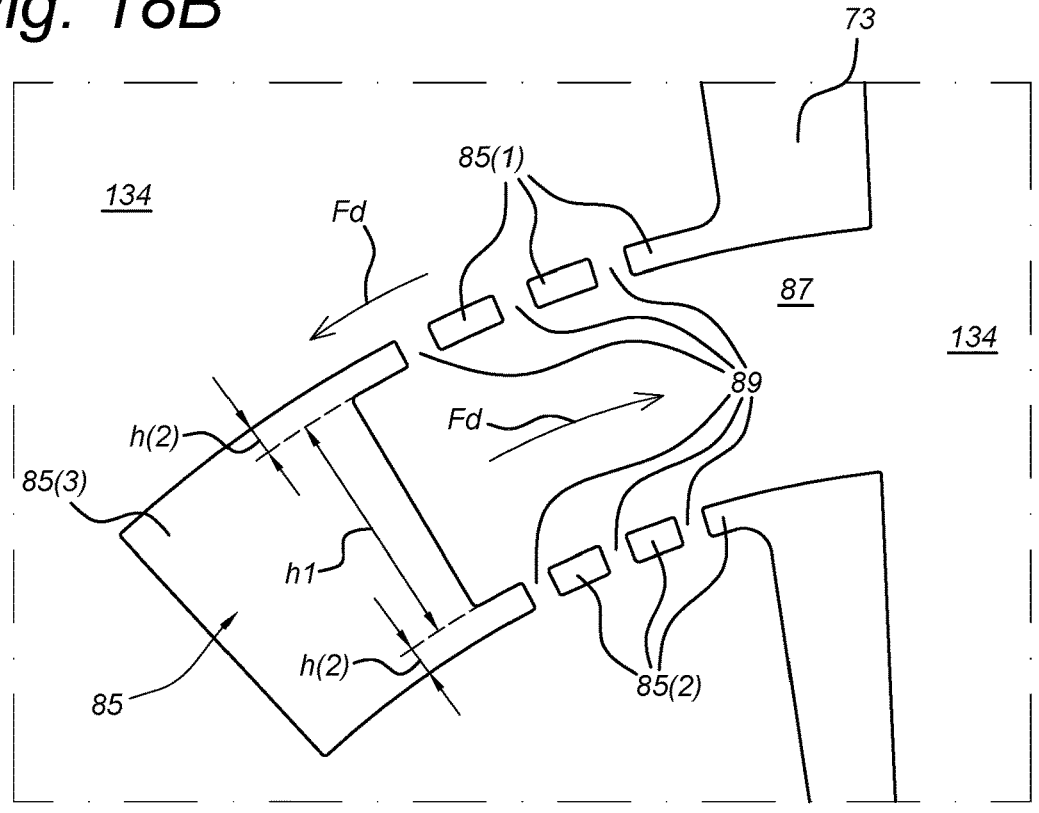
Figure 18C:
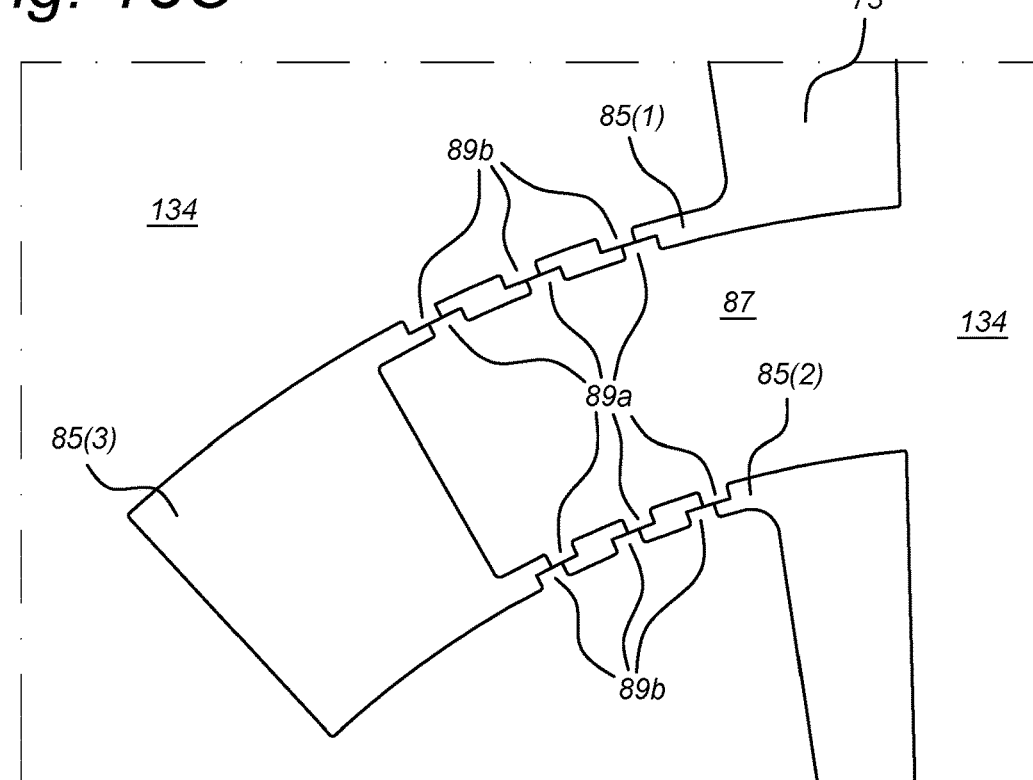

FIGS. 18B and 18C shows such fracture elements 89 in greater detail of a first embodiment. I.e., FIG. 18B is an enlarged view of a portion XIIXB shown in FIG. 18A. Curved slot 85 is shown to have three portions 85(1), 85(2), and 85(3). Together these three portions 85(1), 85(2), and 85(3) form a U shaped channel where portions 85(1) and 85(3) form the long sides and portion 85(2) forms the short, lower base side of the U shaped channel. Lip 87 is surrounded by portions 85(1), 85(2), and 85(3).

Like slot 73 portions 85(1), 85(2), and 85(3) are formed by, e.g., laser or water cutting through tube element 134. The width h(2) of portions 85(1) and 85(3) may be the same and be substantially equal to the width of the laser (or water) beam used to produce these portions 85(1), 85(3). The size of portion 85(2) depends on the path length lip 87 should be able to move within curved slot 85. Directly after such cutting action, lip 87 is still attached to opposing portions of tube element 134 by means of the fracture elements 89. As explained above, that provides tube element 134 with more rigidity after the cutting process such that tube element 134 can be treated easier, e.g. when another tube element is inserted into tube element 134 or tube element 134 is inserted into another tube element.

In use, the slotted structure shown in FIGS. 18A-18C is part of a hinge structure, as explained above. If the portion of the tube element 134 in which the slotted structure is located is bent, a force Fd is exerted by means of which lip 87 is moved inside curved slot 85. Force Fd is indicated in FIG. 18B with two arrows in order to show that lip 87 and opposing side of tube element 134 are moved relative to one another. The actual force Fd may be in a direction opposite to the one shown in FIG. 18B. Due to force Fd caused by bending tube element 134 fracture elements 89 will fracture such that lip 87 can move freely inside curved slot 85.

FIG. 18C shows that each one of the fracture elements 89 will fracture into two opposing separated fracture element portions 89a and 89b. In an embodiment, each fracture element 89 has a predetermined width and the fracture element portions 89a, 89b will have substantially the same width at their outer surfaces facing one another. Thus, in use, these fracture element portion 89a, 89b will be in contact with one another with their outer surfaces facing one another as long as the movement of the fracture element portions 89a, 89b relative to one another is not larger than this width. In an advantages embodiment, the width is so large that even in their maximum possible relative movement, as allowed by the width of slot 73, fracture element portions 89a, 89b still contact each other. So, tangential play in the slotted structure is kept to a minimum.

Figure 18D:
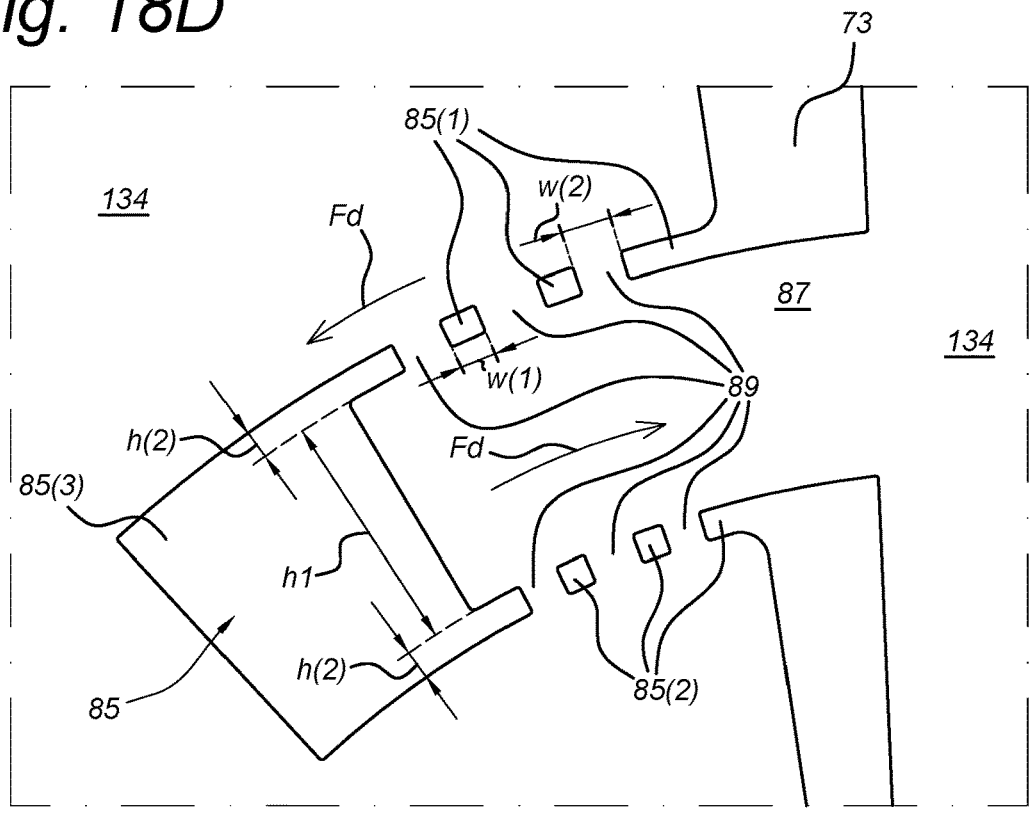
Figure 18E:
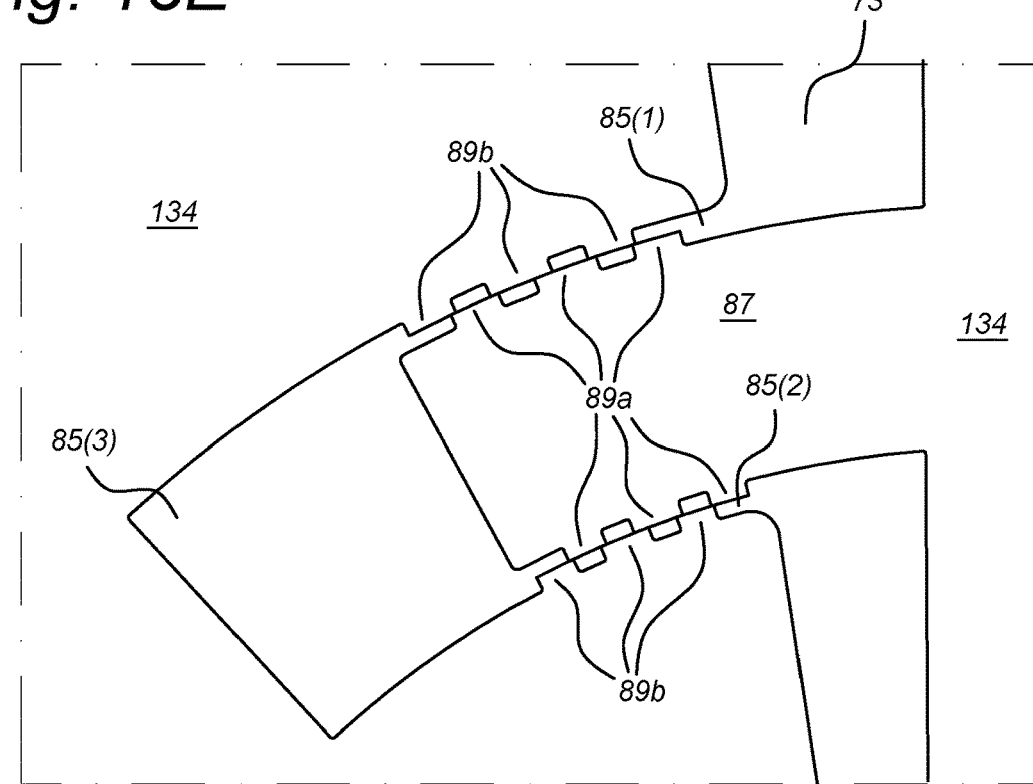

FIGS. 18D and 18E show a further embodiment of fracture elements 89. Fracture elements 89 of FIGS. 18D and 18E may have the same form as in FIGS. 18B and 18C, However, the distance w(2) between adjacent fracture elements 89 is now smaller than the width w(1) of the fracture elements 89 themselves. In FIGS. 18B and 18C the situation is shown where this mutual distance between adjacent fracture elements 89 is larger than the width of the individual fracture elements 89. Consequently, in the embodiment of FIGS. 18D and 18E, even when lip 87 and opposing side of tube element 134 are moved relative to one another along a distance larger than a distance equal to width w(1) (cf. FIG. 18E), one or more of the fracture element portions 89a, 89b may still contact one another because they cannot move inside the space between adjacent fracture elements 89. I.e., that space is too small to accommodate such fracture elements 89. This provides an even larger playless capacity in the tangential direction.

Referring back to FIG. 18A, fracture elements 89 between convex section 77 and concave section 75 are designed in the same way. So, by rotating convex section 77 inside concave section 75 with a predetermined force fracture elements 89 will fracture and each fracture element 89 leaves two fracture element portions 89a and 89b. These latter fracture element portions 89a and 89b will have the same form and function as shown in FIG. 18C. I.e., the slotted structure is configured such that convex section 77 can rotate within concave section 75 until rotation is blocked by the structure. The fracture elements 89 have such a width that, after being fractured, fracture element portions 89a and 89b have surfaces facing one another and always contacting one another during the entire maximum possible rotation. As can be seen, consequently, even after being manufactured convex section 77 and concave section 75 contact one another such that play in the longitudinal direction between convex section 77 and concave section 75 is kept to a minimum.

The more slotted structures of the flexible tube element 134, forming the hinges, are produced with such fracture elements 89 the more hinges will show playless properties both in the tangential and longitudinal direction. Consequently, a flexible tube element 134 can be made in which play in both the tangential and longitudinal direction is drastically reduced which is especially an advantages feature for longer instruments, e.g., instruments longer than 1 meter.

Fracture elements 89 should be designed in the following way. Before being fractured, each fracture element 89 is attached to opposite portions of tube element 134. These opposite portions of tube element 134 have respective yield stress values defining the force above which a permanent deformation of these opposite portions occurs. Moreover, each fracture element 89 has a respective fracture tensile stress value defining the force to be applied to fracture the fracture element 89. The tensile stress value of each fracture element 89 should be lower than the yield stress values of these opposite portions of tube element 134. For instance, the tensile stress value of each fracture element 89 is in a range of 1%-80% of the yield stress of these portions of the tube element 134, This range may, alternatively, be 1%-50%.

FIGS. 19A and 19B schematically show how cables 90 can be connected to the tip section by means of crimp bushings. FIG. 19A shows a 3D view of such a tip section and FIG. 19B shows a front view of the embodiment of FIG. 19A. These FIGS. 19A and 19B show but one possible example of using crimp bushings.

The tips section as shown in FIG. 19A is the one of tubular body 18 as shown in FIG. 9A and the same reference signs refer to the same elements as in FIG. 9A. However, the principle of using crimp bushings can be applied to all other embodiments as well.

As shown, in the embodiment of FIGS. 19A and 19B, strips 138 are implemented as two different types, i.e., alternating strips 138a and 138b. Strip 138a is designed such that, at its distal end, it is attached to ring-shaped portion 140. At its proximal end 145, strip 138a is disconnected from ring-shaped portion 78. Moreover, proximal end 145 may be provided with an additional lip 147. Adjacent to strip 138*a*, at both sides, strips 138*b* are present which are at both their distal end and proximal end, respectively, attached to ring-shaped portion 140 and ring-shaped portion 78, respectively.

Intermediate tube element 88*a* (not visible in FIG. 19A) ends within outer tube element 134 at a location in a plane perpendicular to the central axis 98 coinciding with the most proximal end of slots 139. A crimp bushing 143 is pushed over the distal end of each cable 90 such that each crimp bushing 143 is aligned with one slot 139. Preferably, the arrangement is such that, before the shrinking process, each crimp sleeve 143 partly extends in one slot 139, as is clearly shown in FIG. 19B. The diameters of the crimp sleeves 143 are so large that each one of them completely covers one cable channel 96 inclusive of the surrounding intermediate tube element material. So when looking from the front, one can only see portions 88*a*2 of intermediate tube element 88*a* (cf. FIG. 19B).

Crimp sleeves 143 are made of a deformable material like any suitable metal. Once pushed over the cables 90, a suitable force is applied to the outer surface of each crimp sleeve 143 to crimp them and clamp each one of them to one of the cables 90. This can advantageously be done while a portion of cable 90 extends beyond the most distal portion of outer tube element 86, 134. Once crimped on cable 90, the other end of cable 90 can be inserted into one of the channels 96, 97 until the cable 90 cannot be inserted any further due to the crimp bushing being stopped by the distal end of channel 96, 97.

Figure 19C:
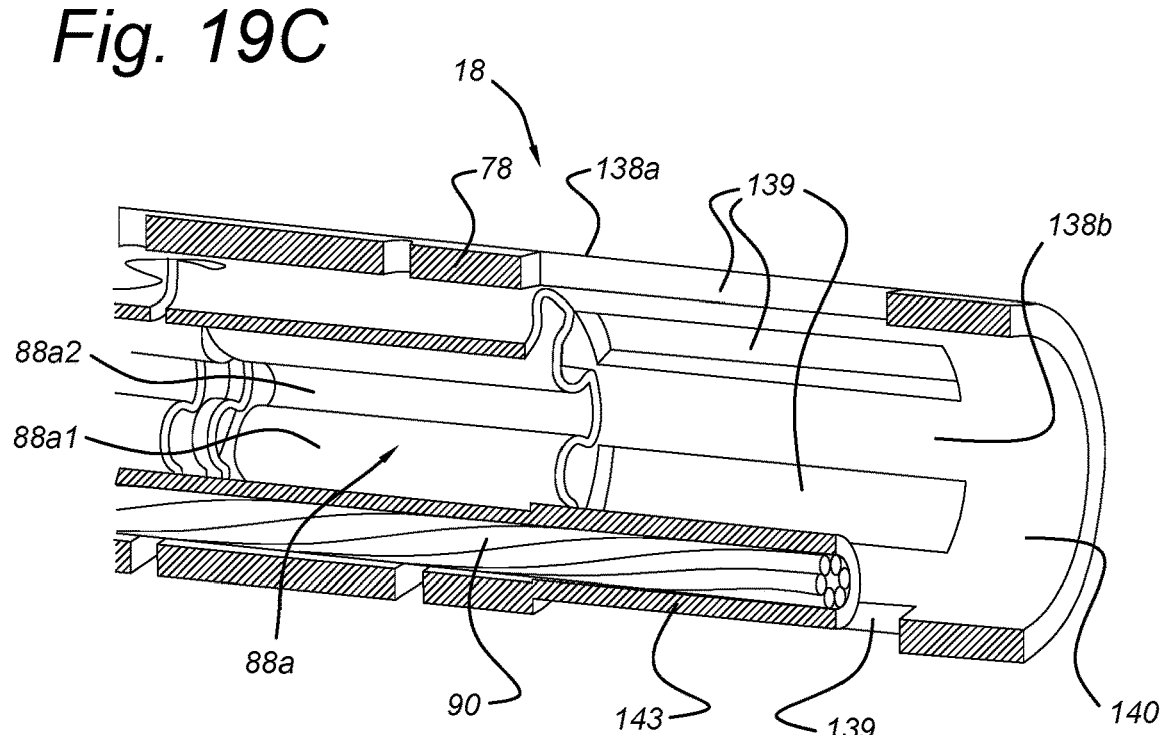

This has been shown in more detail in FIG. 19C. FIG. 19C is a longitudinal cross section of the distal portion of the instrument shown in FIGS. 19A, 19B. As FIG. 19C shows, the distal end side of intermediate tube element 88*a* is, viewed in the longitudinal direction, located at the most proximal end of slots 139. Lips 147 are welded to the distal end side of intermediate tube element 88*a*, i.e., to an outer portion 88*a*2 thereof. In their operational status, crimp bushings 143 abut the distal end side of intermediate tube element 88*a*. Moreover, their cross sectional size is such that, in the operational status, their longitudinal direction is, preferably aligned with the longitudinal direction of body 18 whereas, at the same time, each one partly lays in one of the slots 139.

After being crimped against one cable 90 each crimp bushing 143 will prevent longitudinal movement of its corresponding cable 90 in cable channel 96 in the proximal direction of the steerable instrument. Now, deflectable zone 17 can be deflected by pulling on some of the cables 90 and relaxing opposing ones, as will be evident to persons skilled in the art.

Figure 20A:
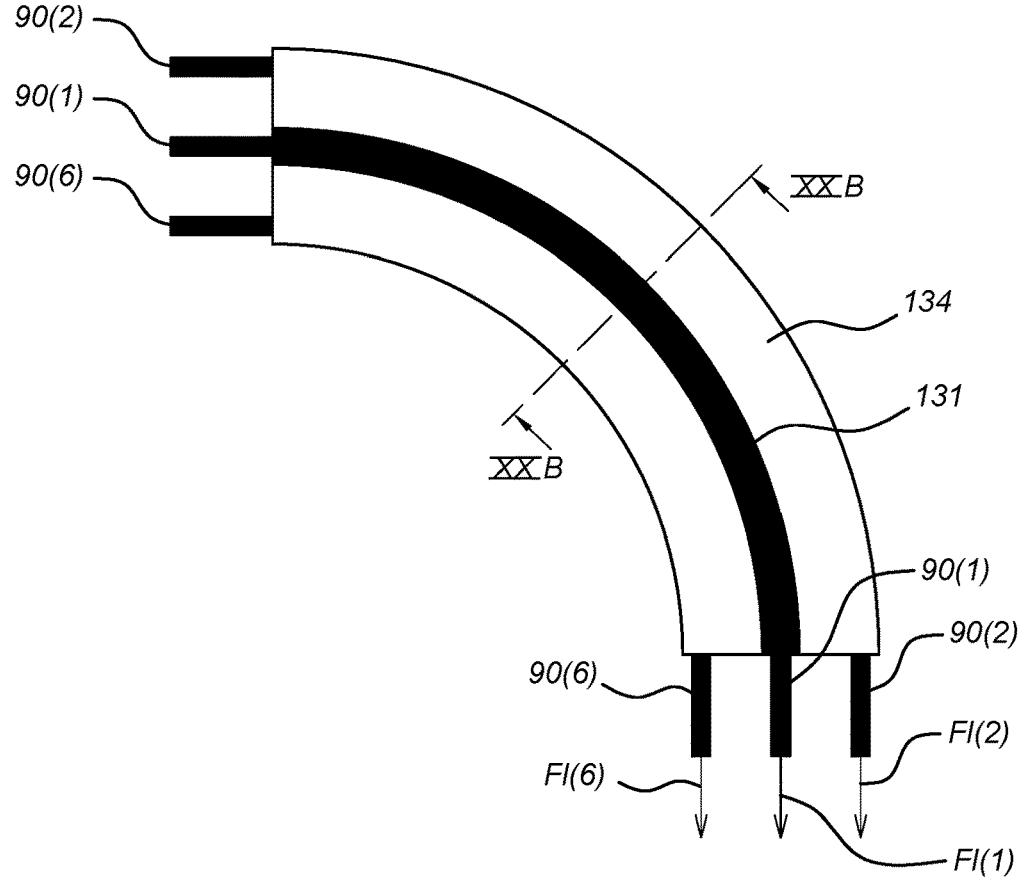
FIGS. 20A-20D show an embodiment with rearranged cables in an intermediate zone to counteract undesired rotational forces on the instrument when some cables are tensioned in order to deflect the distal end of the instrument.

FIGS. 20A-20D illustrate another embodiment. FIG. 20A shows, in a schematical way, how a longitudinal force exerted on one or more of the cables 90 can result in a rotational force and, thus, possibly a rotational movement of a portion of the instrument.

Figure 20B:
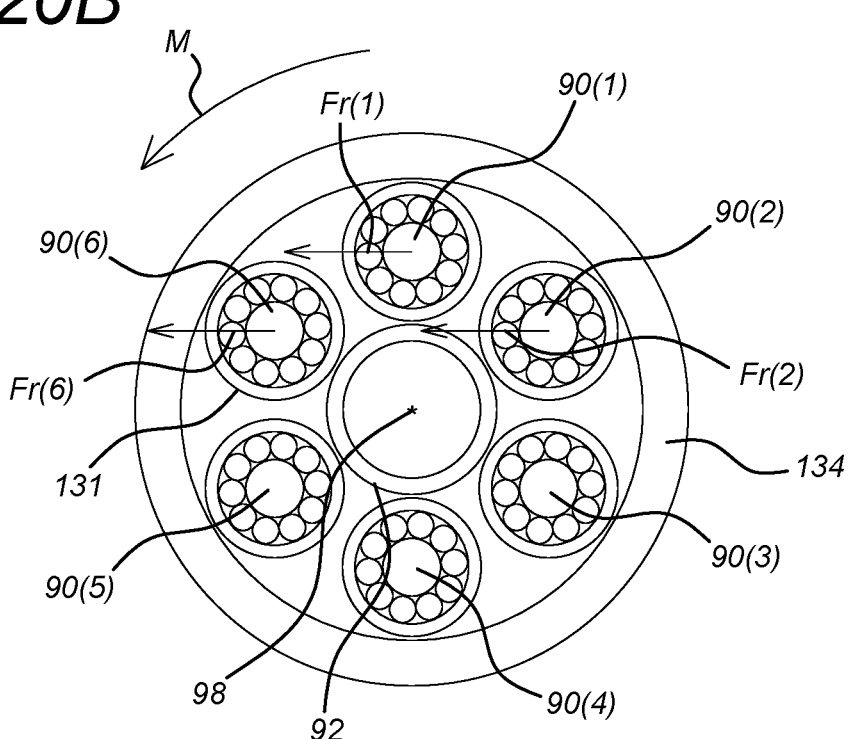

In FIG. 20A a portion of tube element 134 of the instrument is shown which is curved. This may be due to the fact that the instrument is inserted in a curved channel in a body. FIG. 20A schematically shows three out of six cables 90(1), 90(2), and 90(6). FIG. 20B, which is a cross section through the instrument indicated with arrows XXB in FIG. 20A, shows all six cables 90(1)-90(6). Their numbering is in the clockwise direction. Each one of the cables 90(1)-90(6) is located in one flexible tube 131, one of which being shown in FIG. 20A. Though FIGS. 20A-20D show six cables 90(1)-90(6) the solution of these Figures can be applied to any plurality of cables.

It is assumed a longitudinal force Fl(1), Fl(2) and Fl(6), respectively, in the proximal direction is exerted on cables 90(1), 90(2), and 90(6), respectively in order to establish a desired deflecting movement of the distal tip of the instrument. In an embodiment, the deflection may be one of all directions in 3D space. Cables 90(3), 90(4), and 90(5) are kept in a relaxed state. Since the shown portion of the instrument is curved longitudinal forces Fl(1), Fl(2) and Fl(6) translate into forces Fr(1), Fr(2) and Fr(6), respectively, on cables 90(1), 90(2), and 90(6), respectively, parallel to the surface in which the shown curve of the instrument is located, as shown in FIG. 20B. Since forces Fr(1), Fr(2) and Fr(6) are off-axis they result in a total rotational force on the instrument in a direction M.

Figure 20C:
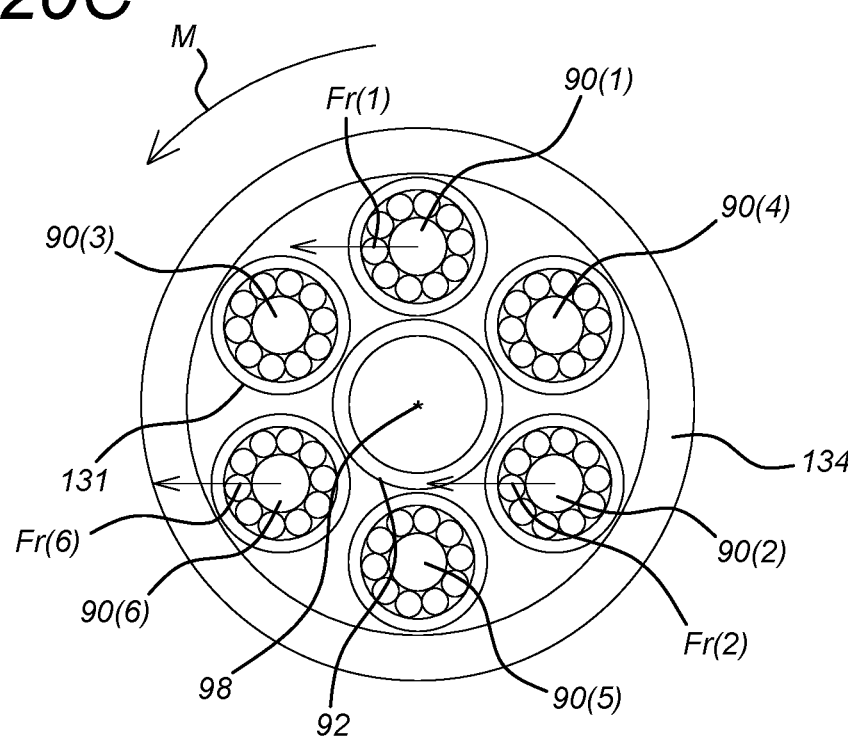
Figure 20D:
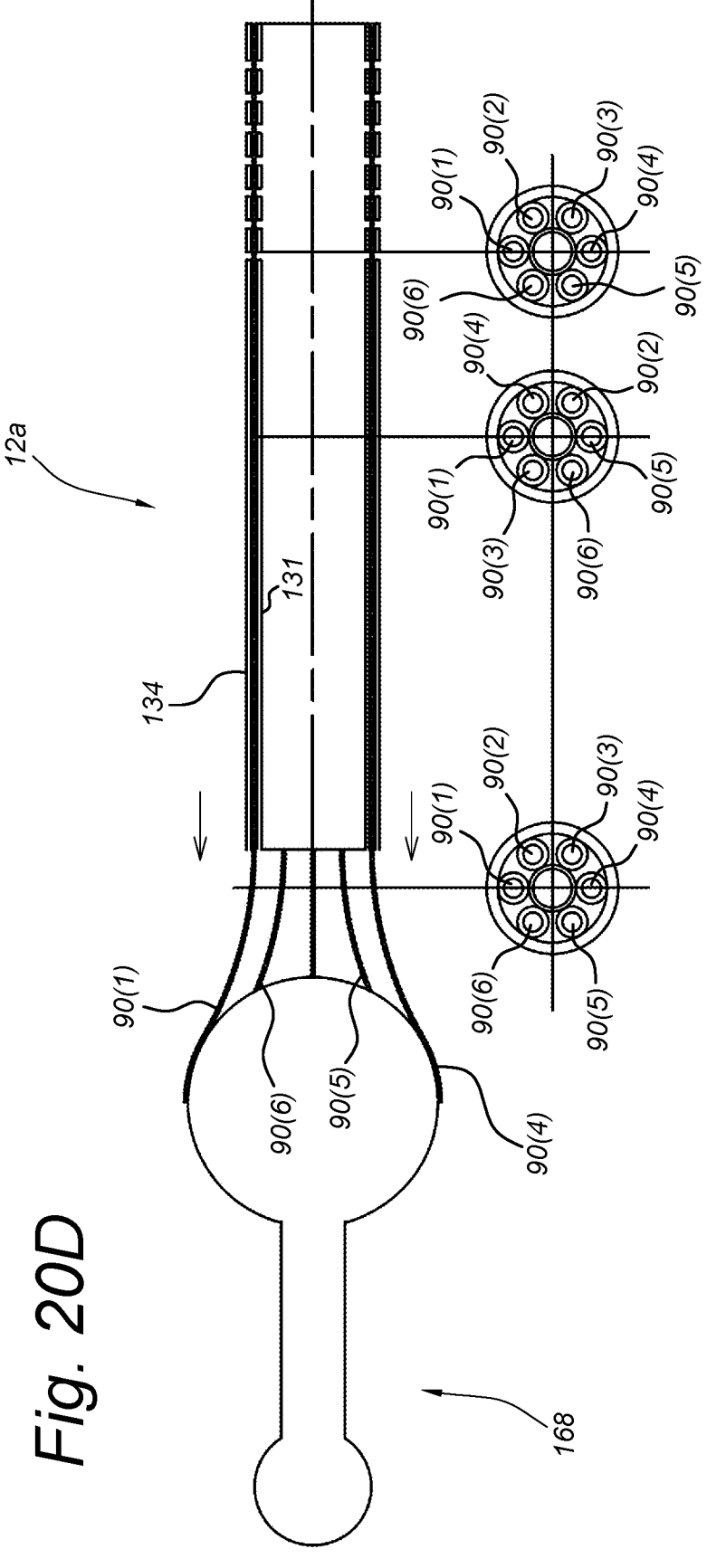

One way of counteracting this rotational force is shown in FIGS. 20C and 20D. In short, the solution presented here is changing the tangential order of the cables 90 in the intermediate flexible zone 12*a* of the instrument relative to the tangential order at the proximal and distal ends of the instrument. I.e., if the tangential order of cables 90 at the proximal end of the instrument is 90(1), 90(2), 90(3), 90(4), 90(5), 90(6) then the order at the distal deflectable zone 17 is the same, so, also 90(1), 90(2), 90(3), 90(4), 90(5), 90(6). However, the tangential order in intermediate flexible zone 12*a* of the instrument is then different. In the embodiment shown in FIGS. 20C and 20D, the tangential order in intermediate flexible zone 12*a* is changed into 90(1), 90(4), 90(2), 90(5), 90(6), 90(3). However, the invention is not restricted to this embodiment.

In the embodiment of FIGS. 20C and 20D, the tangential order of 90(1), 90(2), 90(3), 90(4), 90(5), 90(6) at the proximal end is changed into 90(1), 90(4), 90(2), 90(5), 90(6), 90(3) at intermediate flexible zone 12*a* at the entrance of outer tube element 134. Similarly, in the shown embodiment, the tangential order of 90(1), 90(4), 90(2), 90(5), 90(6), 90(3) at intermediate flexible zone 12*a* is changed to 90(1), 90(2), 90(3), 90(4), 90(5), 90(6) in the distal deflectable zone 17 at their transition. This may, e.g., be done by letting the cables 90 cross each other in a suitable way. If cables 90 are located in flexible tubes 131, such tubes 131 must be arranged in a crossing relationship in the transition areas.

The solution works as follows. As shown in FIG. 20C, forces Fr(1), Fr(2) and Fr(6), respectively, are still exerted on the same cables 90(1), 90(2) and 90(6), respectively. However, since these cables 90(1), 90(2) and 90(6) are now located in different tangential positions the exerted individual forces Fr(2) and Fr(6) on cables 90(2) and 90(6) are now in surfaces on the "other side" of the central longitudinal axis 98. That is, if force Fr(1) as exerted on cable 90(1) is in a first surface located on a first side of central longitudinal axis 98, then, forces Fr(2) and Fr(6) as exerted on cables 90(2) and 90(6) are in other surfaces on the opposite side of central longitudinal axis 98. Since forces Fr(1), Fr(2) and Fr(6) are all in the same direction, the total exerted rotational force is reduced.

The invention as explained with reference to FIGS. 20A-20D can be implemented in all instruments explained in the present document with reference to all other figures.

The method of manufacturing a flexible tube element according to the invention can be summarized as follows:

a. providing a tube element 88; 88*a*; 88*b*; 88*c*; 88*d*; 88*e* which has an inner surface and an outer surface, said inner surface surrounding a first channel 94, wherein said tube element 88; 88*a*; 88*b*; 88*c*; 88*d*; 88*e* is configured in at least one of the following shapes:

said outer surface has a corrugated cross section along its entire length defining a plurality of first cable channels 96; 96*a*; 96*b* each one arranged to accommodate at least a portion of one cable 90, and said inner surface has a corrugated cross section along its entire length defining a plurality of second cable channels 97 each one arranged to accommodate at least a portion of one cable 90, b. manufacturing at least one slotted structure 72; 74; 106; 156 in said tube element 88; 88*a*; 88*b*; 88*c*; 88*d*; 88*e* to provide said tube element 88; 88*a*; 88*b*; 88*c*; 88*d*; 88*e* with at least one deflectable section.

When the tube element is made from a metal, the at least one slotted structure is advantageously made by laser cutting. Such laser cutting may be performed by directing a laser beam perpendicular to said outer surface of said tube element. Either the tube element may be rotated during the laser cutting or the laser may be rotated about the central axis of the tube element. Thus, due to the corrugated structure of the tube element, the laser beam has a changing direction over time and is off-axis during at least during part of the cutting time.

Briefly stated, a steerable instrument is manufactured from the flexible tube element having a proximal end and a distal end by providing at least one steering device 168 at said proximal end, providing one ore cables and connecting said one or more cables to said steering device 168 at the proximal end and to said deflectable section to allow deflection of said deflectable section by means of said steering device 168.

Some final observations are as follows.

Many embodiments explained above aim towards a design in which each component serves multiple purposes and is integrally manufactured from one piece of base material. So instead of separate parts for cable channels, hinges, flexible zones and layer attachment means one can have one part with all functionality and features. This will minimize cost of part manufacturing and assembly tremendously.

Because the intermediate tube elements described above have at least a portion of a guiding channel for cables and are provided with slotted structures to provide them with a desired flexibility and deflectability, friction on the cables will be reduced. This greatly facilitates controlling the operation of the deflectable tip at the distal end, but also of a tool at the tip if such a tool is operated by a cable extending from the proximal end. Controlling manipulation of objects, e.g. in a human body, like gripping, moving, cutting, and/or stitching a needle through tissue, is becoming easier.

The distal end may comprise more than one deflectable zone. The most distal deflectable zone would be an articulation zone whereas the most but one distal zone could be a triangulation zone. One or more of these deflectable zones at the distal end could be controlled by longitudinal elements in a tube element made by laser cutting in an originally cylindrical tube, as explained in detail in above mentioned patent applications WO 2009/112060 A1, WO 2009/127236 A1, WO 2017/213491 A1, and WO 2018/067004. Alternatively, one or more of those deflectable zones can be controlled by ball-shaped steering elements or by a robot.

The examples and embodiments described herein serve to illustrate rather than to limit the invention. Elements from different embodiments can be combined to form embodiments not shown in the Figures unless such combinations are non-compatible. The person skilled in the art will be able to design alternative embodiments without departing from the scope of the claims. Reference signs placed in parentheses in the claims shall not be interpreted to limit the scope of the claims. Items described as separate entities in the claims or the description may be implemented as a single item or multiple hardware items combining the features of the items described.

It is to be understood that the invention is limited by the annexed claims and its technical equivalents only. In this document and in its claims, the verb "to comprise" and its conjugations are used in their non-limiting sense to mean that items following the word are included, without excluding items not specifically mentioned. In addition, reference to an element by the indefinite article "a" or "an" does not exclude the possibility that more than one of the element is present, unless the context clearly requires that there be one and only one of the elements. The indefinite article "a" or "an" thus usually means "at least one".

The invention claimed is:

1. A steerable instrument having a proximal end and a distal end and comprising a tubular body extending in a longitudinal direction along a central axis from said proximal end to said distal end, said tubular body having an intermediate flexible zone and at least one distal deflectable zone, said tubular body including at least one tube element made from a metal, the at least one tube element being provided with a first slotted structure in the intermediate flexible zone and a second slotted structure in the at least one distal deflectable zone, the tubular body being provided with tangential rotation blocking elements arranged such as to form a plurality of cable channels, each cable channel accommodating one of a plurality of cables, the plurality of cable channels comprising a plurality of first cable channels and a plurality of second cable channels, said plurality of cables being configured to be controlled at said proximal end by a steering device and being connected at said distal end to said at least one distal deflectable zone to allow deflection of said at least one distal deflectable zone by means of said steering device, wherein said at least one tube element comprises an intermediate tube element that:

is arranged in at least a portion of said tubular body, has an inner surface and an outer surface, said inner surface surrounding a first channel, has a cross section structure with a uniform thickness along its entire length, comprises said second slotted structure to provide said intermediate tube element with at least one deflectable section, and is configured in the following shapes to provide said tangential rotation blocking elements:

a. said outer surface has a corrugated cross section along its entire length, the corrugated cross section defining said plurality of first cable channels each one accommodating at least a portion of one cable, and b. said inner surface has a corrugated cross section along its entire length, the corrugated cross section of said inner surface defining said plurality of second cable channels each one accommodating at least a portion of one cable, wherein the plurality of first cable channels face radially outward and the plurality of second cable channels face radially inward in respect of the intermediate tube element, wherein said at least one tube element further comprises an outer tube element surrounding said intermediate tube element, the outer tube element contacting the intermediate tube element to define tapered portions of said plurality of first cable channels, and wherein said tapered portions are at least partly filled by a material comprising at leas one of portions of said outer tube element extending radially inward or a liner arranged between said intermediate tube element and said outer tube element.

2. The steerable instrument according to claim 1, configured to have said plurality of first cable channels, each one accommodating at least said portion of one cable, wherein the outer tube element encloses said intermediate tube element so as to cover said plurality of first cable channels.

3. The steerable instrument according to claim 1, wherein said outer tube element is provided with at least one of a first outer tube element slotted structure in said at least one distal deflectable zone and a second outer tube element slotted structure in said intermediate flexible zone.

4. The steerable instrument according to claim 1, wherein said outer tube element is shaped such as to form a plurality of third cable channels, each third cable channel opposing one first cable channel of the plurality of first cable channels such as to form together a fourth cable channel accommodating one cable of the plurality of cables.

5. The steerable instrument according to claim 1, wherein the material is configured to prevent the plurality of cables from getting stuck in said tapered portions.

6. The steerable instrument according to claim 1, wherein said outer tube element has a uniform thickness along its entire length.

7. The steerable instrument according to claim 1, wherein said outer tube element is attached to said intermediate tube element at least at one or more locations at a proximal end of said at least one deflectable section.

8. The steerable instrument according to claim 1, wherein said intermediate tube element has a cross section structure with a uniform thickness along its entire length such that said outer surface and said inner surface have a same corrugated structure along its entire length.

9. The steerable instrument according to claim 1, configured to have said plurality of second cable channels, each one accommodating at least said portion of one cable, wherein the tubular body is provided with an inner tube element arranged within said intermediate tube element such as to cover said plurality of second cable channels.

10. The steerable instrument according to claim 1, wherein said intermediate tube element has a cross section structure with a uniform thickness along its entire length such that said outer surface and said inner surface have a same corrugated structure, said intermediate tube element comprising outer portions forming an outer circumference of said intermediate tube element, and inner portions each shaped such as to enclose an essentially closed channel.

11. The steerable instrument according to claim 1, wherein at least one of said the plurality of cables is enclosed in a separate tube.

* * * * *